US010624748B2

(12) United States Patent
Ek et al.

(10) Patent No.: US 10,624,748 B2
(45) Date of Patent: Apr. 21, 2020

(54) SYSTEM AND METHOD FOR REPAIRING ARTICULAR SURFACES

(71) Applicant: Arthrosurface Incorporated, Franklin, MA (US)

(72) Inventors: Steven W. Ek, Bolton, MA (US); Anthony Miniaci, Bentleyville, OH (US); Timothy Brightman, Franklin, MA (US)

(73) Assignee: Arthrosurface Incorporated, Franklin, MA (US)

( * ) Notice: Subject to any disclaimer, the term of this patent is extended or adjusted under 35 U.S.C. 154(b) by 0 days.

(21) Appl. No.: 15/388,808

(22) Filed: Dec. 22, 2016

(65) Prior Publication Data

US 2017/0100251 A1   Apr. 13, 2017

Related U.S. Application Data

(63) Continuation-in-part of application No. 14/640,774, filed on Mar. 6, 2015, now Pat. No. 9,962,265.
(Continued)

(51) Int. Cl.
*A61F 2/30* (2006.01)
*A61F 2/40* (2006.01)
(Continued)

(52) U.S. Cl.
CPC ............ *A61F 2/30* (2013.01); *A61F 2/30756* (2013.01); *A61F 2/32* (2013.01); *A61F 2/38* (2013.01);
(Continued)

(58) Field of Classification Search
CPC ...... A61F 2/32; A61F 2/34; A61F 2/38; A61F 2/28; A61F 2/4241; A61F 2/30
See application file for complete search history.

(56) References Cited

U.S. PATENT DOCUMENTS

| 103,645 | A | 5/1870 | Muscroft |
| 992,819 | A | 5/1911 | Springer |

(Continued)

FOREIGN PATENT DOCUMENTS

| AU | 2001262308 | 12/2001 |
| AU | 2001259327 B2 | 2/2005 |

(Continued)

OTHER PUBLICATIONS

European Office Action dated Apr. 16, 2013 issued in European Patent Application No. 12 002 103.5, 5 pages.
(Continued)

*Primary Examiner* — Jason-Dennis N Stewart
(74) *Attorney, Agent, or Firm* — Grossman Tucker Perreault & Pfleger PLLC

(57) ABSTRACT

A joint replacement system for repairing an articular surface of a first bone of a joint includes an anchor portion and an implant portion. The anchor portion includes an anchor to be secured to the bone, and an anchor fixation head including a bone-facing surface (BFS) extending radially outward from the anchor and an implant facing surface (IFS) extending from a periphery of the BFS. The implant portion is formed from a material (e.g., CoCr) more dense than the material of the anchor portion (e.g., Ti) and includes a fixation cavity to receive at least a portion of the anchor fixation head (AFH), the fixation cavity includes an anchor facing surface (AFS) configured to form a frictional connection with the IFS, and a load bearing surface having a contour for articulating against a cooperating articulating surface of a second bone of the joint.

41 Claims, 23 Drawing Sheets

Related U.S. Application Data

(60) Provisional application No. 61/949,774, filed on Mar. 7, 2014, provisional application No. 61/949,789, filed on Mar. 7, 2014, provisional application No. 61/949,824, filed on Mar. 7, 2014, provisional application No. 61/950,762, filed on Mar. 10, 2014.

(51) Int. Cl.
    *A61F 2/46*         (2006.01)
    *A61F 2/32*         (2006.01)
    *A61F 2/38*         (2006.01)
    *A61F 2/42*         (2006.01)
    *A61B 17/04*       (2006.01)
    *A61B 17/86*       (2006.01)

(52) U.S. Cl.
CPC .............. *A61F 2/40* (2013.01); *A61F 2/4003* (2013.01); *A61F 2/4081* (2013.01); *A61F 2/42* (2013.01); *A61F 2/4606* (2013.01); *A61F 2/4618* (2013.01); *A61F 2/4637* (2013.01); *A61B 17/86* (2013.01); *A61B 2017/044* (2013.01); *A61B 2017/0409* (2013.01); *A61F 2002/305* (2013.01); *A61F 2002/3085* (2013.01); *A61F 2002/30331* (2013.01); *A61F 2002/30332* (2013.01); *A61F 2002/30462* (2013.01); *A61F 2002/30607* (2013.01); *A61F 2002/30614* (2013.01); *A61F 2002/30901* (2013.01); *A61F 2002/4022* (2013.01); *A61F 2002/4085* (2013.01); *A61F 2002/4627* (2013.01); *A61F 2002/4628* (2013.01); *A61F 2310/00011* (2013.01); *A61F 2310/00017* (2013.01); *A61F 2310/00023* (2013.01); *A61F 2310/00029* (2013.01); *A61F 2310/00047* (2013.01)

(56) References Cited

U.S. PATENT DOCUMENTS

| | | |
|---|---|---|
| 1,451,610 A | 4/1923 | Gestas |
| 2,267,925 A | 12/1941 | Johnston |
| 2,379,984 A | 7/1943 | Nereaux |
| 2,381,102 A | 10/1943 | Boyd |
| 2,570,465 A | 10/1951 | Lundholm |
| 2,919,692 A | 1/1960 | Ackermann |
| 3,176,395 A | 4/1965 | Warner et al. |
| 3,351,115 A | 11/1967 | Boehlow |
| 3,715,763 A | 2/1973 | Link |
| 3,840,905 A | 10/1974 | Deane |
| 3,852,830 A | 12/1974 | Marmor |
| 4,016,651 A | 4/1977 | Kawahara et al. |
| 4,016,874 A | 4/1977 | Maffei et al. |
| 4,034,418 A | 7/1977 | Jackson et al. |
| D245,259 S | 8/1977 | Shen |
| 4,044,464 A | 8/1977 | Schiess et al. |
| 4,158,894 A | 6/1979 | Worrell |
| 4,304,011 A | 12/1981 | Whelan, III |
| 4,309,778 A | 1/1982 | Buechel et al. |
| 4,319,577 A | 3/1982 | Bofinger et al. |
| 4,330,891 A | 5/1982 | Brånemark et al. |
| 4,340,978 A | 7/1982 | Buechel et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,565,768 A | 1/1986 | Nonogaki et al. |
| 4,567,885 A | 2/1986 | Androphy |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,703,761 A | 11/1987 | Rathbone et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A | 2/1988 | Fox |
| 4,729,761 A | 3/1988 | White |
| 4,743,262 A * | 5/1988 | Tronzo ................ A61F 2/30734 623/22.32 |
| 4,778,473 A | 10/1988 | Matthews et al. |
| 4,781,182 A | 11/1988 | Purnell et al. |
| 4,787,383 A | 11/1988 | Kenna |
| 4,788,970 A | 12/1988 | Kara et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,919,671 A | 4/1990 | Karpf |
| 4,920,958 A | 5/1990 | Walt et al. |
| 4,927,421 A | 5/1990 | Goble et al. |
| 4,936,853 A | 6/1990 | Fabian et al. |
| 4,938,778 A | 7/1990 | Ohyabu et al. |
| 4,940,467 A | 7/1990 | Tronzo |
| 4,945,904 A | 8/1990 | Bolton et al. |
| 4,955,916 A | 9/1990 | Carignan et al. |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,030,219 A | 7/1991 | Matsen, III et al. |
| 5,053,049 A | 10/1991 | Campbell |
| 5,092,895 A | 3/1992 | Albrektsson et al. |
| 5,100,405 A | 3/1992 | McLaren |
| 5,122,144 A | 6/1992 | Bert et al. |
| 5,127,413 A | 7/1992 | Ebert |
| 5,127,920 A | 7/1992 | MacArthur |
| 5,147,386 A | 9/1992 | Carignan et al. |
| 5,152,797 A | 10/1992 | Luckman et al. |
| 5,154,720 A | 10/1992 | Trott et al. |
| 5,180,384 A | 1/1993 | Mikhail |
| 5,192,291 A | 3/1993 | Pannek, Jr. |
| 5,194,066 A | 3/1993 | Van Zile |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,254,119 A | 10/1993 | Schreiber |
| 5,255,838 A | 10/1993 | Gladdish, Jr. et al. |
| 5,263,498 A | 11/1993 | Caspari et al. |
| 5,263,987 A | 11/1993 | Shah |
| 5,269,784 A | 12/1993 | Mast |
| 5,282,863 A | 2/1994 | Burton |
| 5,290,313 A | 3/1994 | Heldreth |
| 5,306,278 A | 4/1994 | Dahl et al. |
| 5,312,411 A | 5/1994 | Steele |
| 5,314,478 A | 5/1994 | Oka et al. |
| 5,314,482 A | 5/1994 | Goodfellow et al. |
| 5,324,295 A | 6/1994 | Shapiro |
| 5,326,366 A | 7/1994 | Pascarella et al. |
| 5,336,224 A | 8/1994 | Selman |
| 5,336,266 A | 8/1994 | Caspari et al. |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |

(56) References Cited

U.S. PATENT DOCUMENTS

| | | |
|---|---|---|
| 5,395,376 A | 3/1995 | Caspari et al. |
| 5,395,401 A | 3/1995 | Bahler |
| 5,409,490 A | 4/1995 | Ethridge |
| 5,409,494 A | 4/1995 | Morgan |
| 5,411,504 A | 5/1995 | Vilas |
| 5,413,608 A | 5/1995 | Keller |
| 5,423,822 A | 6/1995 | Hershberger |
| 5,423,823 A | 6/1995 | Schmieding |
| 5,425,733 A | 6/1995 | Schmieding |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,514,139 A | 5/1996 | Goldstein et al. |
| 5,520,695 A | 5/1996 | Luckman |
| 5,522,900 A | 6/1996 | Hollister |
| 5,522,901 A | 6/1996 | Thomas et al. |
| 5,534,031 A | 7/1996 | Matsuzaki et al. |
| 5,540,696 A | 7/1996 | Booth, Jr. et al. |
| 5,562,664 A | 10/1996 | Durlacher et al. |
| 5,580,352 A | 12/1996 | Sekel |
| 5,580,353 A | 12/1996 | Mendes et al. |
| 5,591,170 A | 1/1997 | Spievack et al. |
| 5,593,448 A | 1/1997 | Dong |
| 5,593,450 A | 1/1997 | Scott et al. |
| 5,595,193 A | 1/1997 | Walus et al. |
| 5,597,273 A | 1/1997 | Hirsch |
| 5,601,550 A | 2/1997 | Esser |
| 5,607,480 A | 3/1997 | Beaty |
| 5,609,639 A | 3/1997 | Walker |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,461 A | 12/1997 | Pappas et al. |
| 5,702,465 A | 12/1997 | Burkinshaw |
| 5,702,467 A | 12/1997 | Gabriel et al. |
| 5,720,753 A | 2/1998 | Sander et al. |
| 5,741,266 A | 4/1998 | Moran et al. |
| 5,765,973 A | 6/1998 | Hirsch et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,800,440 A | 9/1998 | Stead |
| 5,810,851 A | 9/1998 | Yoon |
| 5,816,811 A | 10/1998 | Beaty |
| 5,817,095 A | 10/1998 | Smith |
| 5,824,087 A | 10/1998 | Aspden et al. |
| 5,824,105 A | 10/1998 | Ries et al. |
| 5,827,285 A | 10/1998 | Bramlet |
| RE36,020 E | 12/1998 | Moore et al. |
| 5,871,545 A | 2/1999 | Goodfellow et al. |
| 5,879,396 A | 3/1999 | Walston et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,891,150 A | 4/1999 | Chan |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,241 A | 7/1999 | Menut et al. |
| 5,928,286 A | 7/1999 | Ashby et al. |
| 5,951,603 A | 9/1999 | O'Neil et al. |
| 5,957,979 A | 9/1999 | Beckman et al. |
| 5,964,752 A | 10/1999 | Stone |
| 5,964,768 A | 10/1999 | Huebner |
| 5,964,805 A | 10/1999 | Stone |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,019,790 A | 2/2000 | Holmberg et al. |
| 6,033,410 A | 3/2000 | McLean et al. |
| 6,045,554 A | 4/2000 | Grooms et al. |
| 6,045,564 A | 4/2000 | Walen |
| 6,052,909 A | 4/2000 | Gardner |
| 6,053,945 A | 4/2000 | O'Neil et al. |
| 6,059,831 A | 5/2000 | Braslow |
| 6,063,091 A | 5/2000 | Lombardo et al. |
| 6,069,295 A | 5/2000 | Leitao |
| 6,071,310 A | 6/2000 | Picha et al. |
| 6,081,741 A | 6/2000 | Hollis |
| 6,086,593 A | 7/2000 | Bonutti |
| 6,086,614 A | 7/2000 | Mumme |
| 6,099,571 A * | 8/2000 | Knapp .............. A61F 2/4225 623/18.11 |
| 6,102,948 A | 8/2000 | Brosnahan, III |
| 6,102,954 A | 8/2000 | Albrektsson et al. |
| 6,120,511 A | 9/2000 | Chan |
| 6,120,542 A | 9/2000 | Camino et al. |
| 6,132,433 A | 10/2000 | Whelan |
| 6,139,508 A | 10/2000 | Simpson et al. |
| 6,146,385 A | 11/2000 | Torrie et al. |
| 6,149,654 A | 11/2000 | Lanny |
| 6,152,960 A | 11/2000 | Pappas |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,206,926 B1 | 3/2001 | Pappas |
| 6,207,218 B1 | 3/2001 | Layrolle et al. |
| 6,217,549 B1 | 4/2001 | Selmon et al. |
| 6,217,619 B1 | 4/2001 | Keller |
| 6,228,119 B1 | 5/2001 | Ondrla et al. |
| 6,231,611 B1 | 5/2001 | Mosseri |
| 6,235,060 B1 | 5/2001 | Kubein-Meesenburg et al. |
| 6,245,074 B1 | 6/2001 | Allard et al. |
| 6,251,143 B1 | 6/2001 | Schwartz et al. |
| 6,254,605 B1 | 7/2001 | Howell |
| 6,270,347 B1 | 8/2001 | Webster et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,310,116 B1 | 10/2001 | Yasuda et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,364,910 B1 | 4/2002 | Shultz et al. |
| 6,375,658 B1 | 4/2002 | Hangody et al. |
| 6,383,188 B2 | 5/2002 | Kuslich |
| 6,402,785 B1 | 6/2002 | Zdeblick et al. |
| 6,415,516 B1 | 7/2002 | Tirado et al. |
| 6,416,518 B1 | 7/2002 | DeMayo |
| 6,443,954 B1 | 9/2002 | Bramlet et al. |

(56) References Cited

U.S. PATENT DOCUMENTS

| | | |
|---|---|---|
| 6,451,023 B1 | 9/2002 | Salazar et al. |
| 6,461,373 B2 | 10/2002 | Wyman et al. |
| 6,468,309 B1 | 10/2002 | Lieberman |
| 6,478,801 B1 | 11/2002 | Ralph et al. |
| 6,478,822 B1 | 11/2002 | Leroux et al. |
| 6,482,210 B1 | 11/2002 | Skiba et al. |
| 6,494,914 B2 | 12/2002 | Brown |
| 6,517,541 B1 | 2/2003 | Sesic |
| 6,517,542 B1 | 2/2003 | Papay et al. |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,547,823 B2 | 4/2003 | Scarborough et al. |
| 6,551,322 B1 | 4/2003 | Lieberman |
| 6,554,866 B1 | 4/2003 | Aicher et al. |
| 6,558,422 B1 | 5/2003 | Baker et al. |
| 6,569,202 B2 | 5/2003 | Whiteside |
| 6,575,980 B1 | 6/2003 | Robie et al. |
| 6,575,982 B1 | 6/2003 | Bonutti |
| 6,585,666 B2 | 7/2003 | Suh et al. |
| 6,589,281 B2 | 7/2003 | Hyde, Jr. |
| 6,591,581 B2 | 7/2003 | Schmieding |
| 6,599,321 B2 | 7/2003 | Hyde et al. |
| 6,602,258 B1 | 8/2003 | Katz |
| 6,607,561 B2 | 8/2003 | Brannon |
| 6,610,067 B2 | 8/2003 | Tallarida |
| 6,610,095 B1 | 8/2003 | Pope et al. |
| 6,623,474 B1 | 9/2003 | Ponzi |
| 6,626,950 B2 | 9/2003 | Brown et al. |
| 6,629,997 B2 | 10/2003 | Mansmann |
| 6,632,246 B1 | 10/2003 | Simon et al. |
| 6,679,916 B1 | 1/2004 | Frankle et al. |
| 6,679,917 B2 | 1/2004 | Ek |
| 6,720,469 B1 | 4/2004 | Curtis et al. |
| 6,746,451 B2 | 6/2004 | Middleton et al. |
| 6,755,837 B2 | 6/2004 | Ebner |
| 6,755,865 B2 | 6/2004 | Tarabishy |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,881,228 B2 | 4/2005 | Zdeblick et al. |
| 6,884,246 B1 | 4/2005 | Sonnabend et al. |
| 6,884,621 B2 | 4/2005 | Liao et al. |
| 6,893,467 B1 | 5/2005 | Bercovy |
| 6,913,463 B2 | 7/2005 | Blacklock |
| 6,923,813 B2 | 8/2005 | Phillips et al. |
| 6,926,739 B1 | 8/2005 | Oconnor |
| 6,951,538 B2 | 10/2005 | Ritland |
| 6,953,478 B2 | 10/2005 | Bouttens et al. |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,048,767 B2 | 5/2006 | Namavar |
| 7,063,717 B2 | 6/2006 | St. Pierre et al. |
| 7,112,205 B2 | 9/2006 | Carrison |
| 7,115,131 B2 | 10/2006 | Engh et al. |
| 7,118,578 B2 | 10/2006 | West, Jr. et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,192,432 B2 | 3/2007 | Wetzler et al. |
| 7,204,839 B2 | 4/2007 | Dreyfuss et al. |
| 7,204,854 B2 | 4/2007 | Guederian et al. |
| 7,229,448 B2 | 6/2007 | Goble et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augustino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,368,065 B2 | 5/2008 | Yang et al. |
| 7,371,260 B2 | 5/2008 | Malinin |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,575,578 B2 | 8/2009 | Wetzler et al. |
| 7,578,824 B2 | 8/2009 | Justin et al. |
| 7,604,641 B2 | 10/2009 | Tallarida et al. |
| 7,611,653 B1 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,731,738 B2 | 6/2010 | Jackson et al. |
| 7,738,187 B2 | 6/2010 | Pazidis et al. |
| 7,740,662 B2 | 6/2010 | Barnett et al. |
| 7,758,643 B2 | 7/2010 | Stone et al. |
| 7,776,085 B2 | 8/2010 | Bemero et al. |
| 7,806,872 B2 | 10/2010 | Ponzi |
| 7,815,645 B2 | 10/2010 | Haines |
| 7,815,681 B2 | 10/2010 | Ferguson |
| 7,828,853 B2 | 11/2010 | Ek et al. |
| 7,842,042 B2 | 11/2010 | Reay-Young et al. |
| 7,857,817 B2 | 12/2010 | Tallarida et al. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,914,545 B2 | 3/2011 | Ek |
| 7,931,683 B2 | 4/2011 | Weber et al. |
| 7,951,163 B2 | 5/2011 | Ek |
| 7,951,204 B2 | 5/2011 | Chambat et al. |
| 7,955,382 B2 | 6/2011 | Flanagan et al. |
| 7,959,636 B2 | 6/2011 | Schmieding |
| 7,959,650 B2 | 6/2011 | Kaiser et al. |
| 7,959,681 B2 | 6/2011 | Lavi |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,114,163 B2 | 2/2012 | Berelsman et al. |
| 8,137,406 B2 | 3/2012 | Novak et al. |
| 8,137,407 B2 | 3/2012 | Todd et al. |

(56) References Cited

U.S. PATENT DOCUMENTS

| | | |
|---|---|---|
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,157,867 B2 | 4/2012 | Goble et al. |
| 8,162,947 B2 | 4/2012 | Dreyfuss |
| 8,163,027 B2 | 4/2012 | Rhodes et al. |
| 8,167,951 B2 | 5/2012 | Ammann et al. |
| 8,177,738 B2 | 5/2012 | Schmieding et al. |
| 8,177,841 B2 | 5/2012 | Ek |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,267,977 B2 | 9/2012 | Roth |
| 8,298,247 B2 | 10/2012 | Sterrett et al. |
| 8,298,284 B2 | 10/2012 | Cassani |
| 8,303,830 B2 | 11/2012 | Tong et al. |
| 8,308,662 B2 | 11/2012 | Lo |
| 8,308,732 B2 | 11/2012 | Millett et al. |
| 8,308,781 B2 | 11/2012 | Wilson et al. |
| 8,317,870 B2 | 11/2012 | Wagner et al. |
| 8,323,347 B2 | 12/2012 | Guederian et al. |
| 8,328,716 B2 | 12/2012 | Schmieding et al. |
| 8,333,774 B2 | 12/2012 | Morrison |
| 8,343,186 B2 | 1/2013 | Dreyfuss et al. |
| 8,348,960 B2 | 1/2013 | Michel et al. |
| 8,348,975 B2 | 1/2013 | Dreyfuss |
| 8,353,915 B2 | 1/2013 | Helenbolt et al. |
| 8,361,159 B2 | 1/2013 | Ek |
| 8,377,068 B2 | 2/2013 | Aker et al. |
| 8,382,789 B2 | 2/2013 | Weber et al. |
| 8,382,810 B2 | 2/2013 | Peterson et al. |
| 8,388,624 B2 | 3/2013 | Ek et al. |
| 8,398,678 B2 | 3/2013 | Baker et al. |
| 8,409,209 B2 | 4/2013 | Ammann et al. |
| 8,409,250 B2 | 4/2013 | Schmieding et al. |
| 8,414,908 B2 | 4/2013 | Jin et al. |
| 8,419,794 B2 | 4/2013 | ElAttrache et al. |
| 8,425,554 B2 | 4/2013 | Denove et al. |
| 8,430,909 B2 | 4/2013 | Dreyfuss |
| 8,435,272 B2 | 5/2013 | Dougherty et al. |
| 8,439,976 B2 | 5/2013 | Albertorio et al. |
| 8,444,680 B2 | 5/2013 | Dooney, Jr. et al. |
| 8,460,317 B2 | 6/2013 | Merves |
| 8,460,318 B2 | 6/2013 | Murray et al. |
| 8,460,350 B2 | 6/2013 | Albertorio et al. |
| 8,460,379 B2 | 6/2013 | Albertorio et al. |
| 8,470,047 B2 | 6/2013 | Hazebrouck et al. |
| 8,475,536 B2 | 7/2013 | Tong et al. |
| 8,486,072 B2 | 7/2013 | Haininger |
| 8,496,662 B2 | 7/2013 | Novak et al. |
| 8,506,573 B2 | 8/2013 | Dreyfuss et al. |
| 8,512,376 B2 | 8/2013 | Thornes |
| 8,512,411 B2 | 8/2013 | Sluss et al. |
| 8,523,872 B2 | 9/2013 | Ek |
| 8,535,330 B2 | 9/2013 | Sherman et al. |
| 8,535,703 B2 | 9/2013 | Schmieding et al. |
| 8,540,717 B2 | 9/2013 | Tallarida et al. |
| 8,540,777 B2 | 9/2013 | Ammann et al. |
| 8,540,778 B2 | 9/2013 | Rhodes et al. |
| 8,551,101 B2 | 10/2013 | Kuczynski |
| 8,579,940 B2 | 11/2013 | Dreyfuss et al. |
| 8,579,944 B2 | 11/2013 | Holloway et al. |
| 8,591,514 B2 | 11/2013 | Sherman |
| 8,591,523 B2 | 11/2013 | Weber |
| 8,591,544 B2 | 11/2013 | Jolly et al. |
| 8,591,578 B2 | 11/2013 | Albertorio et al. |
| 8,591,592 B2 | 11/2013 | Dreyfuss |
| 8,591,594 B2 | 11/2013 | Parisi et al. |
| 8,597,361 B2 | 12/2013 | Sidebotham et al. |
| 8,623,052 B2 | 1/2014 | Dreyfuss et al. |
| 8,628,573 B2 | 1/2014 | Roller et al. |
| 8,652,139 B2 | 2/2014 | Sterrett et al. |
| 8,663,230 B2 | 3/2014 | Miniaci et al. |
| 8,663,250 B2 | 3/2014 | Weber |
| 8,663,251 B2 | 3/2014 | Burkhart et al. |
| 8,663,279 B2 | 3/2014 | Burkhart et al. |
| 8,663,324 B2 | 3/2014 | Schmieding et al. |
| 8,663,333 B2 | 3/2014 | Metcalfe et al. |
| 8,668,738 B2 | 3/2014 | Schmieding et al. |
| 8,702,715 B2 | 4/2014 | Ammann et al. |
| 8,702,752 B2 | 4/2014 | Schmieding et al. |
| 8,709,052 B2 | 4/2014 | Ammann et al. |
| 8,709,091 B2 | 4/2014 | Rhodes et al. |
| 8,721,722 B2 | 5/2014 | Shah et al. |
| 8,728,131 B2 | 5/2014 | Di Giacomo et al. |
| 8,734,449 B2 | 5/2014 | Schmied et al. |
| 8,753,375 B2 | 6/2014 | Albertorio |
| 8,758,356 B2 | 6/2014 | Fearon et al. |
| 8,764,797 B2 | 7/2014 | Dreyfuss et al. |
| 8,764,807 B2 | 7/2014 | Michel et al. |
| 8,764,839 B2 | 7/2014 | Rhodes et al. |
| 8,771,279 B2 | 7/2014 | Philippon et al. |
| 8,771,351 B2 | 7/2014 | ElAttrache et al. |
| 8,784,423 B2 | 7/2014 | Kowarsch et al. |
| 8,790,401 B2 | 7/2014 | Schmieding et al. |
| 8,801,755 B2 | 8/2014 | Dreyfuss et al. |
| 8,821,541 B2 | 9/2014 | Dreyfuss et al. |
| 8,834,475 B2 | 9/2014 | Ammann et al. |
| 8,834,521 B2 | 9/2014 | Pinto et al. |
| 8,840,619 B2 | 9/2014 | Zajac et al. |
| 8,840,643 B2 | 9/2014 | Dreyfuss |
| 8,852,190 B2 | 10/2014 | Sherman |
| 8,852,201 B2 | 10/2014 | Schmieding et al. |
| 8,858,560 B2 | 10/2014 | Bradley et al. |
| 8,864,827 B2 | 10/2014 | Ek |
| 8,870,877 B2 | 10/2014 | Koogle, Jr. |
| 8,876,900 B2 | 11/2014 | Guederian et al. |
| 8,882,833 B2 | 11/2014 | Saylor et al. |
| 8,882,845 B2 | 11/2014 | Wirth et al. |
| 8,882,847 B2 | 11/2014 | Burdulis, Jr. et al. |
| 8,888,781 B2 | 11/2014 | Sterrett |
| 8,888,785 B2 | 11/2014 | Ammann et al. |
| 8,888,815 B2 | 11/2014 | Holmes, Jr. |
| 8,906,026 B2 | 12/2014 | Ammann et al. |
| 8,911,457 B2 | 12/2014 | Koogle, Jr. et al. |
| 8,920,497 B2 | 12/2014 | Albertorio et al. |
| 8,926,615 B2 | 1/2015 | Ek |
| 8,927,283 B2 | 1/2015 | Komvopoulos et al. |
| 8,939,980 B2 | 1/2015 | Schmieding et al. |
| 8,939,999 B2 | 1/2015 | Sterrett et al. |
| 8,956,369 B2 | 2/2015 | Millett et al. |
| 8,961,538 B2 | 2/2015 | Koogle, Jr. et al. |
| 8,961,575 B2 | 2/2015 | Choinski |
| 8,961,614 B2 | 2/2015 | Ek et al. |
| 8,974,537 B2 | 3/2015 | Dreyfuss |
| 8,986,346 B2 | 3/2015 | Dreyfuss |
| 9,005,245 B2 | 4/2015 | Thornes et al. |
| 9,005,246 B2 | 4/2015 | Burkhart et al. |
| 9,044,343 B2 | 6/2015 | Ek |
| 9,055,955 B2 | 6/2015 | Ek et al. |
| 9,066,716 B2 | 6/2015 | Sikora et al. |
| 9,072,510 B2 | 7/2015 | Thornes et al. |
| 9,072,555 B2 | 7/2015 | Michel |
| 9,078,650 B2 | 7/2015 | Weber |
| 9,078,661 B2 | 7/2015 | Gallo |
| 9,089,363 B2 | 7/2015 | Dooney, Jr. et al. |
| 9,089,433 B2 | 7/2015 | Karnes et al. |
| 9,095,641 B2 | 8/2015 | Albertorio |
| 9,101,366 B2 | 8/2015 | Sterrett et al. |
| 9,101,461 B2 | 8/2015 | Albertorio et al. |
| 9,107,653 B2 | 8/2015 | Sullivan |
| 9,107,676 B2 | 8/2015 | Burkhart et al. |
| 9,113,859 B2 | 8/2015 | Dooney, Jr. et al. |
| 9,113,920 B2 | 8/2015 | Ammann et al. |
| 9,138,223 B2 | 9/2015 | Jolly et al. |

(56) References Cited

U.S. PATENT DOCUMENTS

| | | |
|---|---|---|
| 9,138,237 B2 | 9/2015 | Meade et al. |
| 9,138,241 B2 | 9/2015 | Kuczynski |
| 9,138,246 B2 | 9/2015 | Anderson et al. |
| 9,138,274 B1 | 9/2015 | Biesinger et al. |
| 9,146,576 B2 | 9/2015 | Schmieding et al. |
| 9,168,124 B2 | 10/2015 | Guerra et al. |
| 9,179,907 B2 | 11/2015 | ElAttrache et al. |
| 9,179,950 B2 | 11/2015 | Zajac et al. |
| 9,186,432 B2 | 11/2015 | Mazzocca et al. |
| 9,204,873 B2 | 12/2015 | Tallarida et al. |
| 9,204,874 B2 | 12/2015 | Denove et al. |
| 9,204,960 B2 | 12/2015 | Albertorio et al. |
| 9,211,126 B2 | 12/2015 | Sikora et al. |
| 9,216,017 B2 | 12/2015 | Burkhart |
| 9,216,022 B2 | 12/2015 | Karnes et al. |
| 9,216,090 B2 | 12/2015 | Metcalfe |
| 9,216,091 B2 | 12/2015 | Hardy et al. |
| 9,226,743 B2 | 1/2016 | Dreyfuss et al. |
| 9,226,815 B2 | 1/2016 | Schmieding et al. |
| 9,283,076 B2 | 3/2016 | Sikora et al. |
| 9,295,556 B2 | 3/2016 | Perez, III et al. |
| 9,301,745 B2 | 4/2016 | Dreyfuss |
| 9,301,847 B2 | 4/2016 | Guederian et al. |
| 9,320,512 B2 | 4/2016 | Dooney, Jr. |
| 9,332,979 B2 | 5/2016 | Sullivan et al. |
| 9,333,019 B2 | 5/2016 | Khosla et al. |
| 9,345,471 B2 | 5/2016 | Sullivan |
| 9,351,722 B2 | 5/2016 | Koogle, Jr. et al. |
| 9,351,745 B2 | 5/2016 | Ek et al. |
| 9,357,989 B2 | 6/2016 | Tallarida et al. |
| 9,358,029 B2 | 6/2016 | Sikora et al. |
| 9,364,214 B2 | 6/2016 | Courage |
| 9,381,022 B2 | 7/2016 | Bradley et al. |
| 9,381,053 B2 | 7/2016 | Parsons et al. |
| 9,393,010 B2 | 7/2016 | Murray et al. |
| 9,402,730 B2 | 8/2016 | Lederman et al. |
| 9,421,007 B2 | 8/2016 | Brady et al. |
| 9,421,008 B2 | 8/2016 | Burkhart et al. |
| 9,421,010 B2 | 8/2016 | Dreyfuss |
| 9,421,086 B2 | 8/2016 | Roller et al. |
| 9,421,105 B2 | 8/2016 | Metcalfe et al. |
| 9,451,951 B2 | 9/2016 | Sullivan et al. |
| 9,463,011 B2 | 10/2016 | Dreyfuss et al. |
| 9,468,448 B2 | 10/2016 | Sikora et al. |
| 9,485,475 B2 | 11/2016 | Speier et al. |
| 9,486,207 B2 | 11/2016 | Dooney, Jr. et al. |
| 9,486,317 B2 | 11/2016 | Milano et al. |
| 9,492,200 B2 | 11/2016 | Sikora et al. |
| 9,498,232 B2 | 11/2016 | Perez, III |
| 9,504,462 B2 | 11/2016 | Dooney, Jr. et al. |
| 9,510,840 B2 | 12/2016 | Sikora et al. |
| 9,510,951 B2 | 12/2016 | Bachmaier |
| 9,521,999 B2 | 12/2016 | Dreyfuss et al. |
| 9,526,493 B2 | 12/2016 | Dreyfuss et al. |
| 9,526,510 B2 | 12/2016 | Sterrett |
| 9,549,701 B2 | 1/2017 | Peterson et al. |
| 9,549,726 B2 | 1/2017 | Dreyfuss et al. |
| 9,603,712 B2 | 3/2017 | Bachmaier |
| 9,610,167 B2 | 4/2017 | Hardy et al. |
| 9,615,821 B2 | 4/2017 | Sullivan |
| 9,622,738 B2 | 4/2017 | Dreyfuss et al. |
| 9,622,739 B2 | 4/2017 | Dreyfuss et al. |
| 9,622,775 B2 | 4/2017 | Jolly et al. |
| 9,642,609 B2 | 5/2017 | Holmes, Jr. |
| 9,642,610 B2 | 5/2017 | Albertorio et al. |
| 9,662,126 B2 | 5/2017 | Sikora et al. |
| 9,687,222 B2 | 6/2017 | Dreyfuss et al. |
| 9,687,256 B2 | 6/2017 | Granberry et al. |
| 9,687,338 B2 | 6/2017 | Albertorio et al. |
| 9,693,765 B2 | 7/2017 | Sullivan et al. |
| 9,693,787 B2 | 7/2017 | Ammann et al. |
| 9,706,986 B2 | 7/2017 | ElAttrache et al. |
| 9,707,023 B2 | 7/2017 | Ammann et al. |
| 9,724,138 B2 | 8/2017 | Palmer et al. |
| 9,737,292 B2 | 8/2017 | Sullivan et al. |
| 9,750,850 B2 | 9/2017 | Fonte et al. |
| 9,775,599 B2 | 10/2017 | ElAttrache et al. |
| 9,795,392 B2 | 10/2017 | Zajac |
| 9,801,625 B2 | 10/2017 | Dooney, Jr. et al. |
| 9,801,707 B2 | 10/2017 | Cassani |
| 9,801,726 B2 | 10/2017 | Karnes et al. |
| 9,808,240 B2 | 11/2017 | Parsons et al. |
| 9,814,455 B2 | 11/2017 | Dooney, Jr. et al. |
| 9,814,499 B2 | 11/2017 | Buscaglia et al. |
| 9,833,260 B2 | 12/2017 | Jolly et al. |
| 9,839,462 B2 | 12/2017 | Zajac |
| 9,855,029 B2 | 1/2018 | Sullivan |
| 9,855,036 B2 | 1/2018 | Palmer et al. |
| 9,855,064 B2 | 1/2018 | Albertorio et al. |
| 9,855,132 B2 | 1/2018 | Hoover et al. |
| 9,855,146 B2 | 1/2018 | Schmieding |
| 9,861,357 B2 | 1/2018 | Palmer et al. |
| 9,861,413 B2 | 1/2018 | Palmer et al. |
| 9,861,417 B2 | 1/2018 | Helenbolt et al. |
| 9,861,492 B2 | 1/2018 | Ek |
| 9,867,607 B2 | 1/2018 | Sullivan |
| 9,877,712 B2 | 1/2018 | Provencher et al. |
| 9,877,758 B2 | 1/2018 | Michel |
| 9,888,997 B2 | 2/2018 | Dreyfuss et al. |
| 9,895,177 B2 | 2/2018 | Hientzsch et al. |
| 9,907,655 B2 | 3/2018 | Ingwer et al. |
| 9,907,657 B2 | 3/2018 | Fonte et al. |
| 9,913,640 B2 | 3/2018 | Perez, III |
| 9,918,769 B2 | 3/2018 | Provencher et al. |
| 9,931,115 B2 | 4/2018 | Morgan et al. |
| 9,931,211 B2 | 4/2018 | Ek et al. |
| 9,931,219 B2 | 4/2018 | Sikora et al. |
| 9,962,265 B2 | 5/2018 | Ek et al. |
| 9,974,537 B2 | 5/2018 | Coughlin et al. |
| 9,974,550 B2 | 5/2018 | Seitlinger et al. |
| 9,999,416 B2 | 6/2018 | Kelly et al. |
| 10,045,770 B2 | 8/2018 | Burkhart et al. |
| 10,045,788 B2 | 8/2018 | Sikora et al. |
| 10,052,091 B2 | 8/2018 | Dreyfuss et al. |
| 10,058,322 B2 | 8/2018 | Dooney, Jr. et al. |
| 10,064,983 B2 | 8/2018 | Weber et al. |
| 10,076,321 B2 | 9/2018 | Crane et al. |
| 10,076,322 B1 | 9/2018 | Dreyfuss |
| 10,076,343 B2 | 9/2018 | Ek |
| 10,076,407 B2 | 9/2018 | Albertorio et al. |
| 10,080,557 B1 | 9/2018 | Laviano et al. |
| 10,085,739 B2 | 10/2018 | Dooney, Jr. et al. |
| 10,092,340 B2 | 10/2018 | Choinski et al. |
| 10,111,649 B2 | 10/2018 | Laviano et al. |
| 10,117,657 B2 | 11/2018 | Guederian |
| 10,159,518 B2 | 12/2018 | Holowecky et al. |
| 10,172,606 B2 | 1/2019 | Sullivan et al. |
| 10,172,607 B2 | 1/2019 | Burkhart |
| 10,172,703 B2 | 1/2019 | Adams et al. |
| 10,182,917 B2 | 1/2019 | Zajac |
| 10,188,504 B2 | 1/2019 | Cassani |
| 10,194,899 B2 | 2/2019 | Benavitz et al. |
| 10,206,670 B2 | 2/2019 | Thornes |
| 10,206,694 B2 | 2/2019 | Libby et al. |
| 10,213,219 B2 | 2/2019 | Garlock et al. |
| 10,238,484 B2 | 3/2019 | Albertorio et al. |
| 10,245,016 B2 | 4/2019 | Zajac et al. |
| 10,251,655 B2 | 4/2019 | Sterrett |
| 10,251,656 B2 | 4/2019 | Granberry et al. |
| 10,251,686 B2 | 4/2019 | Zajac et al. |
| 10,258,320 B2 | 4/2019 | Dreyfuss et al. |
| 10,265,060 B2 | 4/2019 | Dooney, Jr. et al. |
| 10,285,801 B2 | 5/2019 | Roller et al. |
| 10,299,841 B2 | 5/2019 | Dunlop et al. |
| 10,363,024 B2 | 7/2019 | Koogle, Jr. et al. |
| 10,398,426 B2 | 9/2019 | Burkhart et al. |
| 10,405,904 B2 | 9/2019 | Hientzsch et al. |
| 10,413,341 B2 | 9/2019 | Chaudot et al. |
| 10,420,597 B2 | 9/2019 | Papangelou et al. |
| 10,448,945 B2 | 10/2019 | Bachmaier et al. |
| 10,456,145 B2 | 10/2019 | Laviano et al. |
| 10,478,200 B2 | 11/2019 | Sikora et al. |
| 10,499,932 B2 | 12/2019 | Koogle, Jr. et al. |
| 10,512,543 B2 | 12/2019 | Ingwer et al. |

(56) References Cited

U.S. PATENT DOCUMENTS

| | | |
|---|---|---|
| 2001/0010023 A1 | 7/2001 | Schwartz et al. |
| 2001/0012967 A1 | 8/2001 | Mosseri |
| 2001/0016775 A1 | 8/2001 | Scarborough et al. |
| 2001/0034526 A1 | 10/2001 | Kuslich et al. |
| 2001/0039455 A1 | 11/2001 | Simon et al. |
| 2001/0053914 A1 | 12/2001 | Landry et al. |
| 2001/0056266 A1 | 12/2001 | Tallarida et al. |
| 2002/0022847 A1 | 2/2002 | Ray, III et al. |
| 2002/0022889 A1 | 2/2002 | Chibrac et al. |
| 2002/0022890 A1 | 2/2002 | Jacobsson et al. |
| 2002/0049444 A1 | 4/2002 | Knox |
| 2002/0055783 A1 | 5/2002 | Tallarida et al. |
| 2002/0082701 A1 | 6/2002 | Zdeblick et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2002/0183760 A1 | 12/2002 | McGovern et al. |
| 2003/0028196 A1 | 2/2003 | Bonutti |
| 2003/0060887 A1 | 3/2003 | Ek |
| 2003/0065332 A1 | 4/2003 | TenHuisen et al. |
| 2003/0065391 A1 | 4/2003 | Re et al. |
| 2003/0083751 A1 | 5/2003 | Tornier |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0144736 A1 | 7/2003 | Sennett |
| 2003/0171756 A1 | 9/2003 | Fallin et al. |
| 2003/0171820 A1 | 9/2003 | Wilshaw et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0204267 A1 | 10/2003 | Hazebrouck et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |
| 2004/0039389 A1 | 2/2004 | West, Jr. et al. |
| 2004/0064190 A1 | 4/2004 | Ball et al. |
| 2004/0082906 A1 | 4/2004 | Tallarida et al. |
| 2004/0083005 A1 | 4/2004 | Jacobsson et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153086 A1 | 8/2004 | Sanford |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0176775 A1 | 9/2004 | Burkus et al. |
| 2004/0186582 A1 | 9/2004 | Yasuda et al. |
| 2004/0193172 A1 | 9/2004 | Ross et al. |
| 2004/0193175 A1 | 9/2004 | Maroney et al. |
| 2004/0193267 A1 | 9/2004 | Jones et al. |
| 2004/0193268 A1 | 9/2004 | Hazebrouck |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210309 A1 | 10/2004 | Denier et al. |
| 2004/0220574 A1 | 11/2004 | Pelo et al. |
| 2004/0230315 A1 | 11/2004 | Ek |
| 2004/0236339 A1 | 11/2004 | Pepper |
| 2004/0254585 A1 | 12/2004 | Whittaker et al. |
| 2004/0260303 A1 | 12/2004 | Carrison |
| 2005/0015092 A1 | 1/2005 | Rathbun et al. |
| 2005/0015153 A1 | 1/2005 | Gobel et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0049716 A1 | 3/2005 | Wagener et al. |
| 2005/0065612 A1 | 3/2005 | Winslow |
| 2005/0071014 A1 | 3/2005 | Barnett et al. |
| 2005/0075642 A1 | 4/2005 | Felt |
| 2005/0085909 A1 | 4/2005 | Eisermann |
| 2005/0090905 A1 | 4/2005 | Hawkins et al. |
| 2005/0107799 A1 | 5/2005 | Graf et al. |
| 2005/0119758 A1 | 6/2005 | Alexander et al. |
| 2005/0143731 A1 | 6/2005 | Justin et al. |
| 2005/0143745 A1 | 6/2005 | Hodorek et al. |
| 2005/0143821 A1 | 6/2005 | Zdeblick et al. |
| 2005/0143831 A1 | 6/2005 | Justin et al. |
| 2005/0149044 A1 | 7/2005 | Justin et al. |
| 2005/0154398 A1 | 7/2005 | Miniaci et al. |
| 2005/0165407 A1 | 7/2005 | Diaz |
| 2005/0165487 A1 | 7/2005 | Muhanna et al. |
| 2005/0177171 A1 | 8/2005 | Wetzler et al. |
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |
| 2005/0234461 A1 | 10/2005 | Burdulis, Jr. et al. |
| 2005/0245932 A1 | 11/2005 | Fanton et al. |
| 2005/0251268 A1 | 11/2005 | Truncale |
| 2005/0273112 A1 | 12/2005 | McNamara |
| 2005/0287187 A1 | 12/2005 | Mansmann |
| 2006/0004461 A1 | 1/2006 | Justin et al. |
| 2006/0009774 A1 | 1/2006 | Goble et al. |
| 2006/0020343 A1 | 1/2006 | Ek |
| 2006/0041261 A1 | 2/2006 | Osypka |
| 2006/0052878 A1 | 3/2006 | Schmieding |
| 2006/0058744 A1 | 3/2006 | Tallarida et al. |
| 2006/0058809 A1 | 3/2006 | Zink et al. |
| 2006/0058883 A1 | 3/2006 | Aram et al. |
| 2006/0069394 A1 | 3/2006 | Weiler et al. |
| 2006/0074430 A1 | 4/2006 | Deffenbaugh et al. |
| 2006/0085006 A1 | 4/2006 | Ek |
| 2006/0085077 A1 | 4/2006 | Cook et al. |
| 2006/0105015 A1 | 5/2006 | Perla et al. |
| 2006/0111787 A1 | 5/2006 | Bailie et al. |
| 2006/0121080 A1 | 6/2006 | Lye et al. |
| 2006/0142772 A1 | 6/2006 | Ralph et al. |
| 2006/0149370 A1 | 7/2006 | Schmieding et al. |
| 2006/0154206 A1 | 7/2006 | Petersson et al. |
| 2006/0167560 A1 | 7/2006 | Heck et al. |
| 2006/0184187 A1 | 8/2006 | Surti |
| 2006/0190002 A1 | 8/2006 | Tallarida |
| 2006/0195112 A1 | 8/2006 | Ek |
| 2006/0217728 A1 | 9/2006 | Chervitz et al. |
| 2006/0229726 A1 | 10/2006 | Ek |
| 2006/0271059 A1 | 11/2006 | Reay-Young et al. |
| 2007/0005143 A1 | 1/2007 | Ek |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093848 A1 | 4/2007 | Harris et al. |
| 2007/0093890 A1 | 4/2007 | Eliasen et al. |
| 2007/0093896 A1 | 4/2007 | Malinin |
| 2007/0118136 A1 | 5/2007 | Ek |
| 2007/0118224 A1 | 5/2007 | Shah et al. |
| 2007/0123921 A1 | 5/2007 | Ek |
| 2007/0134291 A1 | 6/2007 | Ting et al. |
| 2007/0173850 A1 | 7/2007 | Rangaiah et al. |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270711 A1 | 11/2007 | Gil et al. |
| 2007/0270873 A1 | 11/2007 | Flickinger et al. |
| 2007/0282455 A1 | 12/2007 | Luginbuehl et al. |

(56) References Cited

U.S. PATENT DOCUMENTS

| | | |
|---|---|---|
| 2007/0288031 A1 | 12/2007 | Dreyfuss et al. |
| 2007/0299519 A1 | 12/2007 | Schmieding |
| 2007/0299529 A1 | 12/2007 | Rhodes et al. |
| 2008/0004659 A1 | 1/2008 | Burkhart et al. |
| 2008/0015607 A1 | 1/2008 | D'Alessio et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046084 A1 | 2/2008 | Sledge |
| 2008/0071381 A1 | 3/2008 | Buscher et al. |
| 2008/0086139 A1 | 4/2008 | Bourke et al. |
| 2008/0086152 A1 | 4/2008 | McKay et al. |
| 2008/0091271 A1 | 4/2008 | Bonitati et al. |
| 2008/0091272 A1 | 4/2008 | Aram et al. |
| 2008/0097618 A1 | 4/2008 | Baker et al. |
| 2008/0103506 A1 | 5/2008 | Volpi et al. |
| 2008/0114463 A1 | 5/2008 | Auger et al. |
| 2008/0138611 A1 | 6/2008 | Yasuzawa et al. |
| 2008/0154271 A1 | 6/2008 | Berberich et al. |
| 2008/0172125 A1 | 7/2008 | Ek |
| 2008/0177200 A1 | 7/2008 | Ikehara et al. |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0200904 A1 | 8/2008 | Cluff et al. |
| 2008/0208201 A1 | 8/2008 | Moindreau et al. |
| 2008/0243262 A1 | 10/2008 | Lee |
| 2008/0243263 A1 | 10/2008 | Lee et al. |
| 2008/0262500 A1 | 10/2008 | Collazo |
| 2008/0262625 A1 | 10/2008 | Spriano et al. |
| 2008/0275451 A1 | 11/2008 | McAllister et al. |
| 2008/0275512 A1 | 11/2008 | Albertirio et al. |
| 2008/0294168 A1 | 11/2008 | Wieland |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0018581 A1 | 1/2009 | Anderson et al. |
| 2009/0035722 A1 | 2/2009 | Balasundaram et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0088753 A1 | 4/2009 | Aram et al. |
| 2009/0088858 A1 | 4/2009 | Zinger et al. |
| 2009/0105772 A1 | 4/2009 | Seebeck et al. |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216268 A1 | 8/2009 | Panter |
| 2009/0216285 A1 | 8/2009 | Ek et al. |
| 2009/0220561 A1 | 9/2009 | Jin et al. |
| 2009/0222012 A1 | 9/2009 | Karnes et al. |
| 2009/0228031 A1 | 9/2009 | Ritter et al. |
| 2009/0228105 A1 | 9/2009 | Son et al. |
| 2009/0234452 A1 | 9/2009 | Steiner et al. |
| 2009/0254094 A1 | 10/2009 | Knapp et al. |
| 2009/0264889 A1 | 10/2009 | Long et al. |
| 2009/0264928 A1 | 10/2009 | Blain |
| 2009/0275950 A1 | 11/2009 | Sterrett et al. |
| 2009/0276052 A1 | 11/2009 | Regala et al. |
| 2009/0283701 A1 | 11/2009 | Ogawa |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0057197 A1 | 3/2010 | Weber et al. |
| 2010/0069958 A1 | 3/2010 | Sullivan et al. |
| 2010/0082035 A1 | 4/2010 | Keefer |
| 2010/0087829 A1 | 4/2010 | Metzger et al. |
| 2010/0092535 A1 | 4/2010 | Cook et al. |
| 2010/0112519 A1 | 5/2010 | Hall et al. |
| 2010/0136289 A1 | 6/2010 | Extrand et al. |
| 2010/0168505 A1 | 7/2010 | Inman et al. |
| 2010/0168854 A1 | 7/2010 | Luers et al. |
| 2010/0185294 A1 | 7/2010 | Ek |
| 2010/0191342 A1 | 7/2010 | Byrd et al. |
| 2010/0217315 A1 | 8/2010 | Jolly et al. |
| 2010/0227372 A1 | 9/2010 | Bilek et al. |
| 2010/0241236 A1 | 9/2010 | Katrana et al. |
| 2010/0249930 A1 | 9/2010 | Myers |
| 2010/0249935 A1 | 9/2010 | Slivka et al. |
| 2010/0249942 A1 | 9/2010 | Goswami et al. |
| 2010/0256645 A1 | 10/2010 | Zajac et al. |
| 2010/0256758 A1 | 10/2010 | Gordon et al. |
| 2010/0268227 A1 | 10/2010 | Tong et al. |
| 2010/0268238 A1 | 10/2010 | Sikora et al. |
| 2010/0268330 A1 | 10/2010 | Tong et al. |
| 2010/0268346 A1 | 10/2010 | Tong et al. |
| 2010/0268347 A1 | 10/2010 | Tong et al. |
| 2011/0009964 A1 | 1/2011 | Schwartz et al. |
| 2011/0035012 A1 | 2/2011 | Linares |
| 2011/0059312 A1 | 3/2011 | Howling et al. |
| 2011/0066242 A1 | 3/2011 | Lu et al. |
| 2011/0071641 A1 | 3/2011 | Ek et al. |
| 2011/0085968 A1 | 4/2011 | Jin et al. |
| 2011/0087280 A1 | 4/2011 | Albertorio |
| 2011/0093085 A1 | 4/2011 | Morton |
| 2011/0106271 A1 | 5/2011 | Regala et al. |
| 2011/0123951 A1 | 5/2011 | Lomicka |
| 2011/0125263 A1 | 5/2011 | Webster et al. |
| 2011/0125277 A1 | 5/2011 | Nygren et al. |
| 2011/0152869 A1 | 6/2011 | Ek et al. |
| 2011/0153023 A1 | 6/2011 | Deffenbaugh et al. |
| 2011/0159070 A1 | 6/2011 | Jin et al. |
| 2011/0190902 A1 | 8/2011 | Tong et al. |
| 2011/0196367 A1 | 8/2011 | Gallo |
| 2011/0213375 A1 | 9/2011 | Sikora et al. |
| 2011/0236435 A1 | 9/2011 | Biris |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0022656 A1 | 1/2012 | Lavi |
| 2012/0027837 A1 | 2/2012 | DeMuth et al. |
| 2012/0051489 A1 | 3/2012 | Varanasi et al. |
| 2012/0058328 A1 | 3/2012 | Tourvieille et al. |
| 2012/0059418 A1 | 3/2012 | Denham et al. |
| 2012/0065732 A1 | 3/2012 | Roller et al. |
| 2012/0065734 A1 | 3/2012 | Barrett et al. |
| 2012/0109136 A1 | 5/2012 | Bourque et al. |
| 2012/0109222 A1 | 5/2012 | Goel et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0128666 A1 | 5/2012 | Pébay et al. |
| 2012/0150225 A1 | 6/2012 | Burkart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0214128 A1 | 8/2012 | Collins et al. |
| 2012/0215310 A1 | 8/2012 | Sharp et al. |
| 2012/0221111 A1 | 8/2012 | Burkhead, Jr. et al. |
| 2012/0253467 A1 | 10/2012 | Frankle |
| 2012/0265298 A1 | 10/2012 | Schmieding et al. |
| 2012/0323338 A1* | 12/2012 | Vanasse ............ A61F 2/42 623/21.15 |
| 2012/0330357 A1 | 12/2012 | Thal |
| 2013/0006374 A1 | 1/2013 | Le Couedic et al. |
| 2013/0022943 A1 | 1/2013 | Collins et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |

(56) References Cited

U.S. PATENT DOCUMENTS

| | | |
|---|---|---|
| 2013/0103104 A1 | 4/2013 | Krupp et al. |
| 2013/0110165 A1 | 5/2013 | Burkhart et al. |
| 2013/0138108 A1 | 5/2013 | Dryfuss et al. |
| 2013/0138150 A1 | 5/2013 | Baker et al. |
| 2013/0150885 A1 | 6/2013 | Dreyfuss |
| 2013/0150975 A1 | 6/2013 | Iannotti et al. |
| 2013/0165954 A1 | 6/2013 | Dreyfuss et al. |
| 2013/0165972 A1 | 6/2013 | Sullivan |
| 2013/0178871 A1 | 7/2013 | Koogle, Jr. et al. |
| 2013/0184818 A1 | 7/2013 | Coughlin et al. |
| 2013/0190819 A1 | 7/2013 | Norton |
| 2013/0190885 A1 | 7/2013 | Ammann et al. |
| 2013/0204257 A1 | 8/2013 | Zajac |
| 2013/0204259 A1 | 8/2013 | Zajac |
| 2013/0205936 A1 | 8/2013 | Schmieding et al. |
| 2013/0218176 A1 | 8/2013 | Denove et al. |
| 2013/0218286 A1 | 8/2013 | Stahl Wernersson et al. |
| 2013/0237987 A1 | 9/2013 | Graham |
| 2013/0238099 A1 | 9/2013 | Hardy et al. |
| 2013/0245775 A1 | 9/2013 | Metcalfe |
| 2013/0268073 A1 | 10/2013 | Albertorio et al. |
| 2013/0282129 A1 | 10/2013 | Phipps |
| 2013/0289570 A1 | 10/2013 | Chao |
| 2013/0304209 A1 | 11/2013 | Schmieding et al. |
| 2013/0331886 A1 | 12/2013 | Thornes |
| 2013/0338722 A1 | 12/2013 | Yalizis |
| 2013/0338792 A1 | 12/2013 | Schmieding et al. |
| 2013/0344600 A1 | 12/2013 | Jin et al. |
| 2013/0345747 A1 | 12/2013 | Dreyfuss |
| 2013/0345748 A1 | 12/2013 | Dreyfuss |
| 2014/0012267 A1 | 1/2014 | Skiora et al. |
| 2014/0012389 A1 | 1/2014 | Ek |
| 2014/0052178 A1 | 2/2014 | Dooney, Jr. |
| 2014/0052179 A1 | 2/2014 | Dreyfuss et al. |
| 2014/0066933 A1 | 3/2014 | Ek et al. |
| 2014/0074164 A1 | 3/2014 | Dreyfuss et al. |
| 2014/0074239 A1 | 3/2014 | Albertorio et al. |
| 2014/0079921 A1 | 3/2014 | De Volder |
| 2014/0081273 A1 | 3/2014 | Sherman |
| 2014/0081399 A1 | 3/2014 | Roller et al. |
| 2014/0088601 A1 | 3/2014 | Kuczynski |
| 2014/0088602 A1 | 3/2014 | Ammann et al. |
| 2014/0114322 A1 | 4/2014 | Perez, III |
| 2014/0114367 A1 | 4/2014 | Jolly et al. |
| 2014/0121700 A1 | 5/2014 | Dreyruss et al. |
| 2014/0121701 A1 | 5/2014 | Dreyruss et al. |
| 2014/0128889 A1 | 5/2014 | Sullivan et al. |
| 2014/0128915 A1 | 5/2014 | Dreyfuss et al. |
| 2014/0128921 A1 | 5/2014 | Parsons et al. |
| 2014/0155902 A1 | 6/2014 | Sikora et al. |
| 2014/0188232 A1 | 7/2014 | Metcalfe et al. |
| 2014/0194880 A1 | 7/2014 | Schmieding et al. |
| 2014/0228849 A1 | 8/2014 | Sterrett et al. |
| 2014/0236306 A1 | 8/2014 | Karnes et al. |
| 2014/0243439 A1 | 8/2014 | Papangelou et al. |
| 2014/0243891 A1 | 8/2014 | Schmieding et al. |
| 2014/0243892 A1 | 8/2014 | Choinski |
| 2014/0243976 A1 | 8/2014 | Schmieding et al. |
| 2014/0257297 A1 | 9/2014 | Koogle, Jr. et al. |
| 2014/0257299 A1 | 9/2014 | Berelsman et al. |
| 2014/0257384 A1 | 9/2014 | Dreyfuss et al. |
| 2014/0276841 A1 | 9/2014 | Albertorio et al. |
| 2014/0276990 A1 | 9/2014 | Perez, III |
| 2014/0277020 A1 | 9/2014 | Koogle et al. |
| 2014/0277121 A1 | 9/2014 | Pilgeram et al. |
| 2014/0277134 A1 | 9/2014 | ElAttrache et al. |
| 2014/0277181 A1 | 9/2014 | Garlock |
| 2014/0277186 A1 | 9/2014 | Granberry et al. |
| 2014/0277214 A1 | 9/2014 | Helenbolt et al. |
| 2014/0277448 A1 | 9/2014 | Guerra et al. |
| 2014/0288657 A1 | 9/2014 | Lederman et al. |
| 2014/0309689 A1 | 10/2014 | Sikora et al. |
| 2014/0324167 A1 | 10/2014 | Schmieding et al. |
| 2014/0335145 A1 | 11/2014 | Jin et al. |
| 2014/0350688 A1 | 11/2014 | Michel et al. |
| 2015/0073424 A1 | 3/2015 | Couture et al. |
| 2015/0134066 A1 | 5/2015 | Bachmaier |
| 2015/0142052 A1 | 5/2015 | Koogle, Jr. et al. |
| 2015/0157462 A1 | 6/2015 | Ek et al. |
| 2015/0164648 A1 | 6/2015 | Lizak et al. |
| 2015/0201951 A1 | 7/2015 | Bradley et al. |
| 2015/0216541 A1 | 8/2015 | Schmieding et al. |
| 2015/0245831 A1 | 9/2015 | Sullivan |
| 2015/0250472 A1 | 9/2015 | Ek et al. |
| 2015/0250475 A1 | 9/2015 | Ek |
| 2015/0250594 A1 | 9/2015 | Ek |
| 2015/0250602 A1 | 9/2015 | Sikora et al. |
| 2015/0265328 A1 | 9/2015 | Viola |
| 2015/0313586 A1 | 11/2015 | Burkhart et al. |
| 2016/0022374 A1 | 1/2016 | Haider et al. |
| 2016/0030035 A1 | 2/2016 | Zajac et al. |
| 2016/0051268 A1 | 2/2016 | Seitlinger et al. |
| 2016/0106444 A1 | 4/2016 | Ek |
| 2016/0151060 A1 | 6/2016 | Albertorio et al. |
| 2016/0151119 A1 | 6/2016 | Michel et al. |
| 2016/0287243 A1 | 10/2016 | Benedict et al. |
| 2016/0287266 A1 | 10/2016 | Sikora et al. |
| 2016/0310132 A1 | 10/2016 | Meislin et al. |
| 2016/0331404 A1 | 11/2016 | Jolly et al. |
| 2016/0354197 A1 | 12/2016 | Roller et al. |
| 2017/0056180 A1 | 3/2017 | Schmieding |
| 2017/0119528 A1 | 5/2017 | Ek et al. |
| 2017/0128085 A1 | 5/2017 | Sikora et al. |
| 2017/0209196 A1 | 7/2017 | Zajac et al. |
| 2017/0215935 A1 | 8/2017 | Taft |
| 2017/0239696 A1 | 8/2017 | Weber |
| 2017/0252147 A1 | 9/2017 | Albertorio et al. |
| 2017/0252521 A1 | 9/2017 | Guerra et al. |
| 2017/0281200 A1 | 10/2017 | Sikora et al. |
| 2017/0296328 A1 | 10/2017 | Albertorio et al. |
| 2017/0311983 A1 | 11/2017 | Sikora et al. |
| 2017/0333020 A1 | 11/2017 | Laviano et al. |
| 2018/0055507 A1 | 3/2018 | Bachmaier et al. |
| 2018/0085104 A1 | 3/2018 | Schmieding et al. |
| 2018/0085109 A1 | 3/2018 | Petry et al. |
| 2018/0103963 A1 | 4/2018 | Bradley et al. |
| 2018/0116682 A1 | 5/2018 | Albertorio et al. |
| 2018/0132869 A1 | 5/2018 | Sikora et al. |
| 2018/0154041 A1 | 6/2018 | Altschuler et al. |
| 2018/0344447 A1 | 12/2018 | Albertorio et al. |
| 2019/0021719 A1 | 1/2019 | Dooney et al. |
| 2019/0029836 A1 | 1/2019 | Ek |
| 2019/0038426 A1 | 2/2019 | Ek |
| 2019/0059910 A1 | 2/2019 | Adams et al. |
| 2019/0105160 A1 | 4/2019 | Ek et al. |
| 2019/0105165 A1 | 4/2019 | Sikora et al. |
| 2019/0105166 A1 | 4/2019 | Ek et al. |
| 2019/0239902 A1 | 8/2019 | Sikora et al. |
| 2019/0350578 A1 | 11/2019 | Petry et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| DE | 19505083 | 11/1995 |
| DE | 102004053606 | 5/2006 |
| DE | 112013003358 | 3/2015 |
| EP | 0240004 | 10/1987 |
| EP | 0241240 | 10/1987 |
| EP | 0290736 | 11/1988 |
| EP | 0350780 | 1/1990 |
| EP | 0485678 | 5/1992 |
| EP | 0327387 | 9/1992 |
| EP | 0505634 | 9/1992 |

(56) References Cited

FOREIGN PATENT DOCUMENTS

| | | |
|---|---|---|
| EP | 0736292 | 10/1996 |
| EP | 0903127 | 3/1999 |
| EP | 3903125 | 3/1999 |
| EP | 0993812 | 4/2000 |
| EP | 0661023 | 8/2001 |
| EP | 1374782 | 1/2004 |
| EP | 1426013 | 9/2004 |
| EP | 1870060 | 12/2007 |
| EP | 1927328 | 6/2008 |
| EP | 1278460 | 4/2009 |
| EP | 2062541 | 5/2009 |
| EP | 2455002 | 5/2012 |
| EP | 2314257 | 2/2013 |
| EP | 2572650 | 3/2013 |
| EP | 2595534 | 6/2014 |
| EP | 2804565 | 10/2014 |
| EP | 2481368 | 12/2014 |
| EP | 2986232 | 2/2016 |
| EP | 2 400 930 | 12/2017 |
| EP | 2986232 | 11/2018 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2964035 | 10/1999 |
| JP | 2001525210 | 12/2001 |
| JP | 2002291779 | 10/2002 |
| JP | 2003534096 | 11/2003 |
| WO | 198803781 | 6/1988 |
| WO | 8909578 | 10/1989 |
| WO | 9409730 | 5/1994 |
| WO | 9427507 | 12/1994 |
| WO | 9624304 | 8/1996 |
| WO | 1997022306 | 6/1997 |
| WO | 199725006 | 7/1997 |
| WO | 9920192 | 4/1999 |
| WO | 0013597 | 3/2000 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2004100839 | 11/2004 |
| WO | 2005051231 | 6/2005 |
| WO | 2006004885 | 1/2006 |
| WO | 2006074321 | 7/2006 |
| WO | 2006091686 | 8/2006 |
| WO | 2010135156 | 11/2010 |
| WO | 2012003548 | 1/2012 |
| WO | 2012021857 | 2/2012 |
| WO | 2012058349 | 5/2012 |
| WO | 2013152102 | 10/2013 |
| WO | 2014008126 | 1/2014 |
| WO | 2014172347 | 10/2014 |
| WO | 2016154393 | 9/2016 |
| WO | 2019028344 | 2/2019 |

OTHER PUBLICATIONS

U.S. Applicant Initiated Interview Summary dated May 15, 2013 issued in U.S. Appl. No. 12/762,920, 3 pages.
European Office Action dated May 15, 2013 issued in European Patent Application No. 05 763 817.3, 4 pages.
U.S. Final Office Action dated Jun. 5, 2013 issued in U.S. Appl. No. 12/942,923, 26 pages.
U.S. Final Office Action dated Jun. 24, 2013 issued in U.S. Appl. No. 13/042,382, 28 pages.
U.S. Notice of Allowance dated Jun. 14, 2013 issued in U.S. Appl. No. 13/043,430, 10 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.
Corrected Notice of Allowability dated Sep. 10, 2013 issued in U.S. Appl. No. 13/043,430, 7 pages.
Decision to Grant dated Sep. 19, 2013 issued in European Patent Application No. 07862736.1, 1 page.
U.S. Office Action dated Oct. 8, 2013 issued in U.S. Appl. No. 13/438,095, 8 pages.
International Search Report and Written Opinion dated Oct. 22, 2013 issued in PCT International Patent Application No. PCT/US2013/048569, 15 pages.
Notice of Allowance dated Oct. 30, 2013 issued in U.S. Appl. No. 13/037,998, 28 pages.
U.S. Final Office Action dated Nov. 29, 2013 issued in U.S. Appl. No. 12/762,920, 9 pages.
U.S. Final Office Action dated Dec. 5, 2013 issued in U.S. Appl. No. 13/470,678, 8 pages.
U.S. Office Action dated Dec. 12, 2013 issued in U.S. Appl. No. 12/979,992, 12 pages.
U.S. Office Action dated Dec. 17, 2013 issued in U.S. Appl. No. 12/001,473, 21 pages.
U.S. Office Action dated Feb. 5, 2014, issued in U.S. Appl. No. 13/438,095, 9 pages.
U.S. Office Action dated Feb. 7, 2014, issued in U.S. Appl. No. 13/075,006, 9 pages.
Australian Examination Report dated Feb. 7, 2014, issued in Australian Patent Application No. 2010236182, 3 pages.
Australian Examination Report dated Feb. 14, 2014, issued in Australian Patent Application No. 2011222404, 3 pages.
European Extended Search Report dated Feb. 24, 2014, issue in European Patent Application No. 09716273.9, 7 pages.
Australian Examination Report dated Feb. 28, 2014, issued in Australian Patent Application No. 2010217907, 3 pages.
U.S. Final Office Action dated Mar. 20, 2014 in U.S. Appl. No. 12/711,039, 17 pages.
European Examination Report dated Mar. 20, 2014, issued in European Patent Application No. 12 002 103.5, 3 pages.
U.S. Office Action dated Mar. 21, 2014, issued in U.S. Appl. No. 12/942,923, 6 pages.
U.S. Notice of Allowance dated Apr. 1, 2014 issued in U.S. Appl. No. 13/470,678, 7 pages.
Australian Examination Report dated Apr. 3, 2014, issued in Australian Patent Application No. 2010217907, 3 pages.
U.S. Office Action dated Aug. 13, 2014, issued in U.S. Appl. No. 12/762,948, 12 pages.
U.S. Notice of Allowance dated Aug. 21, 2014, issued in U.S. Appl. No. 13/075,006, 5 pages.

(56) References Cited

OTHER PUBLICATIONS

U.S. Office Action dated Sep. 18, 2014, issued in U.S. Appl. No. 13/785,867, 8 pages.
U.S. Notice of Allowance dated Oct. 6, 2014, issued in U.S. Appl. No. 12/942,923, 5 pages.
U.S. Office Action issued in U.S. Appl. No. 13/438,095, dated Nov. 4, 2014, 11 pages.
International Search Report and Written Opinion issued in PCT Patent Application Serial No. PCT/US14/34157, dated Nov. 4, 2014, 12 pages.
European Extended Search Report issued in European Patent Application Serial No. 10765332.1, dated Nov. 10, 2014, 6 pages.
U.S. Office Action issued in U.S. Appl. No. 12/711,039, dated Nov. 10, 2014, 10 pages.
European Extended Search Report issued in European Patent Application Serial No. 10746863.9, dated Nov. 13, 2014, 5 pages.
European Decision to Grant issued in European Patent Application Serial No. 12002103.5, dated Nov. 20, 2014, 1 page.
European Office Action issued in European Patent Application No. 08 729 178.7, dated Nov. 25, 2014, 4 pages.
U.S. Notice of Allowance issued in U.S. Appl. No. 13/037,929, dated Dec. 11, 2014, 5 pages.
International Preliminary Report on Patentability dated Jan. 15, 2015, issued in PCT Patent Application No. PCT/US2013/048569, 9 pages.
Notice of Allowance dated Jan. 21, 2015, issued in U.S. Appl. No. 13/752,858, 7 pages.
Notice of Allowability dated Feb. 19, 2015, issued in U.S. Appl. No. 13/037,929, 2 pages.
U.S. Office Action dated Feb. 19, 2015, issued in U.S. Appl. No. 14/035,061, 6 pages.
Notice of Allowance dated Feb. 25, 2015, issued in U.S. Appl. No. 13/436,188, 8 pages.
Canadian Office Action dated Feb. 27, 2015 issued in Canadian Patent Application Serial No. 2,407,440, 7 pages.
Office Action dated Mar. 3, 2015, issued in U.S. Appl. No. 12/979,992, 11 pages.
U.S. Office Action dated Apr. 29, 2014, issued in U.S. Appl. No. 13/037,929, 11 pages.
U.S. Office Action dated May 19, 2014, issued in U.S. Appl. No. 13/436,188, 10 pages.
U.S. Office Action dated May 28 2014, issued in U.S. Appl. No. 13/752,858, 8 pages.
U.S. Office Action dated Jun. 4, 2014, issued in U.S. Appl. No. 12/762,920, 10 pages.
Notice of Allowance dated Jun. 19, 2014, issued in U.S. Appl. No. 13/470,678, 5 pages.
Intent to Grant dated Jun. 27, 2014, issued in European Patent Application No. 12 002 103.5, 6 pages.
U.S. Office Action dated Jul. 7, 2014, issued in U.S. Appl. No. 12/979,992, 6 pages.
U.S. Office Action dated Jul. 7, 2014, issued in U.S. Appl. No. 12/001,473, 15 pages.
Partial supplementary European search report dated Mar. 25, 2015, issued in EP Patent Application No. 11751521.3, 6 pages.
U.S. Examiner interview summary dated Apr. 8, 2015, issued in U.S. Appl. No. 12/001,473, 4 pages.
U.S. Final Office Action dated Apr. 16, 2015, issued in U.S. Appl. No. 12/762,920, 15 pages.
U.S. Supplemental Notice of Allowance dated Apr. 21, 2015, issued in U.S. Appl. No. 13/436,188, 6 pages.
U.S. Final Office Action dated Apr. 28, 2015, issued in U.S. Appl. No. 13/785,867, 8 pages.
U.S. Office Action dated May 1, 2015, issued in U.S. Appl. No. 14/133,943, 25 pages.
U.S. Final Office Action dated May 22, 2015, issued in U.S. Appl. No. 13/438,095, 7 pages.
U.S. Final Office Action dated Jun. 2, 2015, issued in U.S. Appl. No. 12/001,473, 18 pages.
U.S. Office Action dated Jun. 25, 2015, issued in U.S. Appl. No. 12/711,039, 10 pages.
U.S. Final Office Action dated Jul. 7, 2015, issued in U.S. Appl. No. 12/762,948, 15 pages.
Intent to Grant dated Jul. 8, 2015, issued in European Patent Application No. 08 729 178.7, 7 pages.
Notice of Allowance dated Jul. 31, 2015, issued in U.S. Appl. No. 13/438,095, 8 pages.
Extended Search Report dated Sep. 9, 2015, issued in European Patent Application No. 11751521.3, 13 pages.
U.S. Final Office Action dated Sep. 17, 2015, issued in U.S. Appl. No. 14/035,061, 10 pages.
International Preliminary Report on Patentability dated Oct. 29, 2015, issued in PCT Patent Application No. PCT/US2014/034157, 5 pages.
European Examination Report dated Oct. 28, 2015, issued in European Patent Application No. 05 763 817.3, 4 pages.
U.S. Notice of Allowance dated Oct. 30, 2015, issued in U.S. Appl. No. 12/762,920, 8 pages.
Partial Supplementary European Search Report dated Nov. 5, 2015, issued in European Patent Application No. 12860168.9, 6 pages.
U.S. Office Action dated Nov. 17, 2015, issued in U.S. Appl. No. 13/930,737, 9 pages.
U.S. Office Action dated Nov. 25, 2015, issued in U.S. Appl. No. 13/723,902, 13 pages.
U.S. Office Action dated Nov. 25, 2015, issued in U.S. Appl. No. 13/863,917, 12 pages.
European Examination Report dated Dec. 7, 2015, issued in European Patent Application No. 10 765 332.1, 4 pages.
U.S. Office Action dated Dec. 8, 2015, issued in U.S. Appl. No. 13/796,675, 16 pages.
European Decision to Grant dated Dec. 17, 2015, issued in European Patent Application No. 08729178.7, 2 pages.
European Examination Report dated Jul. 22, 2015, issued in European Patent Application No. 09 002 088.4, 4 pages.
U.S. Office Action dated Jan. 21, 2016, issued in U.S. Appl. No. 12/762,948, 14 pages.
U.S. Final Office Action dated Jan. 21, 2016, issued in U.S. Appl. No. 14/133,943, 27 pages.
U.S. Notice of Allowance dated Feb. 8, 2016, issued in U.S. Appl. No. 13/785,867, 8 pages.
U.S. Notice of Allowance dated Feb. 12, 2016, issued in U.S. Appl. No. 12/001,473, 14 pages.
Canadian Office Action dated Feb. 15, 2016, issued in Canadian Patent Application No. 2,407,440, 3 pages.
U.S. Notice of Allowability dated Feb. 17, 2016, issued in U.S. Appl. No. 13/785,867, 4 pages.
U.S. Notice of Allowance dated Feb. 17, 2016, issued in U.S. Appl. No. 12/979,992, 5 pages.
U.S. Final Office Action dated Feb. 25, 2016, issued in U.S. Appl. No. 12/711,039, 7 pages.
European Extended Search Report dated Feb. 29, 2016, issued in European Patent Application No. 12860168.9, 11 pages.
Canadian Examiner Requisition dated Mar. 10, 2016, issued in Canadian Patent Application No. 2,759,027, 3 pages.
European Examination Report dated Mar. 21, 2016, issued in European Patent Application No. 10 746 863.9, 3 pages.
U.S. Office Action dated Mar. 22, 2016, issued in U.S. Appl. No. 14/640,602, 8 pages.
U.S. Office Action dated Jun. 2, 2016, issued in U.S. Appl. No. 14/035,061, 9 pages.
U.S. Notice of Allowance dated Jun. 7, 2016, issued in U.S. Appl. No. 13/930,737, 5 pages.
International Search Report and Written Opinion dated, Jun. 10, 2016, issued in PCT Patent Application No. PCT/US2016/023930, 13 pages.
U.S. Notice of Allowance dated Jun. 29, 2016, issued in U.S. Appl. No. 13/863,917, 9 pages.
U.S. Final Office Action dated Jul. 6, 2016, issued in U.S. Patent Application No. 13/723,902, 15 pages.
Canadian Office Action dated Jan. 9, 2017, issued in Canadian Patent Application No. 2,759,027, 3 pages.

(56) References Cited

OTHER PUBLICATIONS

Canadian Office Action dated Mar. 22, 2017, issued in Canadian Patent Application No. 2,407,440, 7 pages.
U.S. Notice of Allowance dated Apr. 14, 2017, issued in U.S. Appl. No. 14/640,602, 7 pages.
U.S. Office Action dated Apr. 28, 2017, issued in U.S. Appl. No. 15/153,113, 11 pages.
U.S. Final Office Action dated May 9, 2017, issued in U.S. Appl. No. 14/640,529, 15 pages.
U.S. Final Office Action dated Jun. 15, 2017, issued in U.S. Appl. No. 14/640,774, 10 pages.
Official Communication dated Jun. 21, 2016, issued in European Patent Application No. 11 751 521.3, 3 pages.
Final Office Action dated Jul. 19, 2016, issued in U.S. Appl. No. 13/796,675, 17 pages.
Official Communication dated Aug. 23, 2016, issued in European Patent Application No. 10 765 332.1, 4 pages.
Office Action dated Sep. 8, 2016, issued in U.S. Appl. No. 14/640,529, 15 pages.
Office Action dated Sep. 20, 2016, issued in U.S. Appl. No. 14/133,943, 24 pages.
Final Office Action dated Sep. 30, 2016, issued in U.S. Appl. No. 14/640,602, 5 pages.
Office Action dated Oct. 10, 2016, issued in European Patent Application No. 10 746 863.9, 4 pages.
Extended Search Report dated Nov. 16, 2016, issued in European Patent Application No. 14785702.3, 7 pages.
Office Action dated Nov. 22, 2016, issued in U.S. Appl. No. 14/640,774, 10 pages.
Office Action dated Nov. 24, 2016, issued in European Patent Application No. 12 860 168.9, 4 pages.
Office Action dated Dec. 1, 2016, issued in European Patent Application No. 05 763 817.3, 3 pages.
Notice of Allowance dated Jan. 27, 2017, issued in U.S. Appl. No. 12/762,948, 5 pages.
Office Action dated Jan. 27, 2017, issued in U.S. Appl. No. 14/035,061, 9 pages.
Office Action dated Feb. 7, 2017, issued in U.S. Appl. No. 13/723,902, 16 pages.
Office Action dated Feb. 22, 2017, issued in U.S. Appl. No. 13/796,675, 19 pages.
Final Office Action dated Mar. 28, 2017, issued in U.S. Appl. No. 14/133,943, 29 pages.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/28284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
McCarty, III., et al., "Nonarthroplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.

(56) References Cited

OTHER PUBLICATIONS

Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Jäger, et al., "Partial hemi-resurfacing of the hip joint—a new approach to treat local osteochondral defects?" Biomed Tech 2006; 51:371-376 (2006).
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 12 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Notice of Allowability dated Oct. 9, 2012, issued in U.S. Appl. No. 12/713,135, 5 pages.
Notice of Allowability dated Oct. 11, 2012, issued in U.S. Appl. No. 11/169,326 2 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31 2012, issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.
Extended European Search report dated Dec. 10, 2012 issued in European Patent Application No. 07844549.1, 6 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
U.S. Office Action dated Feb. 25, 2013 issued in U.S. Appl. No. 12/762,920, 8 pages.
Canadian Office Action dated Dec. 13, 2012 issued in Canadian Patent Application No. 2,407,440, 6 pages.
International Search Report and Written Opinion dated Mar. 8, 2013 issued in PCT Patent Application No. PCT/US12/71199, 13 pages.
U.S. Office Action dated Apr. 15, 2013 issued in U.S. Appl. No. 13/470,678, 10 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. No. 12/762,948, 10 pages.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.

(56) References Cited

OTHER PUBLICATIONS

USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patent application No. 2005202099.
AU Examiners report dated Jan. 12, 2007 issued in corresponding Australian patent application No. 2006202337.
AU Examiners report dated Feb. 21, 2007 issued in corresponding Australian patent application No. 2005202099.
AU Examiners report dated May 23, 2007 issued in corresponding Australian patent application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
U.S. Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Themen, (16 pages).
Gray, Henry, Anatomy of the Human Body, 1918, 6d. The Foot 1. The Tarsus, II. Osteology, cover page and 10 pgs, www.Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vilex, (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php?pg=product_det_prn&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).

(56) References Cited

OTHER PUBLICATIONS

M. Siguier, MD et al, "Preliminary Results of Partial Surface Replacement of the Femoral Head in Osteonecrosis", The Journal of Arthroplasty, vol. 14, No. 1, 1999, pp. 45-51.
T. Siguier, MD et al, Partial Resurfacing Arthroplasty of the Femoral Head in Avascular Necrosis, Clinical Orthopaedics and Related Research, No. 386, 2001, pp. 85-92.
Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knee Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral head", An Experimental Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 pages).
Bale, MD, Reto J., et al, "Osteochondral Lesions of the Talus: Computer=assisted Retrograde Drilling Feasibility and Accuracy in Initial Experiences[1]", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus*, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 Jul.-Aug. 2001:pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, A service of the National Library of Medicine and the National Institutes of Health, Foot Ankle Int.Aug. 1999; 20(8):474-80.
Ueblacker, M.D., Peter, et al, "Retrograde Cartilage Transplantation of the Proximal and Distal Tibia", Arthroscopy: The Journal of Arthroscopic and Related Surgery, vol. 20, No. 1 Jan. 2004: pp. 73-78.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.

(56) References Cited

OTHER PUBLICATIONS

Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Feb. 14, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
Notice of Allowance dated Aug. 7, 2017, issued in U.S. Appl. No. 14/640,602, 8 pages.
Office Action dated Aug. 25, 2017, issued in U.S. Appl. No. 14/728,216, 10 pages.
Final Office Action dated Aug. 25, 2017, issued in U.S. Appl. No. 14/035,061, 10 pages.
Final Office Action dated Sep. 22, 2017, issued in U.S. Appl. No. 13/723,902, 21 pages.
Preliminary Report on Patentability dated Oct. 5, 2017, issued in PCT Patent Application No. PCT/US2016/023930, 11 pages.
Intent to Grant dated Oct. 6, 2017, issued in European Patent Application No. 11 751 521.3, 7 pages.
Final Office Action dated Oct. 6, 2017, issued in U.S. Appl. No. 13/796,675, 18 pages.
Intent to Grant dated Oct. 6, 2017, issued in European Patent Application No. 12 860 168.9, 7 pages.
Office Action dated Oct. 16, 2017, issued in European Patent Application No. 05 763 817.3, 5 pages.
Office Action dated Oct. 17, 2017, issued in U.S. Appl. No. 14/640,667, 10 pages.

Office Action dated Oct. 16, 2017, issued in Canadian Patent Application No. 2,759,027, 3 pages.
U.S. Notice of Allowance dated Nov. 30, 2017, issued in U.S. Appl. No. 14/640,529, 7 pages.
European Intent to Grant dated Dec. 1, 2017, issued in European Patent Application Serial No. 09 002 088.4, 6 pages.
U.S. Notice of Allowance dated Dec. 8, 2017, issued in U.S. Appl. No. 15/153,113, 5 pages.
U.S. Office Action dated Dec. 12, 2017, issued in U.S. Appl. No. 14/133,943, 28 pages.
Canadian Notice of Allowance dated Dec. 14, 2017, issued in Canadian Patent Application Serial No. 2,407,440, 1 page.
U.S. Notice of Allowance dated Jan. 10, 2018, issued in U.S. Appl. No. 14/640,774, 8 pages.
Sullivan, "Hallux Rigidus: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Becher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 28, 2009 issued in related U.S. Appl. No. 11/359,891.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Reasons for Rejection issued in related Japanese Patent Application No. 2003-394702 dated Jul. 21, 2009.
Notice of Reasons for Rejection issued in related Japanese Patent Application No. 20-541615 dated May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.

(56) References Cited

OTHER PUBLICATIONS

Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
International Search Report and Written Opinion dated Oct. 23, 2018, issued in PCT Patent Application No. PCT/US18/45157, 11 pages.
Office Action dated Sep. 5, 2018, issued in U.S. Appl. No. 15/606,643, 6 pages.
Office Action dated Sep. 13, 2018, issued in U.S. Appl. No. 14/133,943, 28 pages.
Office Action dated Nov. 9, 2018, issued in Canadian Patent Application No. 2,759,027, 4 pages.
U.S. Notice of Allowance dated Apr. 16, 2018, issued in U.S. Appl. No. 15/153,170, 10 pages.
Office Action dated Jun. 29, 2018, issued in U.S. Appl. No. 14/640,667, 11 pages.
U.S. Notice of Allowance dated May 16, 2018, issued in U.S. Appl. No. 14/728,216, 5 pages.
Office Action dated May 31, 2018, issued in U.S. Appl. No. 13/723,902, 15 pages.
Office Action dated Jun. 19, 2018, issued in U.S. Appl. No. 15/296,772, 8 pages.
Extended Search Report dated Nov. 26, 2018, issued in European Patent Application No. 16769660.8, 7 pages.
Notice of Allowance dated Jan. 22, 2019, issued in U.S. Appl. No. 15/296,772, 7 pages.
Office Action dated May 15, 2019, issued in U.S. Appl. No. 15/973,981, 6 pages.
Office Action dated Apr. 2, 2019, issued in U.S. Appl. No. 13/723,902, 19 pages.
Office Action dated Apr. 10, 2019, issued in U.S. Appl. No. 15/865,734, 8 pages.
Office Action dated May 9, 2019, issued in U.S. Appl. No. 15/943,949, 8 pages.
Office Action dated May 15, 2019, issued in U.S. Appl. No. 14/640,667, 16 pages.
Notice of Allowance dated Jul. 15, 2019, issued in U.S. Appl. No. 15/606,643, 5 pages.
Notice of Allowance dated Sep. 10, 2019, issued in U.S. Appl. No. 15/388,808, 8 pages.
Office Action dated Sep. 11, 2019, issued in U.S. Appl. No. 15/351,530, 15 pages.
Tornier Implants Chirurgicaux—Aequalis Reversed Shoulder Prosethesis, K132285, Dec. 5, 2013, 8 pages.
Tornier, Aequalis Reversed II Shoulder, Nov. 2014, 3 pages.
Johnson & Johnson Medical Devices Companies—Global PA Shoulder System, https://www.depuysynthes.com/hcp/shoulder/products/qs/DELTAXTEND-Reverse-Shoulder-System, Nov. 2014, 7 pages.
Zimmer Biomet-Joint Replacement Orthopaedic Devices_Hip_Knee_Shoulder, http://www.biomet.com/orthopedics/getfile.cfm?id=2905&rt=inline, Nov. 2014, 3 pages.
Notice of allowance dated Oct. 28, 2019, issued in U.S. Appl. No. 15/865,734, 7 pages.
Office Action dated Nov. 19, 2019, issued in U.S. Appl. No. 13/723,902, 16 pages.
Office Action dated Jan. 16, 2020, issued in U.S. Appl. No. 14/640,667, 10 pages.
Notice of allowance dated Dec. 16, 2019, issued in U.S. Appl. No. 15/973,981, 8 pages.
Notice of allowance dated Dec. 17, 2019, issued in U.S. Appl. No. 15/943,949, 7 pages.
Notice of allowance dated Dec. 18, 2019, issued in U.S. Appl. No. 14/133,943, 5 pages.
Office Action dated Dec. 30, 3019, issued in U.S. Appl. No. 15/943,956, 16 pages.
International Search Report and Written Opinion dated Jan. 16, 2020, issued in PCT International Patent Application No. PCT/US2019/058517, 9 pages.

\* cited by examiner

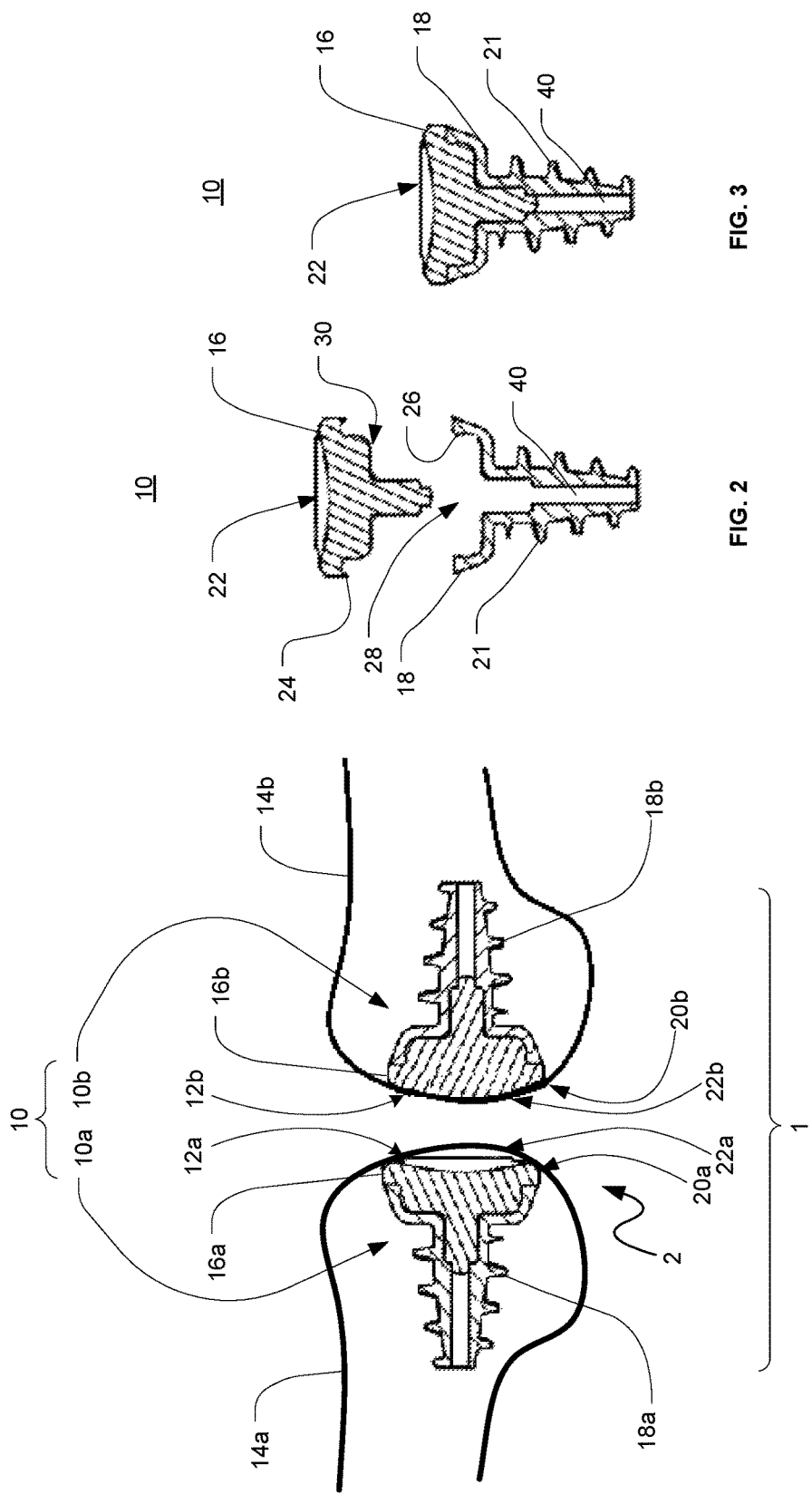

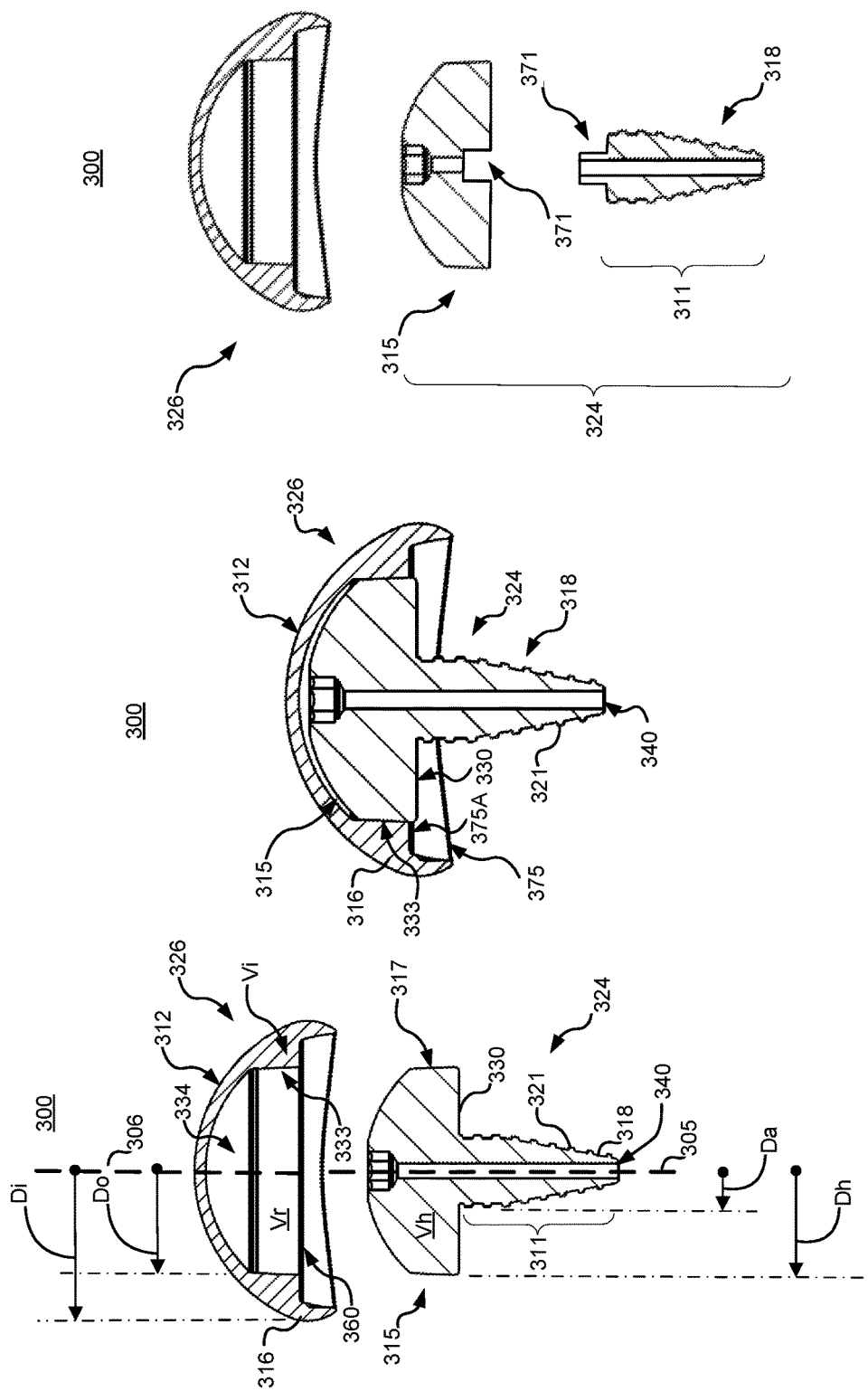

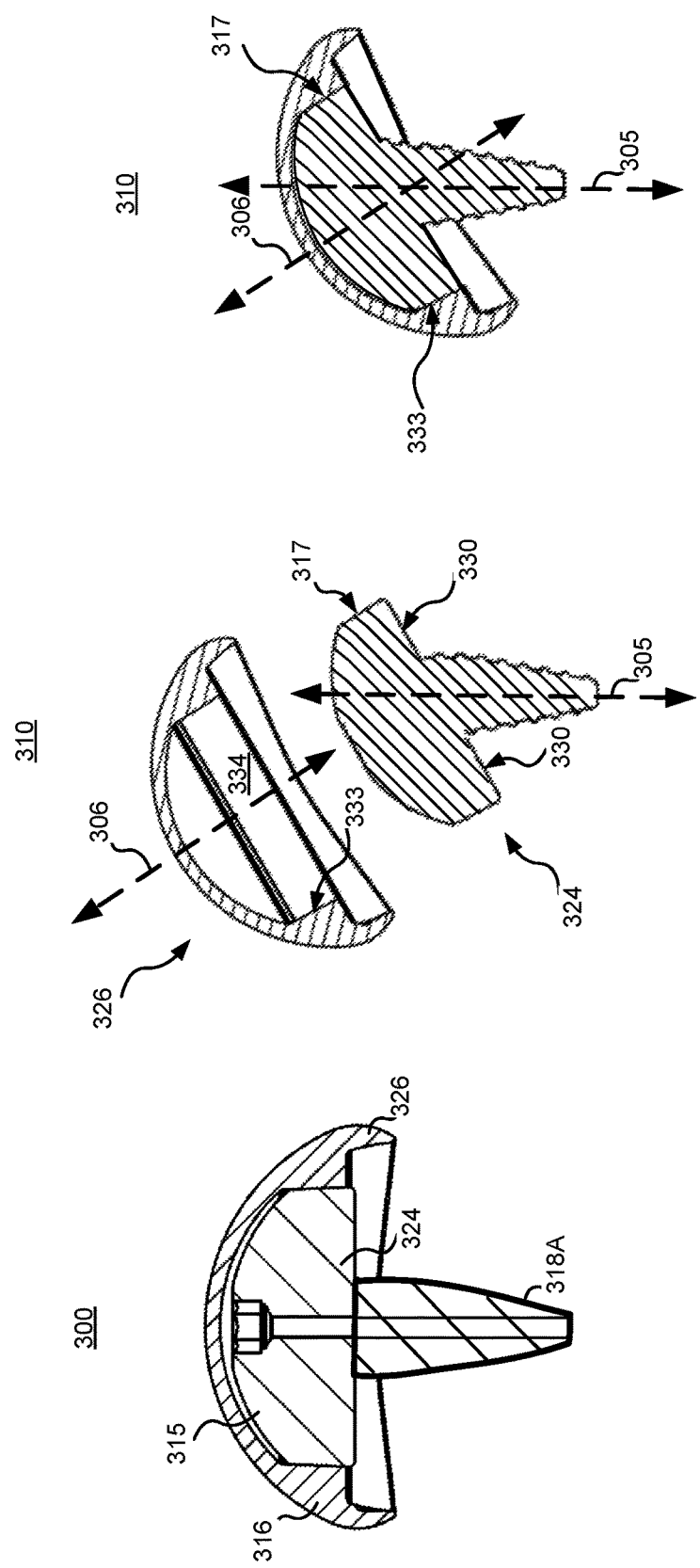

SYSTEM AND METHOD FOR REPAIRING ARTICULAR SURFACES

CROSS REFERENCE TO RELATED APPLICATIONS

This application is a continuation-in-part of U.S. patent application Ser. No. 14/640,774, filed Mar. 6, 2015, which claims the benefit of U.S. Provisional Application Ser. No. 61/949,774, filed Mar. 7, 2014; U.S. Provisional Application Ser. No. 61/949,789, filed Mar. 7, 2014; U.S. Provisional Application Ser. No. 61/949,824, filed Mar. 7, 2014; and U.S. Provisional Application Ser. No. 61/950,762, filed Mar. 10, 2014, the entire disclosures of which are fully incorporated herein by reference.

FIELD

The present disclosure relates to delivery systems for bone implants, and more particularly, to delivery systems for articular surface implants.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. One method of installing an implant involves applying a blunt force, e.g., a hammer/mallet or the like, to the implant. Unfortunately, some of the blunt force is transmitted from the implant into the surrounding bone and/or tissue and can cause damage to the bone/tissue. This is particularly problematic in small bones (such as, but not limited to, bones in the hand and/or foot) as well as patients who suffer from reduced bone mass and density that can lead to fracture (such as, but not limited to, osteoporosis or the like).

BRIEF DESCRIPTION OF THE DRAWINGS

Features and advantages of the claimed subject matter will be apparent from the following detailed description of some example embodiments consistent therewith, which description should be considered with reference to the accompanying drawings, wherein:

FIG. 1 generally illustrates a total joint replacement system installed in a patient's joint consistent with at least one embodiment of the present disclosure;

FIGS. 2 and 3 generally illustrate one embodiment of an implant system which may be used with the total joint replacement system consistent with at least one embodiment of the present disclosure;

FIGS. 23 and 24 show an assembled and unassembled view of the implant system of FIG. 20, respectively, in accordance with an embodiment of the present disclosure;

FIG. 25 shows a cross-sectional view of another embodiment of the implant system of FIG. 20;

FIG. 26 generally illustrates a further embodiment of an implant system consistent with at least one embodiment of the present disclosure;

FIGS. 27-28 show an assembled and unassembled view of the implant system of FIG. 20, respectively, in accordance with an embodiment of the present disclosure.

DETAILED DESCRIPTION

Figure 4:
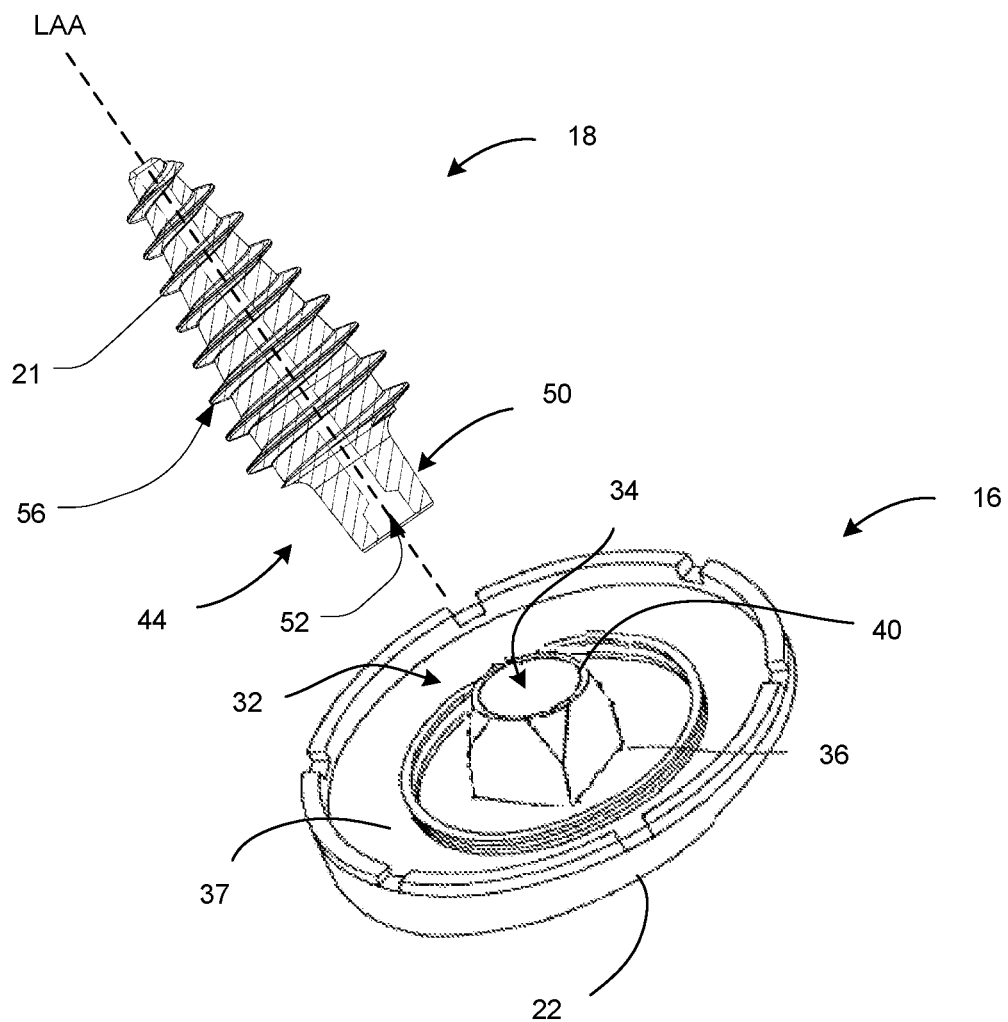
FIG. 4 generally illustrates another embodiment of an implant system which may be used with the total joint replacement system consistent with at least one embodiment of the present disclosure.

With reference to FIG. 1, one embodiment of total joint replacement system 1 installed in a patient's joint 2 is generally illustrated. The total joint replacement system 1 may include two or more implant systems 10 (e.g., a first and a second implant system 10a, 10b) installed in the articular surface 12a, 12b of a patient's bone 14a, 14b, respectively. Each one of the implant systems 10 is configured to repair and/or replace the articular surface 12a and/or 12b (referred to as articular surface 12 for simplicity) of a respective one of the patient's bones 14a and/or 14b (referred to as bone 14 for simplicity). The total joint replacement system 1 may be used with implant systems 10 for replacing any articular surface 12 such as, but not limited to, shoulder joints (e.g., but not limited to, the glenohumeral joint), hip joints (e.g., but not limited to, the acetabulofemoral joint), foot and/or hand joints (e.g., but not limited to, metacarpophalangeal joints, metatarsophalangeal joints, and/or interphalangeal joints), knee joints, elbow joints, or the like. One or more of the implant systems 10 may include total joint implants (wherein all or substantially all of the articular surface of at least one bone is replaced with the artificial surface of the implant) and/or partial implants (wherein substantially only the damaged portion(s) of the articular surface 12 of a bone 14 is replaced with the artificial surface of the implant). As explained herein, the implant systems 10a, 10b as illustrated in FIG. 1 are for illustrative purposes only, and the total joint replacement system 1 may be used with any implant system 10 as described herein.

Turning now to FIGS. 2-3, one embodiment of an implant system 10 which may be used with the total joint replacement system 1 consistent with the present disclosure is generally illustrated. For example, FIG. 2 generally illustrates one embodiment of an exploded, unassembled implant system 10, and FIG. 3 generally illustrates an assembled implant system 10. The implant system 10 may generally include an implant (e.g., implant body) 16 configured to be secured to an anchor 18. The anchor 18 is configured to be secured to the bone 14 within an excision site 20 formed beneath the patient's articular surface 12 such that a load bearing surface 22 of the implant 16 is generally flush with the patient's surrounding articular surface 12 as generally illustrated in FIG. 1.

The load bearing surface 22 may have any surface contour depending on the intended application. The load bearing surface 22 may be based on or generally correspond to the original contour of the patient's removed articular surface. For example, the load bearing surface 22 may have a contour substantially corresponding to or based on the contour of an articular surface of a patient being repaired. The contour of the load bearing surface 22 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 22 may be based on two or more curvatures, for example, the anterior-posterior curvature and the superior-inferior curvature. One or more of the anterior-posterior and/or superior-inferior curvatures may themselves be based on multiple curves, (for example, as generally described in U.S. patent application Ser. No. 12/027,121, filed Feb. 6, 2008 and entitled System and Method for Joint Resurface Repair, which is fully incorporated herein by reference).

While the load bearing surface 22 in FIGS. 2 and 3 is illustrated having a generally convex contour, it should be appreciated that the load bearing surface 22 is not limited to this configuration and will depend on the intend application. For example, the load bearing surface 22 may include, but is not limited to, generally concave configurations (e.g., as generally illustrated in FIG. 1) and/or generally hemi-spherical shapes.

The excision site 20 may be formed using any method and system known to those skilled in the art, such as, but not limited to, as the systems and methods as described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. According to one embodiment, the anchor 18 may be secured to the bone 14, for example, using one or more external threads, ribs, protrusions, bone cement, barbs, grooves or any other structure 21 that enables the anchor 18 to be secured to the bone 14. The use of threads 21 as generally illustrated may advantageously allow the height of the implant 12 to be adjusted by rotating the anchor 18 within the bone 14 such that the implant 16 is flush with the surrounding articular surface 12.

The anchor 18 is configured to engage and/or secure the implant assembly 10 to the patient's bone as described herein. Anchor 18 includes a proximal and a distal end region, and optionally may include a cannulated passageway 40. The cannulated passageway 40 may be configured to be advanced over a guide wire (not shown) extending outwardly from the excision site in the bone as generally described in U.S. Pat. Nos. 6,520,964, 6,610,067, 6,679,917, and 7,678,151, all of which are fully incorporated herein by reference. The use of a cannulated passageway 40 and the guide wire may facilitate alignment of the anchor 30 with respect to the excision site and the surrounding articular surface.

As discussed above, the implant 16 may be secured to the anchor 18 by way of a connection. For example, the implant 16 may include at least one first fixation element 24 configured to engage with at least one second fixation element 26 of the anchor 18 to secure the implant 16 to the anchor 18. According to one embodiment, the first and the second fixation elements 24, 26 may include one or more recesses, groves, slots or the like configured to corresponding to one or more protrusions, ribs, barbs, or the like, for example, in a snap-fit arrangement in which the first and/or second fixation elements resiliently deflect. The first and second fixation elements 24, 26 may be disposed about the entire perimeter/periphery of the implant 16 and anchor 18, and/or about one or more regions of the perimeter/periphery. The first and second fixation elements 24, 26 may prevent the implant 16 from becoming free relative to the anchor 18 (for example, to prevent axial and/or rotational movement of the implant 16 relative to the anchor 18). Optionally, the implant 16 may be at least partially received in an implant cavity 28 formed in the anchor 18 such that a bone facing surface 30 of the implant 16 engages against at least a portion of the implant cavity 28, thereby preventing the implant 16 from moving distally when a force is applied to the load bearing surface 22.

It should be appreciated that while the first and second fixation elements 24, 26 are generally illustrated as a recess and a protrusion, respectively, the implant system 10 consistent with the present disclosure is not limited to this arrangement unless specifically claimed as such. For example, the first and second fixation elements 24, 26 may include a protrusion and a recess, respectively, as well as other embodiments. Additionally, the anchor 18 may optionally include a passageway 40, for example, a longitudinal passageway, configured to be advanced over a guide wire (not shown) as generally described in U.S. Pat. Nos. 6,520, 964, 6,610,067, 6,679,917, 7,678,151, 7,896,883, 8,177,841, and 8,388,624, as well as U.S. Publication No. 2010/0368238, all of which are fully incorporated herein by reference. For example, the anchor 18 may be inserted into bone 14 or may be inserted into a shaft drilled in the bone 14 to reduce risks or complications arising from the insertion of the anchor 18. Without limitation, a pilot hole may be formed in the bone 14 for receiving the anchor 18 prior to installing the anchor 18. A diameter of the pilot hole may be smaller than the anchor 18, although example embodiments may vary and are not limited thereto.

Turning now to FIG. 4, another embodiment of an implant system 10 which may be used with the total joint replacement system 1 consistent with the present disclosure is generally illustrated. Implant system 10 includes an implant (e.g., implant body) 16 configured to be secured to an anchor 18. Implant 16 may be formed of a plastic composition and may more particularly comprise, essentially consist of, or consist of a plastic composition. Exemplary plastic compositions may comprise thermoplastic compositions such as polyether ether ketone (PEEK) and polyethylene (PE), including ultrahigh molecular weight polyethylene (UHMWPE) and high density polyethylene (HDPE). In other embodiments, implant 16 may be formed of a metal composition and may more particularly comprise, essentially consist of, or consist of a metal composition. Exemplary metal compositions may comprise stainless steel, titanium, aluminum, chromium cobalt, and/or any alloy thereof.

Implant 16 has a joint facing side including a load bearing (joint articulation) surface 22 having any contour as described herein, and a bone facing surface 37. Bone facing surface 37 may substantially correspond to a contour of an excision site 20 (FIG. 1) formed in an articular surface 12 of a patient. More particularly, a perimeter of the implant 20 may substantially corresponds to a perimeter of an excision site 20 formed in the articular surface 12.

Bone facing surface 37 includes a first fixation element 32. First fixation element 32 comprises a fixation recess 34 formed in a fixation base 36 of implant 16. As shown, fixation recess 34 is substantially cylindrical and may be centered around a longitudinal axis LAA of the anchor 18. More particularly, the sidewall 40 of fixation recess 34 is tapered The anchor 18 is configured to engage and/or secure the implant assembly 10 to the patient's bone as described herein, for example, using threads 21 and/or bone cement. The proximal end region of the anchor 18 includes a second fixation element 44 configured to form a connection with the first fixation element 32. As shown by the figures, anchor 18 may comprise a screw with a fully or partially threaded tapered or non-tapered cylindrical shank which is arranged substantially transverse to the overlying portion of the load bearing surface 22.

As discussed herein, second fixation element 44 is configured to engage with the first fixation element 32 to form a connection therebetween. In the illustrated embodiment, the second fixation element 44 includes a tapered (male) protrusion. The tapered protrusion includes a tapered sidewall 50 configured to contact and abut against at least a portion of a tapered sidewall 40 of the first fixation element 32 to form a frictional connection therebetween. Of course, it should be appreciated that the arrangement of the male and female tapers with respect to the first and second fixation elements 32, 44 may be switched (e.g., the first fixation element 32 may include a male taper and the second fixation element 44 may include a female taper).

The proximal end region of the anchor 30 may also include a driver receptacle 52 arranged to receive a drive member therein, particularly to drive the first anchor 30 into bone. For example, driver receptacle 52 may be arranged to receive a drive member (not shown) to cause one or more anchor elements 56 of the anchor 18 to engage the bone 14. The driver receptacle 52 may allow torque to be transmitted to the anchor 18 to rotate the anchor 18 such that one or more external screw (helical) threads 21 threadably engage and connect with the bone 14.

Elongated anchor 18 may be formed of a plastic composition and may more particularly comprise, essentially consist of, or consist of a plastic composition. Exemplary plastic compositions may comprise thermoplastic compositions such as polyether ether ketone (PEEK) and polyethylene (PE) such as ultrahigh molecular weight polyethylene (UHMWPE) and high density polyethylene (HDPE). In other embodiments, anchor 18 may be formed of a metal composition and may more particularly comprise, essentially consist of, or consist of a metal composition. Exemplary metal compositions may comprise stainless steel, titanium, aluminum, chromium cobalt, and/or any alloy thereof.

Figure 5:
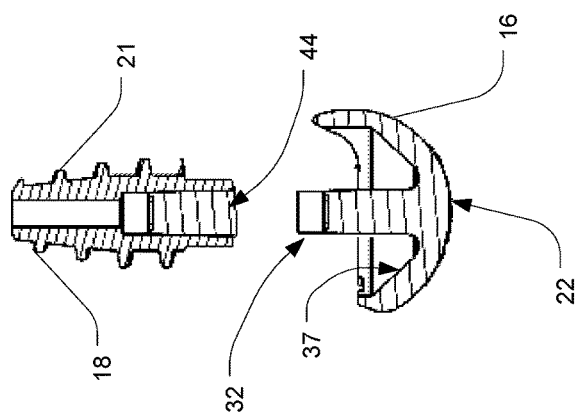
FIGS. 5 and 6 generally illustrate a further embodiment of an implant system which may be used with the total joint replacement system consistent with at least one embodiment of the present disclosure.
Figure 6:
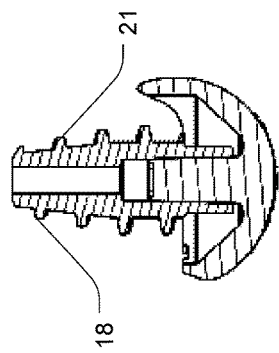
Figures 7A, 7B, 7C, 7D, 7E:
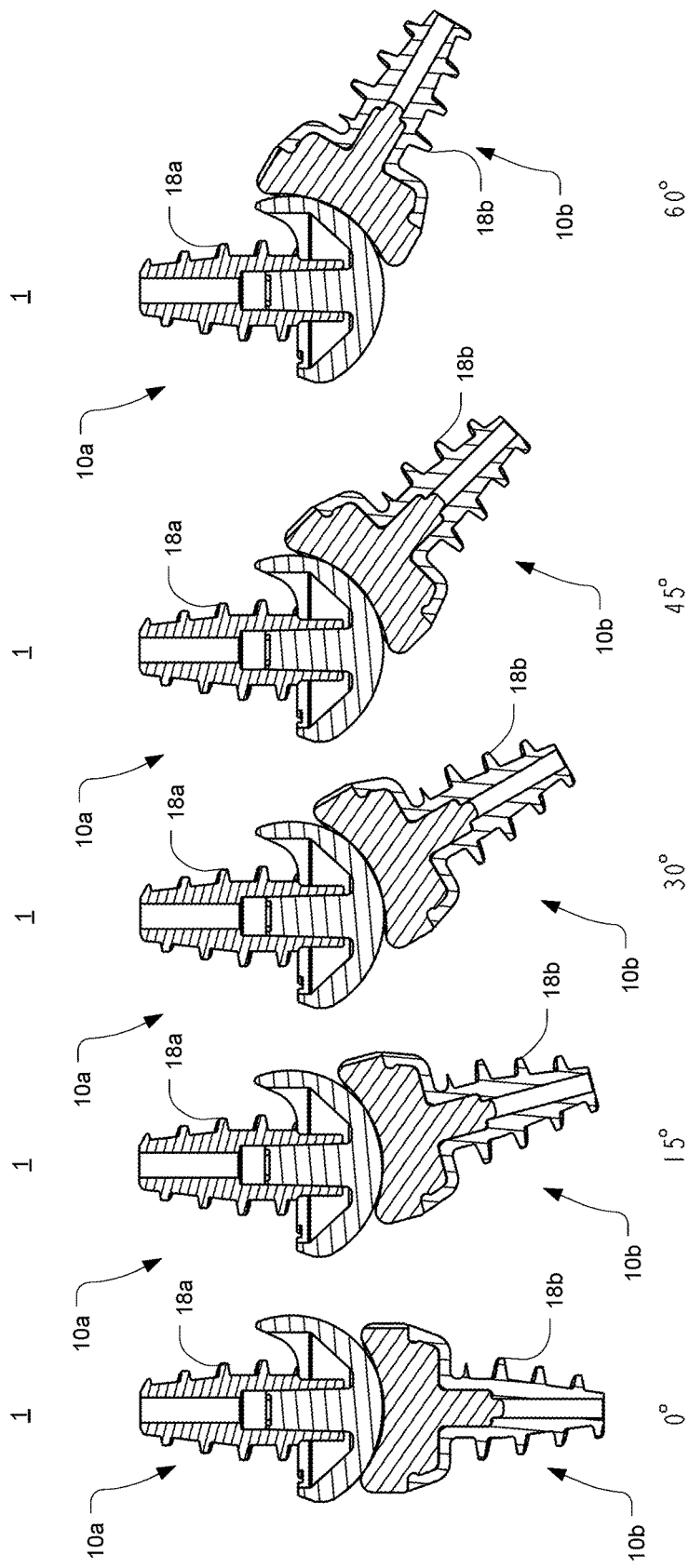
FIGS. 7a-7e generally illustrate cross-sectional views of another embodiment of the total joint replacement system consistent with at least one embodiment of the present disclosure at different angles.

Turning now to FIGS. 5-6, yet another embodiment of an implant system 10 which may be used with the total joint replacement system 1 consistent with the present disclosure is generally illustrated. For example, FIG. 5 generally illustrates one embodiment of an exploded, unassembled implant system 10, and FIG. 6 generally illustrates an assembled implant system 10. Implant 16 has a load bearing surface 22 and a bone facing surface 37. The load bearing surface 22 may have contour as described herein, for example, the original contour of the patient's articular surface generally corresponding to a plurality of overlapping excision sites (e.g., if replacing the dorsal socket or the like). The bone facing surface 37 may also include a first fixation element 32 configured to be secured to a second fixation element 44 of the anchor 18 to form a connection therebetween. In the illustrated embodiment, the first fixation element 32 includes a tapered (male) protrusion and the second fixation element 44 includes a tapered recess. The tapered protrusion includes a tapered sidewall configured to contact and abut against at least a portion of a tapered sidewall of the tapered recess to form a frictional connection therebetween. Of course, it should be appreciated that the arrangement of the male and female tapers with respect to the first and second fixation elements 32, 44 may be switched (e.g., the first fixation element 32 may include a female taper and the second fixation element 44 may include a male taper).

FIGS. 7a-7e generally illustrate cross-sectional views of another embodiment of the total joint replacement system 1 consistent with the present disclosure at different angles, e.g., ranging between 0° and 60°. The total joint replacement system 1 includes a first implant system 10a as generally described herein with respect to FIGS. 5 and 6, and a second implant system 10b as generally described herein with respect to FIGS. 2 and 3. For the sake of clarity, the bones of the joint are not illustrated.

The anchors 18a of the first implant system 10a may be secured to bone as described herein. For example, the height of the anchor 18a may be adjusted by rotating the anchor 18a. Optionally, a trial guide (not shown) may be coupled to the anchor 18a to allow the surgeon to verify that the load bearing surface 22 is substantially flush with the surrounding articular surface (if present) and/or generally corresponds to the location of the original articular surface.

The anchor 18b of the second implant system 10b may also be secured to the bone as described herein. Similarly, the height the anchor 18b may be adjusted by rotating the anchor 18b, and optionally using an implant trial guide (not shown). One advantage of the total joint replacement system 1 is that the height of the anchors 18a, 18b may be infinitely adjusted, and once adjusted to the desired height, the implant 16a, 16b may be secured to the anchors 18a, 18b in the correct orientation. For example, the implant 16a (because it has a non-symmetrical load bearing surface 22) should be aligned in a predetermined orientation with respect to the bone (e.g., the metatarsal bone). Similarly, the implant 16b should be aligned in a predetermined orientation with respect to the phalangeal bone and/or the first implant 16a (e.g., the implant 16b may have a generally convex contour configured to generally align with and slide against the implant 16a as generally illustrated in FIGS. 7a-7e). Thus, the height and/or separation distance between the bones (e.g., metatarsal and phalangeal bones) may be infinitely adjusted without impacting the alignment of the implants 16a, 16b (i.e., the alignment of the implants 16a, 16b may be independent of the position of the anchors 18a, 18b).

Figure 8:
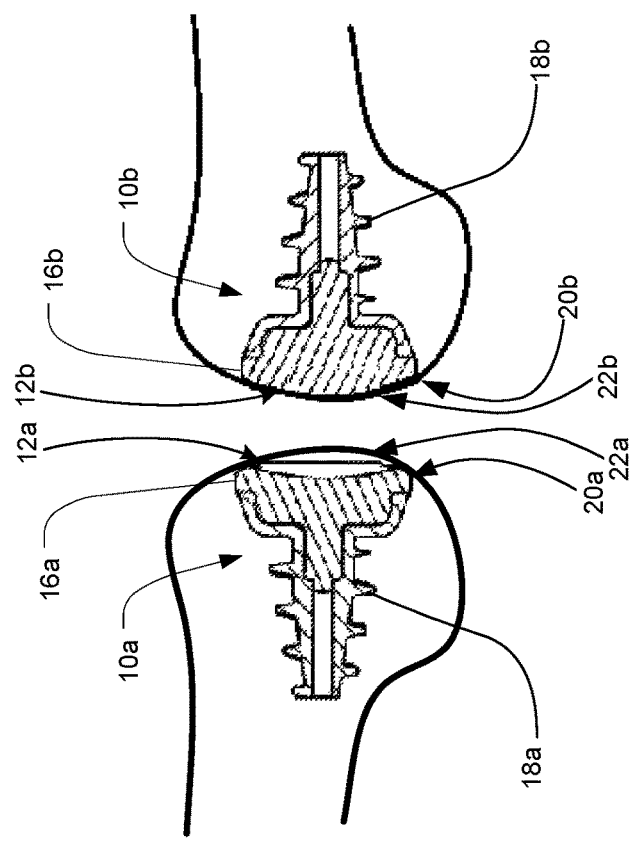
FIG. 8 generally illustrates a further embodiment of an implant system which may be used with the total joint replacement system consistent with at least one embodiment of the present disclosure.

Turning now to FIG. 8, yet another embodiment of the total joint replacement system 1 is generally illustrated. The total joint replacement system 1 includes a first and a second implant system 10a, 10b similar to the implant systems 10 as generally described herein with respect to FIGS. 2 and 3. In particular, the first implant system 10a includes an implant 16a having a generally convex load bearing surface 22a and the second implant system 10b includes an implant 16b having a generally concaved load bearing surface 22b configured to mate with load bearing surface 22a.

Turning now to FIGS. 9-17, systems and methods for securing an anchor 18 into the bone and securing the implant 16 to the anchor 18 using an implant delivery system 100 consistent with the present disclosure are generally illustrated. In a first mode (as generally illustrated in FIGS. 9-13), the implant delivery system 100 may be used to secure the anchor 18 into an excision site formed in the bone. In a second mode (FIGS. 14-17), the delivery system 100 may be used to secure the implant 16 to the anchor 18 to assemble the implant system 10 within the excision site. As may be appreciated, the implant delivery system 100 may be used with any implant system 10 described herein and is not limited to the illustrated implant system 10 unless specifically claimed as such.

Figure 10:
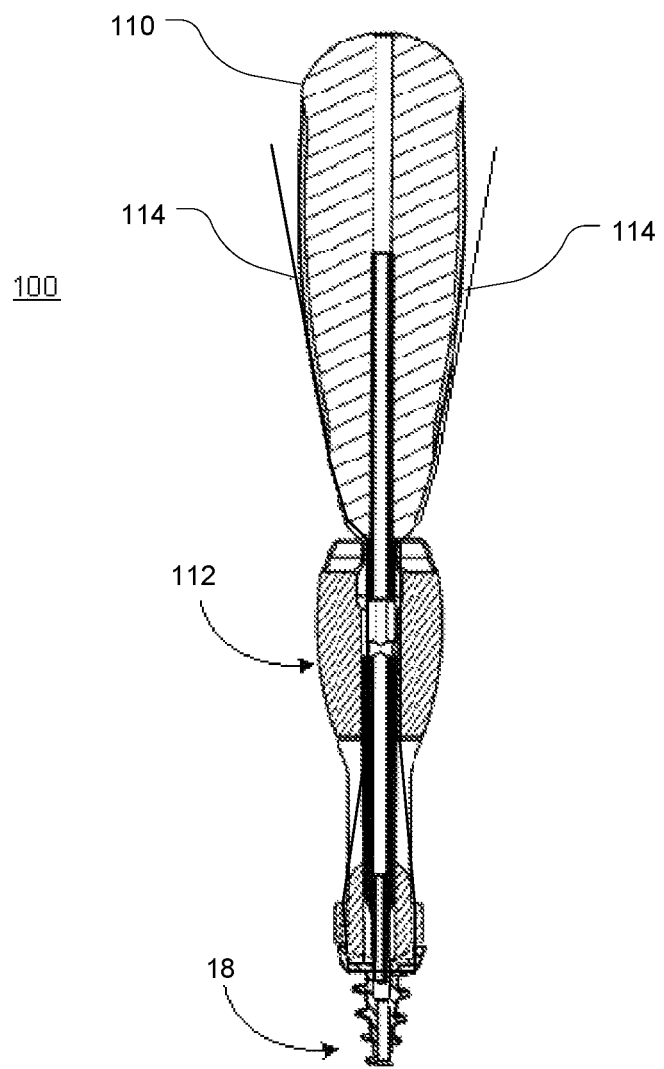
FIGS. 10-12 generally illustrate various steps in the installation of an anchor consistent with at least one embodiment of the present disclosure.
Figure 11:
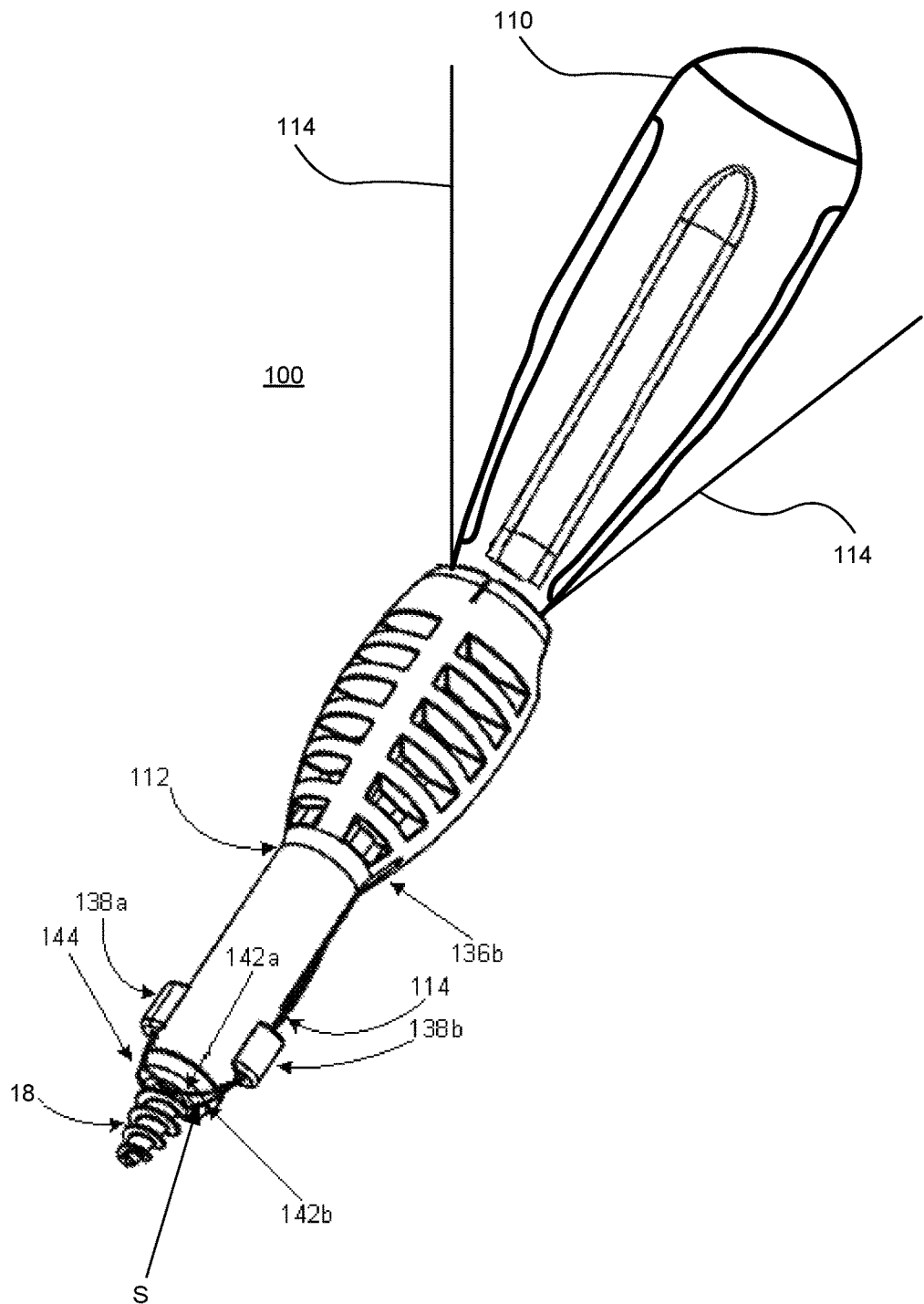
Figure 12:
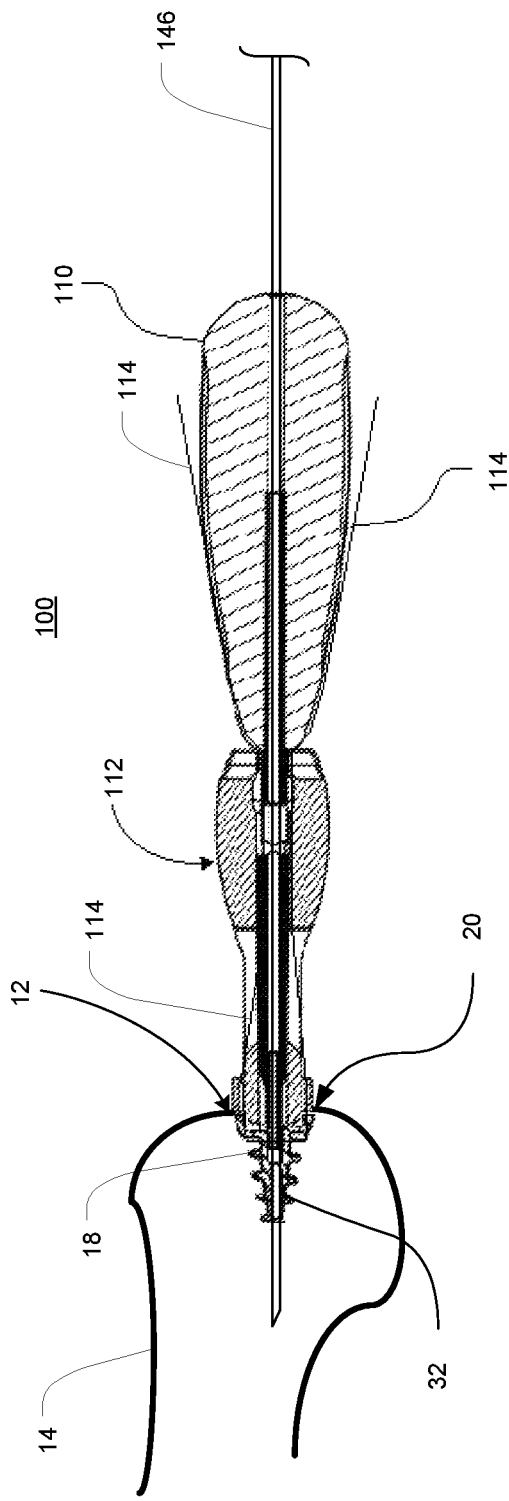
Figure 13:
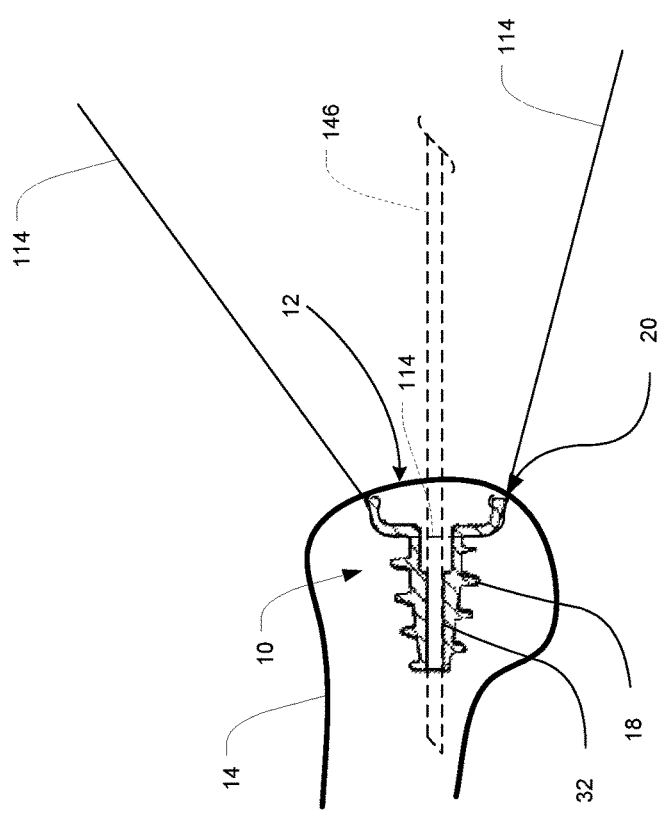
FIG. 13 generally illustrates an anchor secured in the bone consistent with at least one embodiment of the present disclosure.

With reference to FIGS. 9-13, one embodiment of system and method for using the implant delivery system 100 to secure the anchor 18 to bone within an excision site is generally illustrated. The implant delivery system 100 may include a driver 110, a biasing body 112, and at least one suture 114. As explained herein, the implant delivery system 100 may be configured to retain the anchor 18 into engagement with the driver 110 and to secure the anchor 18 to bone 14 within an excision site 20 (as generally illustrated in FIGS. 12 and 13). For example, the driver 110 may be received through the biasing body 112, and the suture 114 may be disposed around a portion of the anchor 18 to provide increased control and/or maintain contact between the driver 110 and the anchor 18 while securing the anchor 18 into the bone 14 within the excision site 20. The excision site 20 may be formed using any method and system known to those skilled in the art.

Figure 9A:
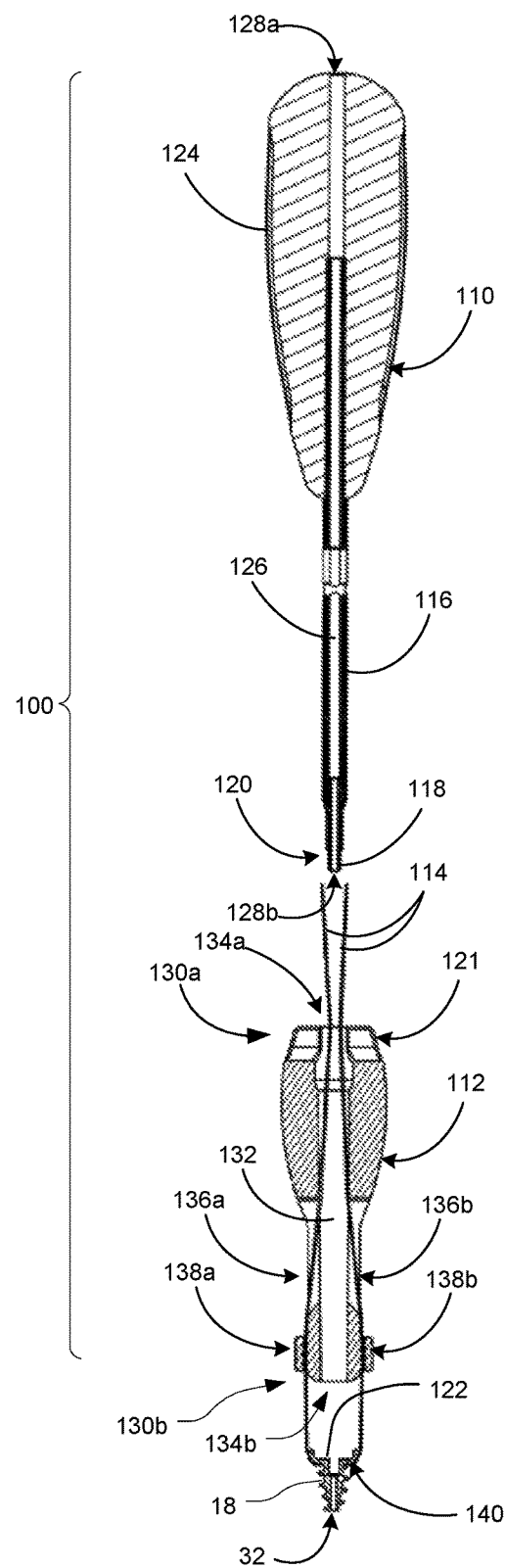
FIG. 9A generally illustrates one embodiment of an implant delivery system which may be used with the total joint replacement system consistent with at least one embodiment of the present disclosure.
Figure 9B:
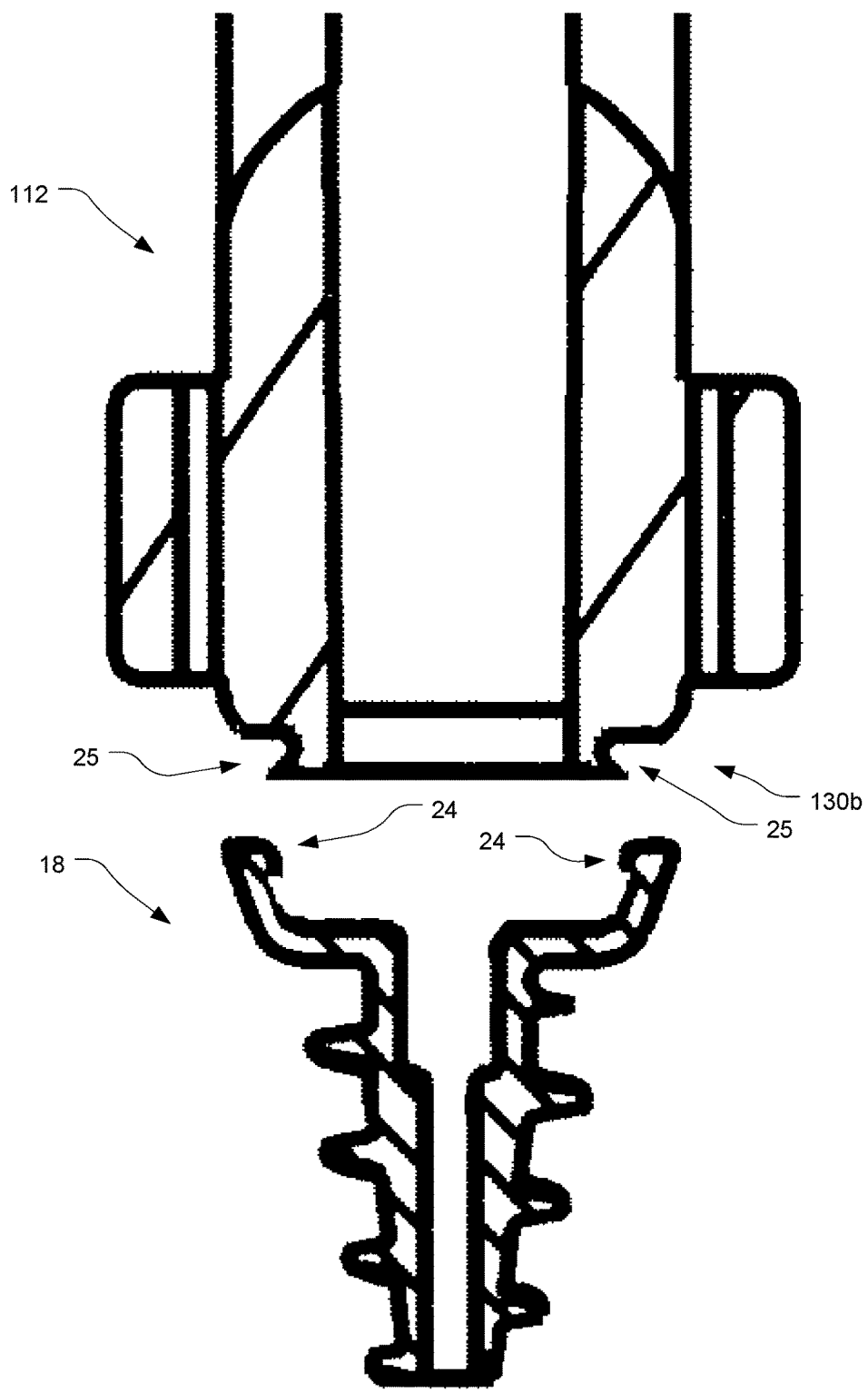
FIG. 9B generally illustrates a close up region of the implant delivery system of FIG. 9A.

The driver 110, FIG. 9A, includes a longitudinally disposed shaft 116 having an engagement portion 118 disposed about a distal end 120. The engagement portion 118 is configured to be coupled with a corresponding engagement portion 122 of the anchor 18 and to transmit torque as generally illustrated in FIGS. 10-12. For example, the engagement portion 118 may be a male-shaped coupling unit (such as, but not limited to, a splined or hex-shaped driver) configured to couple with a female-shaped coupling unit 122 (such as, but not limited to, a splined or hex-shaped recession formed in the anchor 18) in order to rotate or drive the anchor 18 into the bone. However, the engagement portions 118, 122 may vary and are not limited thereto. For example, the driver 110 may be configured to accept interchangeable bits having a different engagement portion 118 configurations, thereby allowing the engagement portion 118 of the driver 110 to be coupled to the engaging portion 122 of the anchor 18 using several different bits as necessary. Alternatively (or additionally), the engagement portion 118 may have a female-shaped coupling unit and the anchor 18 may have a male-shaped coupling unit. The shape of the engaging portions 118, 122 may be other than splined or hexagonal, and those in the art will recognize that one of any number of shapes or configuration for such components may be employed in a device or method consistent with example embodiments. Optionally, the engagement portion 118 may be magnetized or otherwise configured to maintain contact or control over the anchor 18.

While the engaging portion 122 of the anchor 18 is shown located on an inner wall of the narrow portion of the anchor 18, example embodiments may vary and are not limited thereto. For example, the engaging portion 122 of the anchor 18 may be located on an inner wall of the wide portion of the anchor 18 and/or on an outer wall of either the narrow portion or the wide portion of the anchor 18. Optionally, an intermediate or adapting portion (not shown) may be used to connect the driver 110 to the anchor 18.

The driver 110 may optionally include a handle 124. The handle 124 may facilitate grasping of the driver 110 and may be configured to cause a rotational force or a torque on the shaft 116, which may ultimately impart a rotational force or torque on the anchor 18 to secure the anchor 18 into the bone. The handle 124 may be separate from the shaft 116 (either permanently or removably coupled thereto), or may be a unitary, single piece with the shaft 116. While the handle 124 is illustrated as having a larger width than the shaft 116, example embodiments may vary and are not limited thereto. For example, the handle 124 may include a lever arm or may be configured to couple to a lever arm that is used to create the rotational force or torque.

The handle 124 and/or the shaft 116 may be cannulated to define a longitudinal passageway 126. The longitudinal passageway 126 may include proximal and distal openings 128a, 128b configured to be advanced over a guide wire (not shown for clarity), for example, when securing the anchor 18 into the bone within the excision site.

The biasing body 112 defines a shaft passageway 132 extending between a first and a second end region 130a, 130b having a first and second opening 134a, 134b. The shaft passageway 132 is configured to receive at least a portion of the shaft 116 of the driver 110, for example, as generally illustrated in FIGS. 10 and 11. The shaft 116 and the shaft passageway 132 may be configured such that the distal end 120 of the shaft 116 extends beyond the second end 134b of the shaft passageway 132 to allow the engagement portion 118 of the driver 110 to engage the corresponding engagement portion 122 of the anchor 18, for example, as generally illustrated in FIGS. 10 and 11. Optionally, the biasing body 112 may include a driver cradle 121, discussed in greater detail herein, which may be used to secure the implant 16 (not shown) with the anchor 18.

Additionally, the second end region 130b may include a fixation element 25 (FIG. 9B) which substantially corresponds to the first fixation element 24 of the implant 16. In this manner, the fixation element 25 of the second end region 130b of the biasing body 112 may be coupled to the second fixation element 26 of the anchor 18 to generally secure the anchor 18 to the biasing body 112. The connection between the biasing body 112 and the anchor 18 may facilitate placement of the anchor 18 within the excision site by creating a generally secure connection therebetween. It may be appreciated, however, that the connection between the fixation element 25 of the second end region 130b and the second fixation element 26 of the anchor 18 does not need to be as strong as the connection between the first and second fixation elements 24, 26 since it is only generally intended to help advance the anchor 18 to and align the anchor 18 within the excision site.

Alternatively (or in addition to), the biasing body 112, FIG. 9A, may be configured to receive a suture 114 disposed around (e.g., wrap around) a portion of the anchor 18. Tension may be applied to the suture 114 to generally urge the anchor 18 into contact with the driver 110 and/or the biasing body 112 to provide more control over and/or maintain contact between the driver 110 and the anchor 18. The suture 114 may be configured to extend through and/or around the biasing body 112 in any manner known to those skilled in the art. For example, the suture 114 may extend through the first opening 134a of the shaft passageway 132 of the biasing body 112, out through one or more suture apertures/openings/passageways 136a, 136b, through one or more suture alignment guides 138a, 138b and around a contact portion 140 of the anchor 18. The suture passageways 136a, 136b may allow the suture 114 to pass from the exterior of the biasing body 112 to the interior of the shaft passageway 132. While the suture passageways 136a, 136b are illustrated in the middle of the biasing body 112, example embodiments may vary and are not limited thereto. It should also be appreciated that the suture 114 does not have to pass through the shaft passageway 132, and instead the biasing body 112 may include one or more separate passageways (not shown) for the suture 114.

The suture alignment guides 138a, 138b are configured to retain the suture 114 about the distal end of the biasing body 112. According to one embodiment, the suture 114 may include a first and a second portion 142a, 142b (best seen in FIG. 11) which form a basket, cradle, or frame 144 extending about the contact portion of the anchor 18. The first and second portions 142a, 142b may be formed from two or more pieces of suture, or may be formed from a single piece of suture. The suture alignment guides 138a, 138b may be configured to prevent the first and second portions 142a, 142b of the cradle 144 from slipping off the anchor 18 by restricting the separation angle S of the first and second portions 142a, 142b of the cradle 144.

While the suture alignment guides 138a, 138b are shown at the distal end of the biasing body 112 nearest the anchor 18, example embodiments may vary and are not limited thereto. For example, the suture alignment guides 138a, 138b may be located anywhere along the biasing body 112 provided the suture alignment guides 138a, 138b may prevent the suture 114 from slipping off the anchor 18. Additionally, while the suture alignment guides 138a, 138b are shown as an exterior protrusion of the biasing body 112 with holes to allow the suture 114 to pass through, example embodiments may vary and are not limited thereto. For example, the suture alignment guides 138a, 138b may be flush with the biasing body 112 or may protrude in an arc shape, with a gap between one edge of the suture alignment guides 138a, 138b and the biasing body 112 to allow the suture 114 to enter. It may also be appreciated that the length of the suture alignment guides 138a, 138b may vary and the suture alignment guides 138a, 138b may be integrated into the suture passageways 136a, 136b.

While the contact portion 140 of the anchor 18 is shown on the bottom edge of the anchor 18, example embodiments may vary and the contact portion 140 may be situated anywhere along the anchor 18. For example, the contact portion 140 may also be disposed about the top portion of anchor 18. The contact portion 140 of the anchor 18 may include a flat edge or may include guides, grooves, slots, or channels configured to receive the suture 114. For example, the suture 114 may extend through a passageway formed in the anchor 18 such that a portion of the anchor 18 generally surrounds the suture 114, and the cradle 144 may be eliminated.

To secure the anchor 18 to the bone 14 within the excision site 20, the suture 114 may be received through the biasing body 112 (e.g., through the first opening 134a of the shaft passageway 132, out through the suture passageways 136a, 136b, and through the suture alignment guides 138a, 138b) such that the cradle 144 is disposed about the contact portion 140 of the anchor 18 as generally illustrated in FIG. 9A. The driver 110 may be advanced through shaft passageway 132 until the engagement portion 118 contacts the corresponding engagement portion 122 of the anchor 18. The suture 114 may then be tensioned to retain the engagement between the driver 110 and the anchor 18, for example, by applying a force against the suture 114 in a direction generally away from the anchor 18 as generally illustrated in FIGS. 10 and 11. Alternatively (or in addition), the fixation element 25 (FIG. 9B) of the biasing body 112 may be secured to the fixation element 26 of the anchor 18, and the driver 110 may engage the anchor 18 as described herein.

With the anchor 18 securely engaged with the driver 110, the anchor 18 may be advanced to and aligned with the excision site 20 (as generally illustrated in FIG. 12) formed in the patient's articular surface 12 and bone 14. Optionally, the anchor 18 may be aligned with the excision site 20 using a guide wire 146 extending outwardly from the bone 14 within the excision site 20. Because the anchor 18 is retained against the driver 110, it is easier for the surgeon to align the anchor 18 relative to the excision site 20. As discussed herein, the anchor 18 may optionally include a cannulated passageway 32 (best seen in FIG. 9A) that is generally aligned with (e.g., generally co-axial) the longitudinal passageway 126 of the driver 110 (as best illustrated in FIG. 12) such that the anchor 18 and the driver 110 (and optionally the biasing device 112) may be advanced over the guide wire 146. The optionally use of the cannulated passageway 32 and the guide wire 146 may further aid in aligning the anchor 18 at the desired angle with respect to the excision site 20 and the surrounding articular surface 12.

Once the anchor 18 is aligned with respect to the excision site 20, the driver 110 may then be used to secure the anchor 18 into the bone 14, for example, by rotating the driver 110, thereby causing the anchor 18 to rotate. The height of the anchor 18 may be verified using a trial gauge (not shown) which may be easily inserted/placed into the anchor 18 to ensure that the implant 16 (e.g., FIG. 1) is substantially flush with the surrounding articular surface 21. Once the height of the anchor 18 is verified, the driver 110 (and optionally the biasing device 112 and/or the guide wire 146) may be removed, leaving the anchor 18 (and optionally the suture 114) remaining in the bone 14, as generally illustrated in FIG. 13. While the anchor 18 is illustrated having threads 21, it may be appreciated that the anchor 18 may be secured to the bone 14 using any device(s) known to those skill in the art including, but not limited to, ribs, barbs, bone cement, porous structures, and the like.

It should also be appreciated that the biasing device 112 does not have to be used when advancing and/or aligning the anchor 18 with respect the excision site 20. For example, the biasing device 112 may be eliminated and tension may be applied to the suture 114 to keep the anchor 18 engaged with the driver 110. Alternatively, the anchor 18 may be advanced to and aligned with the excision site 20 without using the driver 110. For example, the suture 114 may be secured about a portion of the anchor 18, and once the anchor 18 is aligned within the excision site 20, the driver 110 may engage the anchor 18 and used to secure the anchor 18 within the excision site 20 in the bone 14.

Turning now to FIGS. 14-17, systems and methods for securing an implant 16 to the anchor 18 using an implant delivery system 100 consistent with the present disclosure are generally illustrated. As discussed herein, the implant delivery system 100 may be configured to generate a biasing force to secure the implant 16 to the anchor 18 wherein the biasing force is only applied against the implant 16 and the anchor 18, and not the surrounding bone or tissue 14.

Figure 14:
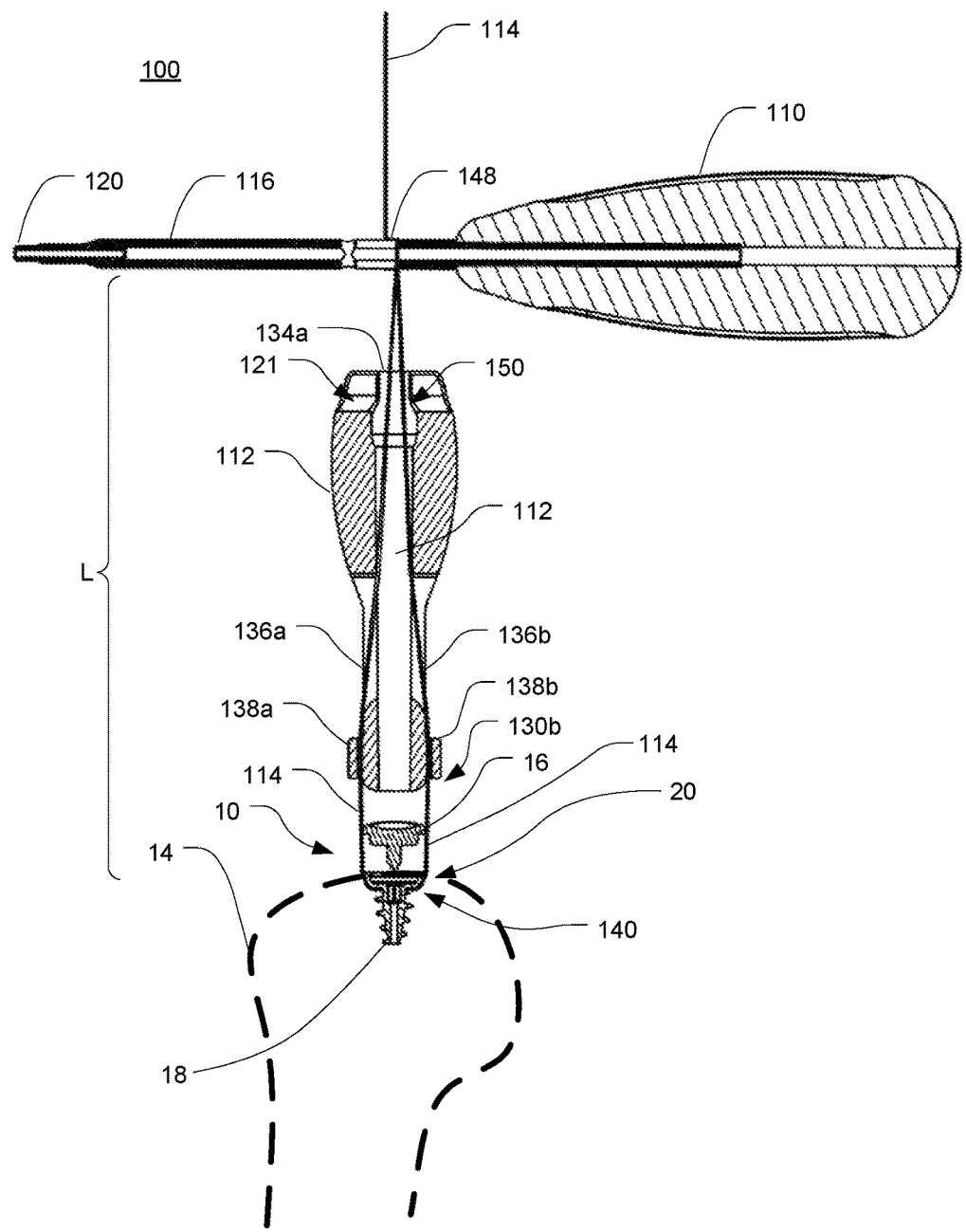
FIGS. 14-17 generally illustrate various steps in the installation/coupling of the implant with an anchor consistent with at least one embodiment of the present disclosure.
Figure 15:
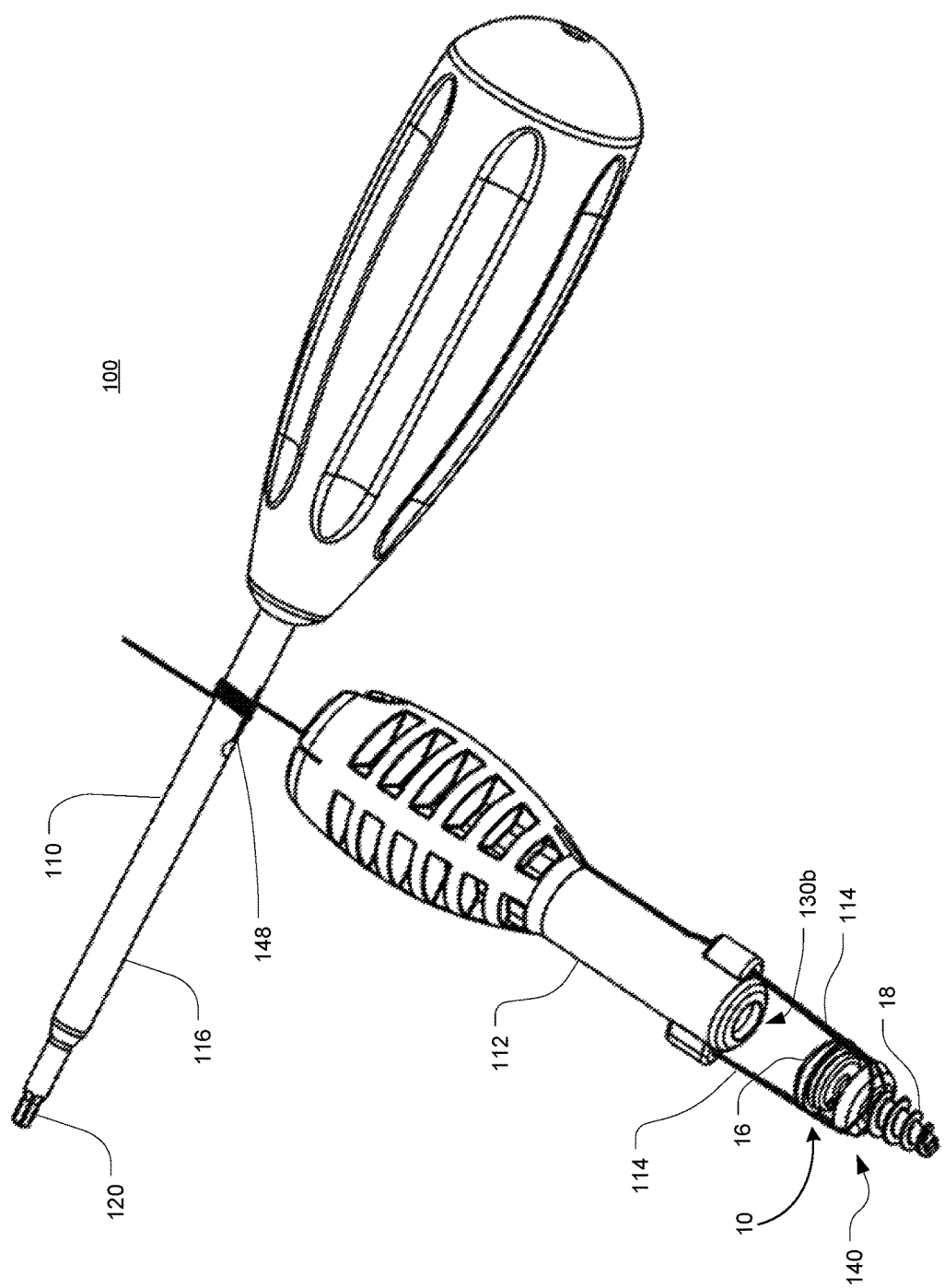

With the anchor 18 secured to the bone 14 and the suture 114 disposed about the contact portion 140 of the anchor 18 as described herein, the implant 16 may be arranged (i.e., placed) between the anchor 18 and the second end region 130b of the biasing device 112 as generally illustrated in FIGS. 14 and 15. The suture 114 may extend around the contact portion 140 of the anchor 18, through suture alignment guides 138a, 138b and suture passageways 136a, 136b, and exit through the first opening 134a of the shaft passageway 132 of the biasing body 112. The suture 114 may also be generally coupled or secured to a portion of the driver 110, for example, a portion of the shaft 116. For example, the driver 110 may include a suture engagement 148 configured to allow the suture 114 to be generally fixed or retained by the driver 110.

According to one embodiment, the suture engagement 148 may include a hole or aperture through the shaft 116. At least a portion of the suture 114 may pass through the hole 148, and the suture 114 may be secured within the suture engagement 148 as the driver 110 is rotated to reduce the length L of the suture 114 between the driver 110 and the anchor 18 as explained herein. It should be appreciated that the suture engagement 148 may include any device for generally securing the suture 114 to the driver 110. For example, the suture engagement 148 may include an external protrusion, a groove, non-cylindrical region, and/or a slot configured to secure the suture 114. Alternatively, the suture 114 may be wrapped around the shaft 116, and the tension generated by the rotation of the driver 110 may secure the suture 114 thereto. The length of the biasing body 112 may be selected to allow the surgeon sufficient room to rotate the driver 110, and therefore may depend on the intended application.

With the suture 114 generally secured to the driver 110, the driver 110 may be rotated about its longitudinal axis A as it is received within the driver cradle 121. The driver cradle 121 may be configured to receive the driver 110 (e.g., the shaft 116) and generally retain the shaft 116 as the shaft 116 is rotated relative to the biasing body 112. For example, the driver cradle 121 may include one or ore recesses, grooves, or lips formed in the first end region 134a of the biasing body 112. The driver cradle 121 may also include one or more holes or passageways formed through the biasing body 112 configured to receive and generally retain the shaft 116.

Optionally, the driver cradle 121 may include an enlarged opening 150 (best seen in FIG. 9). As the driver 110 is rotated, the suture 114 begins to wrap around the shaft 116, thereby increasing the diameter of the shaft 116. The enlarged opening 150 provides a void space that the suture 114 can pass through as the driver 110 is rotated and the suture 114 builds up around the shaft 116. As a result, the suture 114 may generally avoid contact with the driver cradle 121, and the torque necessary to rotate the driver 110 may be reduced.

Figure 16:
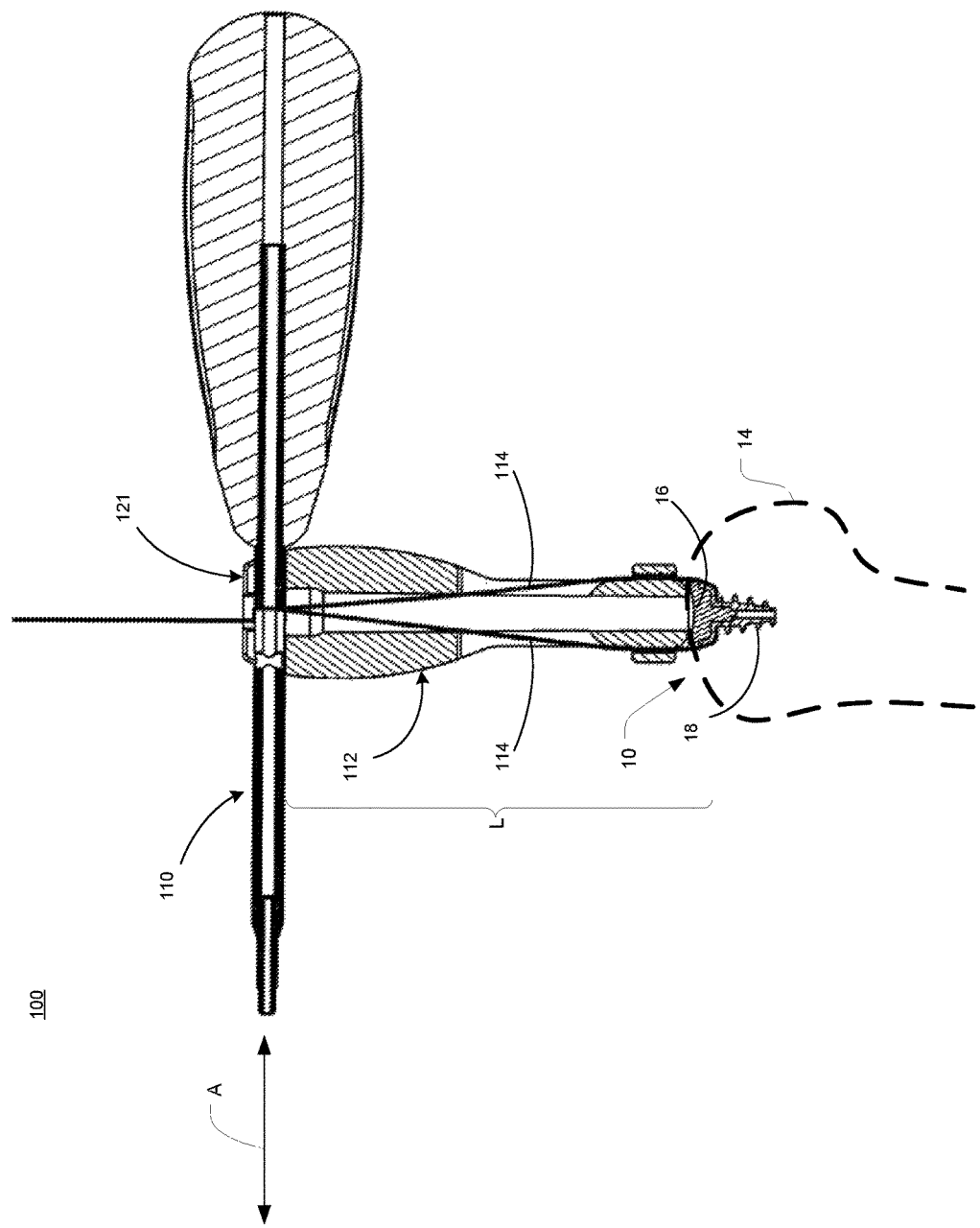
Figure 17:
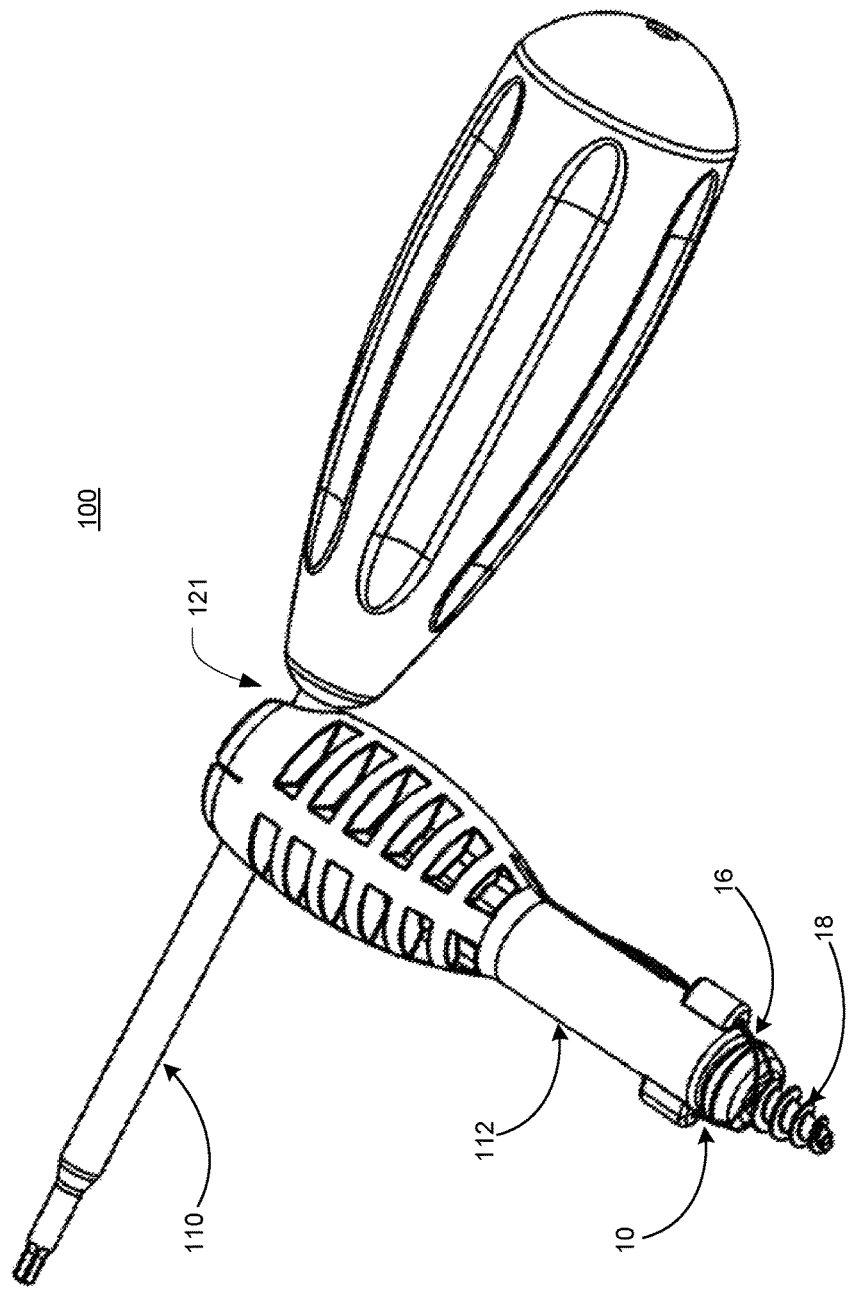

Turning now to FIGS. 16 and 17, with the implant 16 disposed between the anchor 18 and the second end region 132b of the biasing body 112, and the driver 110 (along with the suture 114 generally secured thereto) disposed within the driver cradle 121, the surgeon may rotate the driver 110 about longitudinal axis A to reduce the length L of the suture 114 extending between the driver 110 and the contact portion 120 of the anchor 118. The reduction in the length L of the suture 114 generates a biasing force which urges the implant 16 into engagement with the anchor 18. As may be appreciated, the implant delivery system 100 generates a biasing force which is applied against the implant 16 and anchor 18 through the suture 114 only (i.e., substantially no force is applied to the surrounding bone 14 or tissue).

More specifically, because the suture 114 supports the anchor 18, rotation of the driver 110 about longitudinal axis A increases the tension on the suture 114 (and therefore the biasing force between the implant 16 and the anchor 18) in an opposite direction of the downward force being placed upon the implant 16 by the biasing body 112. Continued rotation of the driver 110 increases the biasing force between the implant 16 and the anchor 18 and, once the biasing force exceeds the required threshold to install the implant 16, the implant 16 may be successfully installed (e.g., secured) in the anchor 18. Thus, as a result of the suture 114 applying a relatively equal and opposite force to the anchor 18 and the biasing device 110 (and therefore the implant 16), the underlying bone 14 and other structures are not affected, preventing or reducing potential injury from securing the implant 16 into the anchor 18. The implant delivery system 100 therefore avoids and/or reduces any impact to the bone 14 (e.g., eliminates blunt force due to a hammer/mallet or the like), and therefore avoids and/or reduces damage to the bone 16.

Because the biasing force is not transmitted/applied into the surrounding bone 14 or tissue, the implant delivery system 100 may be used with small bones (such as, but not limited to, phalange bones and/or metatarsal bones in the foot and/or hands. Additionally, because the implant delivery system 100 is capable of generating high biasing forces without transmitting/applying the biasing force to the surrounding bone 14 or tissue, the connection between the implant body 16 and the anchor 18 (e.g., first and second fixation elements 24, 26 as discussed herein) may be stronger and more robust, thereby increasing the life expectancy of the implant system 10. Moreover, the implant delivery system 100 may deliver the biasing force uniformly to the implant 16 and be self-leveling or self-aligning, thereby reducing and/or eliminating the difficulties associated with aligning the implant 16 with respect to the anchor 18.

Once the implant 16 is secured to the anchor 18, the suture 114 may be removed from the implant system 10. For example, one or more portions of the suture 114 may be cut and the resulting pieces may be removed (e.g., pulled out)

from the excision site 20. Alternatively, a first end of the suture 114 may be released and the suture 114 may be pulled through the biasing body 120 by a second end of the suture 114, resulting in the first end traveling through the shaft passageway 132c, through one of the suture passageways 136a, 136b, out one of the alignment guides 138a, 138b, around the anchor 18 and through the second of the alignment guides 138a, 138b and suture passageways 136a, 136b, and the shaft passageway 132. However, example embodiments may vary and are not limited thereto.

If the suture 114 is cut prior to removal, example embodiments may vary and may include the suture 114 having various shapes or loops. For example, the suture 114 may form a basket or loop to wrap around the anchor 18. This shape may help support the anchor 18 and may increase control over the anchor 18 prior to the suture 114 being wrapped around the driver 110. In this configuration, the loop may extend so that the loop can be severed after installation of the implant system 10.

It may be appreciated that the strength or ruggedness of the snap-fit connection between the implant 16 and the anchor 18 may depend on the selected materials (e.g., the rigidity) and size/dimensions. In general, more rigid (i.e., less deformable) materials and/or larger sizes/dimensions will result in a stronger, more robust connection between the implant 16 and the anchor 18. While a stronger and more robust connection between the implant 16 and the anchor 18 is generally desirable, the resulting force necessary to make the snap-fit connection increases.

Traditionally, the force necessary to secure the implant 16 to the anchor 18 has been generated using a blunt force, e.g., a hammer/mallet or the like. More specifically, with the anchor 18 secured in the bone 14, the surgeon attempts to align the implant 16 relative to the anchor 18 and impacts the implant 16 with the hammer/mallet to force the implant 16 into engagement with the anchor 18. As may be appreciated, however, a substantial amount of force is also applied to the surrounding bone 14, and if the force applied to the bone 14 is too great, the bone 14 may be damaged. Consequently, the strength of the connection between the implant 16 and the anchor 18 may be limited in many applications (e.g., but not limited to, small bones in the hand and foot as well as implant system 10 installed proximate to the perimeter of a bone) by the strength of the surrounding bone 14. Additionally, it may be very difficult for the surgeon to properly align the implant 16 with respect to the anchor 18.

As discussed herein, the implant delivery system consistent with one embodiment of the present disclosure solves this problem by generating a biasing force to secure the implant 16 to the anchor 18 wherein the biasing force is only applied against the implant 16 and the anchor 18. The biasing force generated by the implant delivery system may therefore be applied only to the implant system 10, and not the surrounding bone or tissue 14. An implant delivery system consistent with the present disclosure may also be used to facilitate securing the anchor 18 into the bone 14.

It should be appreciated that the implant system 10 illustrated with respect to FIGS. 9-17 is provided for illustrative purposes, and that the implant delivery system may be used with any multi-piece implant having an anchor that is coupled (either directly or indirectly) to an implant/implant body. For example, the implant delivery system may be used with implant systems for replacing any articular surface such as, but not limited to, shoulder joints (e.g., but not limited to, the glenohumeral joint), hip joint (e.g., but not limited to, the acetabulofemoral joint), foot and/or hand joints (e.g., but not limited to, metacarpophalangeal joints, metatarsophalangeal joints, and/or interphalangeal joints), or the like. The implant systems may include total joint implants (wherein all or substantially all of the articular surface of at least one bone is replaced with the artificial surface of the implant) and/or partial implants (wherein substantially only the damaged portion(s) of the articular surface of a bone is replaced with the artificial surface of the implant). The implant delivery system may also be used to secure together a multi-piece pin or rod in a bone to facilitate healing of a fracture or broken bone.

Figure 18:
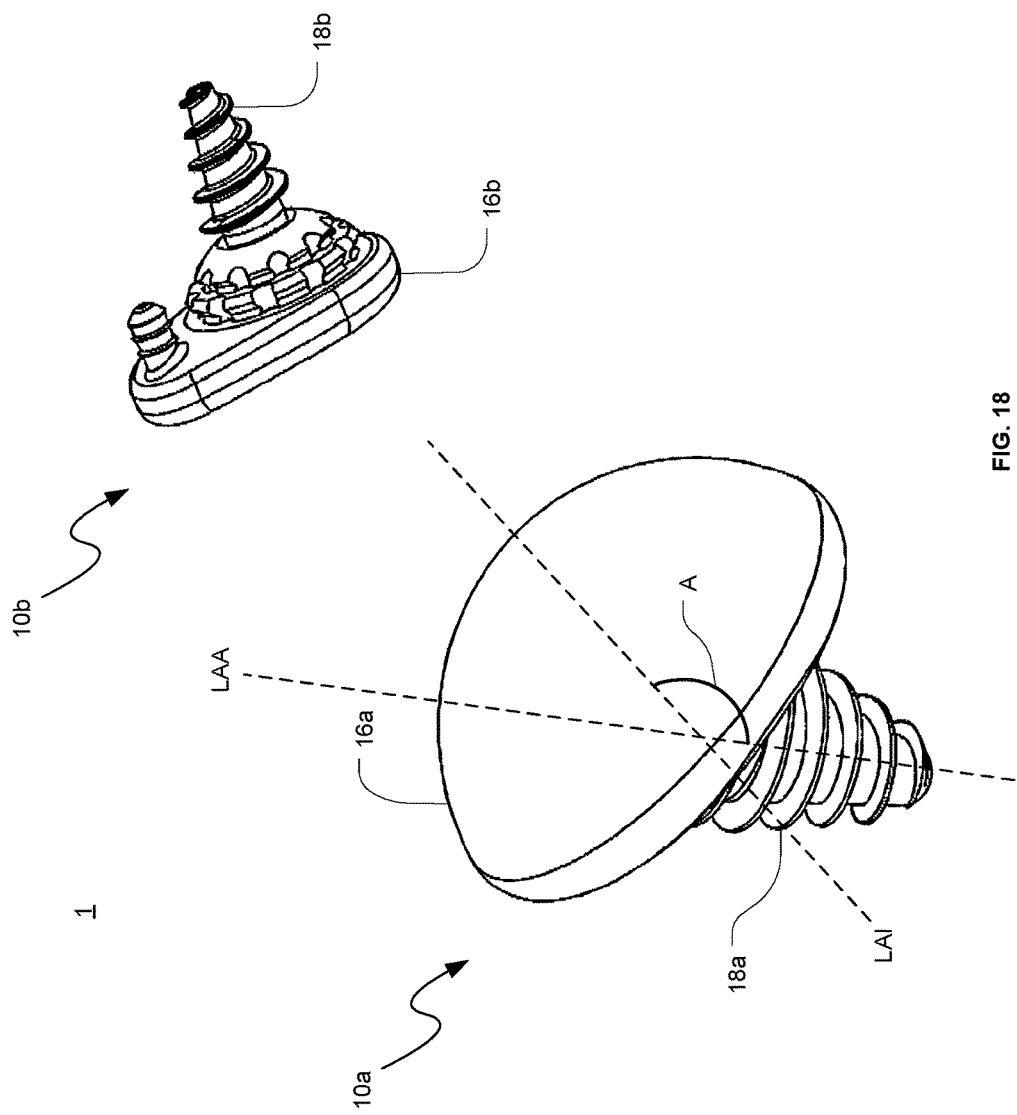
FIG. 18 generally illustrates yet another embodiment of an implant system which may be used with the total joint replacement system consistent with at least one embodiment of the present disclosure.

Turning now to FIG. 18, yet another embodiment of the total joint replacement system 1 consistent with the present disclosure is generally illustrated. The total joint replacement system 1 may include first implant system 10a and a second implant system 10b. While the total joint replacement system 1 will be described in terms of a shoulder joint, it should be appreciated that this is not a limitation of the present disclosure unless specifically claimed as such. For the sake of clarity, the bones are not illustrated.

The first implant system 10a may be configured to replace and/or repair the humeral head, and may be similar to the implant system 10 described with respect to FIGS. 4 and 5-6. The implant 16a may include a first fixation element 32 configured to be secured to the second fixation element 44 of the anchor 18a as described herein (e.g., using one or more first fixation elements 32 configured to be secured to one or more second fixation elements 44). The anchor 18a may be secured, for example, into the humerus. The implant 16a may have a generally hemispherical configuration, for example, which generally corresponds to the humeral head (e.g., a "ball shape"). The implant 16a (e.g., the first fixation element 32) may be configured to be secured to the anchor 18a (e.g., the second fixation element 44) at any angle A. For example, the angle A may be defined by the longitudinal axis LAA of the anchor 18a and the longitudinal axis LAI of the implant 16a. The angle A may be determined based on the amount of the humeral head removed with respect to the rest of the humerus. The angle A may include any angle within the range of 0 degrees to approximately 90 degrees, for example, within the range of 0 degrees to approximately 45 degrees, within the range of 0 degrees to approximately 25 degrees, and/or within the range of 0 degrees to approximately 15 degrees, including all values and ranges therein.

The second implant system 10b may be configured to replace and/or repair the glenoid. The second implant system 10b may include any implant system/assembly as described in U.S. Provisional Application Ser. No. 61/949,789, filed Mar. 7, 2014, which is fully incorporated herein by reference.

Figure 19:
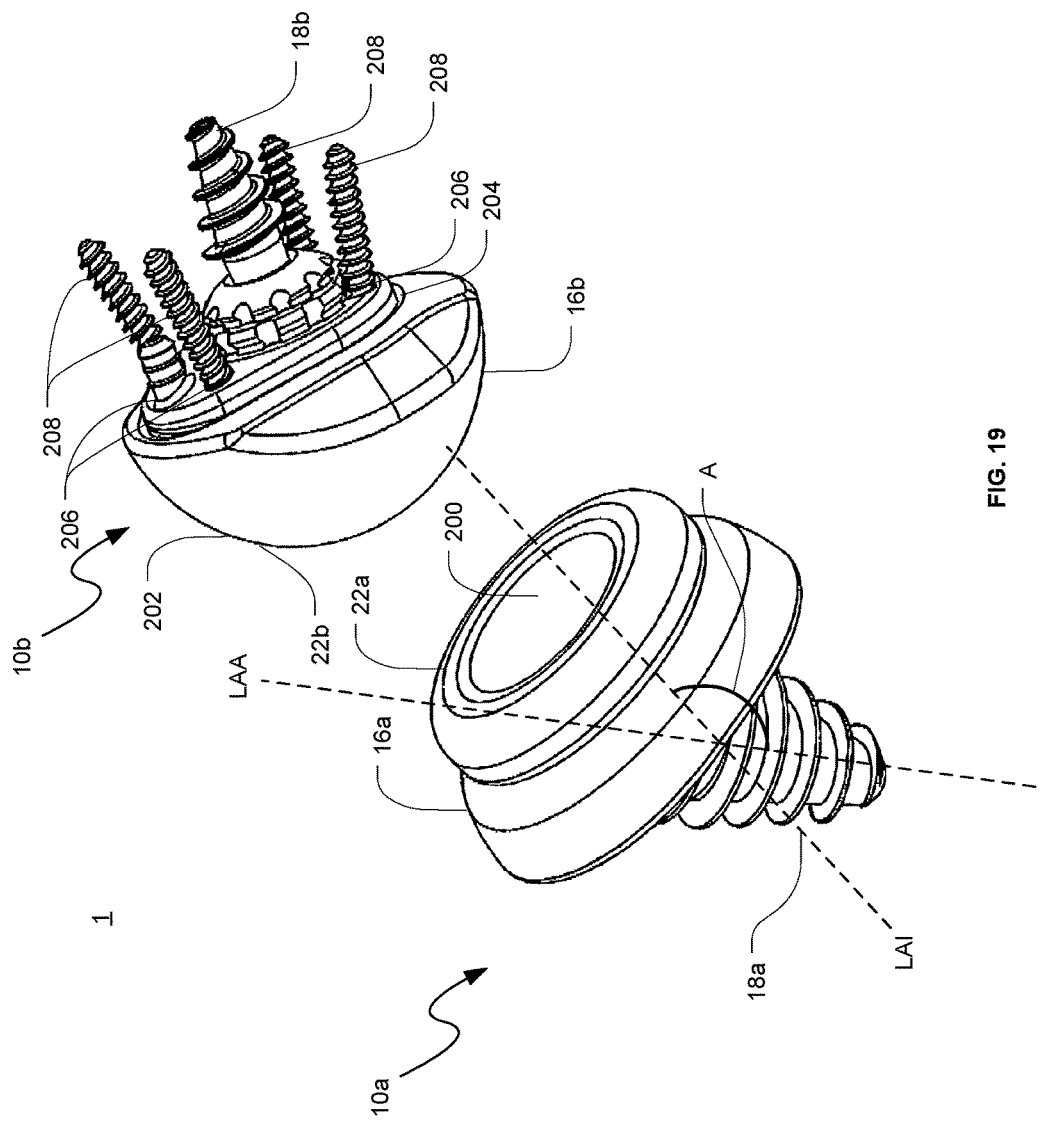
FIG. 19 generally illustrates a further embodiment of an implant system which may be used with the total joint replacement system consistent with at least one embodiment of the present disclosure.

The total joint replacement system 1 as generally illustrated in FIG. 18 may therefore repair and/or replace the shoulder joint. Turning now to FIG. 19, yet a further embodiment of the total joint replacement system 1 consistent with the present disclosure is generally illustrated. The total joint replacement system 1 of FIG. 19 may include first implant system 10a and a second implant system 10b, and may be used to repair and/or replace a shoulder joint (though it should be appreciated that this is not a limitation of the present disclosure unless specifically claimed as such). For the sake of clarity, the bones are not illustrated.

The total joint replacement system 1 may be referred to as a "reverse shoulder." The shoulder may be thought of as a ball and socket joint in which he humeral head is a ball and the glenoid is a socket. In the total joint replacement system 1 of FIG. 19, the orientation of the ball is socket is reversed. As such, implant system 10a (which may be secured to the humerus) may include an anchor 18a and an implant 16a having a load bearing surface 22 at least partially defining a socket 200. The implant 16a may be disposed at an angle A with respect to the anchor 18a as described herein.

The second implant system 10b may include an implant 16b and an anchor 18b. The implant 16b may be secured to the anchor 18b as generally described herein (e.g., using one or more first fixation elements 32 configured to be secured to one or more second fixation elements 44). The implant 16b may include an implant body 202 and a support plate 204. The implant body 202 may define a load bearing surface 22b, for example, having a generally hemi-spherical configuration (e.g., ball) configured to articulate in the socket 200 of the first implant system 10a. The implant body 202 may be secured to the support plate 204 in any manner known to those skilled in the art. For example, the implant body 202 may be secured to the support plate 204 using a tapered connection similar to the first and second fixation elements 32, 44 as described herein. The support plate 204 may optionally include one or more apertures 206 configured to receive anchoring screws 208. The anchoring screws 208 aid in securing the support plate 204 (and therefore the implant 18b) to the bone.

According to one embodiment, the total joint replacement system 1 of FIG. 18 may be partially replaced with the total joint replacement system 1 of FIG. 19. In particular, a patient may initially have the total joint replacement system 1 of FIG. 18 installed in the shoulder joint. If it is later desired to replace the total joint replacement system 1 of FIG. 18 with a reverse shoulder, the anchors 18a, 18b of FIG. 18 may remain secured within the humerus and glenoid, respectively. The implants 16a, 16b of FIG. 18 may be removed and replaced with the implants 16a, 16b of FIG. 19. Leaving the anchors 16a, 16b of FIG. 18 within the bones reduces the potential for damage to the bones if corrective surgery is later needed. As such, any of the implants 10 that may be used with the total joint replacement system 1 of the present disclosure may be considered modular.

In accordance with yet another embodiment of the present disclosure, an implant system is disclosed herein that allows for partial or total reconstruction of an articular surface of a bone. Suitable bones include, but are not limited to, humerus bones, femur bones, and/or any other bone type having an articular surface for forming a joint.

The implant system includes an anchor portion configured to be coupled to an implant portion. The anchor portion is configured to engage with/secure to the bone and the implant portion includes a load bearing surface that at least partially replaces the patient's articular surface. The anchor portion includes one or more anchor fixation heads configured to be at least partially received in a corresponding implant fixation cavity to couple the anchor portion with the implant portion. The anchor portion may be formed from a material (e.g., such as titanium, stainless steel, or another suitable metal/alloy) that is less dense than the material of the implant portion. The implant portion may be formed from a material (e.g., such as Cobalt-Chromium (CoCr) or other suitable material) that has a higher wear-resistance than the material of the anchor portion. As explained herein, the size and shape of the anchor fixation head and the implant fixation cavity, as well as the material selection of the anchor and implant portions, may reduce the overall weight of the implant system while still allowing the implant system to have excellent wear resistance.

It may be appreciated, however, that the anchor and implant portions may be formed from a same material (e.g., steel, titanium, Cobalt-Chromium or any other suitable metal/alloy), and this disclosure is not necessarily limited to an implant system having two different materials unless specifically claimed as such.

Figure 20:
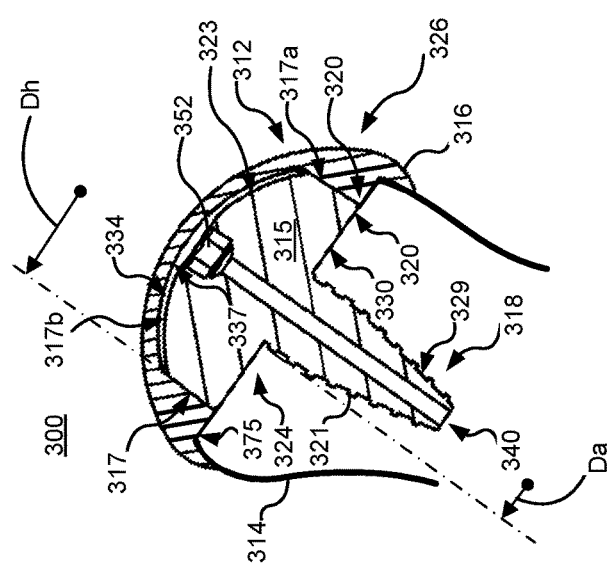
FIG. 20 generally illustrates an implant system installed in a patient's joint consistent with at least one embodiment of the present disclosure.

Turning now to FIG. 20, an embodiment of an implant system 300 (or joint replacement system 300) installed in a patient's humerus bone 314 (referred to herein as bone 314 for simplicity) is generally illustrated. While specific reference is made to a humerus bone in the proceeding aspects and examples, this disclosure is not limited in this regard and is equally applicable to other bones having articular surfaces/cartilage. The implant system 300 is configured to repair and/or replace a portion of or the entire articular surface of the humerus head of the humerus bone 314.

With reference to FIGS. 21-26, the implant system 300 includes an anchor portion 324 configured to be coupled to an implant portion 326. The anchor portion 324 (e.g., the anchor fixation head 315 and/or anchor 318) may optionally include a cannulated passageway 340 that extends from a first end to a second end generally along the longitudinal axis 305 of the anchor portion 324.

The anchor portion 324 includes an anchor fixation head 315 and an anchor 318. As used herein, the anchor 318 is defined as the part of the anchor portion 324 that is configured to be surrounded by the bone 314 beneath the excision site 320 when the anchor portion 324 is coupled/secured to the bone 314. At least a portion of the anchor 318 is also configured to engage with and/or secure the anchor portion 324 to the bone 314. According to one embodiment, the anchor 318 includes an elongated shaft/body 311, e.g., that may extend along the longitudinal axis 305 of the anchor portion 324. As used herein, the anchor fixation head 315 is defined as the part of the anchor portion 324 that is configured to be disposed external to (e.g., above) the bone 314 when the anchor portion 324 is coupled/secured to the bone 314 beneath the excision site 320.

The anchor portion 324 (e.g., the anchor fixation head 315 and the anchor 318) may be formed integrally from a single piece of material, e.g., as generally illustrated in FIGS. 21-26. Alternatively, the anchor portion 324 may be formed from two or more (e.g., via multiple pieces), which may be the same or different materials, e.g., as generally illustrated in FIG. 25. For example, the anchor fixation head 315 may be configured to be coupled to the anchor 318 in any manner known to those skilled in the art including, but not limited to, one or more friction connections 371 (e.g., a pair of Morse tapered mating surfaces), snap fit connections, and/or positive mechanical engagement connections.

With reference back to FIGS. 20-26, the anchor fixation head 315 includes an anchor bone facing surface 330 and an implant facing surface 323. The anchor fixation head 315 may be formed from a first material that is less dense than the implant portion 326 and suitable for use within implant devices. For example, the first material may comprise a metal such as titanium, steel, or other suitable metal/alloy. In some cases, the first material may be non-metal and formed from a ceramic, plastic and/or polymer. Note that the anchor fixation head 315 may not necessarily be formed from a light-weight (less dense) material depending on a desired configuration.

The anchor bone facing surface 330 extends generally radially outward from a first (e.g., proximal) end of the anchor 318 (e.g., the shaft/body 311) such that the anchor fixation head 315 has a cross-section that is greater than the cross-section of the anchor 318. According to one embodiment, at least a portion of the outer periphery of the anchor bone facing surface 330 (e.g., the entire outer periphery of the anchor bone facing surface 330) may extend radially outward a maximum radial distance Dh from a longitudinal axis 305 of the anchor 318 that is larger than the maximum radial distance Da of the outer periphery of the anchor 318 from the longitudinal axis 305.

The anchor bone facing surface 330 may optionally include a contour that substantially matches the resulting contour of the bone 314 within the excision site 320. For example, the anchor bone facing surface 330 may have a surface contour generally corresponding to the surface contour of the excision device revolved around the working axis used when forming the excision site 320. To this end, the anchor bone facing surface 330 may include a contour that is revolved around the longitudinal axis 305 of the anchor portion 324, and the bone facing surface 330 may directly contact the bone 314 within the excision site 320. It should be appreciated, however, that the bone-facing surface 330 may not necessarily directly contact the bone 314 and may include a gap (e.g., an air gap, or a gap comprising a bone cement or other suitable adhesive) therebetween, depending on a desired configuration.

In the illustrated embodiment, the anchor bone facing surface 330 extends generally perpendicularly radially outward from a first end of the anchor 318, though it should be appreciated that the anchor bone facing surface 330 may extend radially outward at an angle greater than and/or less than 90 degrees with respect to the longitudinal axis 305 of the anchor portion 324, e.g., as generally illustrated in FIGS. 27 and 28. As such, while the longitudinal axis 305 of the anchor portion 324 is illustrated in FIGS. 20-26 as being generally parallel or collinear with the central axis 306 of the implant portion 326, it should be appreciated that the anchor fixation head 315 may be configured to be coupled to the implant portion 326 such that the central axis 306 of the implant portion 326 intersects with the longitudinal axis 305 of the anchor portion 324 at a single point and the two axis 305, 306 are not parallel or collinear to each other (e.g., as generally illustrated in FIGS. 27 and 28).

Referring back to FIGS. 20-26, the anchor fixation head 315 also includes an implant facing surface 323. The implant facing surface 323 is defined as a surface that is adjacent to (e.g., but not limited to, abutting) the anchor facing surface 337 of the fixation recess 334 when the anchor fixation head 315 is received within the fixation recess 334. At least a portion of the implant surface 330 may include one or more mating surfaces 317 for coupling to the implant portion 326 to the fixation recess/cavity 334 of the implant portion 326 (e.g., for coupling the mating surfaces 317 to one or more corresponding mating surfaces 333 of the anchor facing surface 337).

According to one embodiment, the mating surface 317 may include a tapered outer profile (e.g., a Morse taper or the like) configured to form a friction connection with a corresponding mating surface 333 (e.g., tapered mating surface) of the fixation recess 334 of the implant portion 326. For example, the anchor fixation head 315 may include, but is not limited to, a tapered semi-spherical or hemispherical ball shape such as shown. It should be appreciated, however, that the anchor fixation head 315 of the anchor portion 324 may be coupled to the fixation recess/cavity 334 of the implant portion 326 in any other manner such as, but not limited to, a snap fit connection, threaded connection, or the like.

The implant facing surface 323 (and optionally the mating surface 317) of the anchor fixation head 315 may extend from the periphery of the anchor bone facing surface 330 around all or a portion of the implant surface 330 of the anchor fixation head 315. For example, the mating surface 317 of the implant facing surface 323 may include a first portion 317a that extends substantially parallel with a longitudinal axis 305 of the anchor 318. In some cases, a second portion 317b of the mating surface 317 may also extend along substantially transverse relative to the longitudinal axis 305 of the anchor 318. The first portion 317a may directly contact a corresponding mating surface 333a of the implant portion 326 when the anchor portion 324 is received in the fixation recess 334, for example to form a frictional connection therebetween. Alternatively (or in addition), the second portion 317b may directly contact a corresponding mating surface 333b of the implant portion 326 when the anchor portion 324 is received in the fixation cavity/recess 334 (e.g., to form a frictional connection therebetween), although other embodiments are within the scope of this disclosure.

Thus, it should be appreciated that all or a portion of the implant facing surface 323 may form the mating surface 317. In at least one embodiment, a gap (e.g., an air gap) may be formed between the portion of the implant facing surface 323 and the anchor facing surface 337 of the fixation recess 334, e.g., as generally illustrated in FIG. 20. While the mating surface 317 is shown extending from the periphery of the anchor bone facing surface 330, it should be appreciated that the present disclosure is not limited to this configuration, and the mating surface 317 may not extend from the periphery of the anchor bone facing surface 330.

As noted above, the implant facing surface 323 of the anchor fixation head 315 may have a generally hemispherical configuration configured to be received in a corresponding generally hemispherical fixation cavity/recess 334 of the implant portion 326 as described in more detail herein. One benefit to this configuration is that the anchor portion 324 may be rotated within the bone 314 to adjust the height of the anchor fixation head 315 (and thus the resulting height of the implant portion 326) relative to the bone 314/patient's articular surface without affecting the orientation of the implant portion 326 relative to the patient's original articular surface when the implant portion 326 is coupled to the anchor portion 324.

Figure 32:
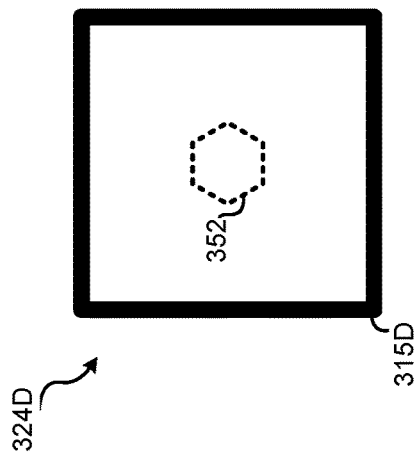
FIGS. 30-32 show various top plan views of an anchor portion that may be utilized in accordance with at least one embodiment of the present disclosure.
Figure 31:
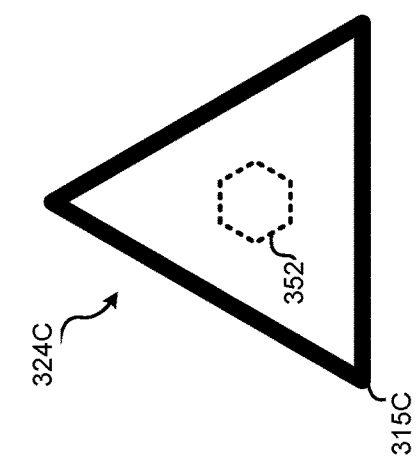
Figure 30:
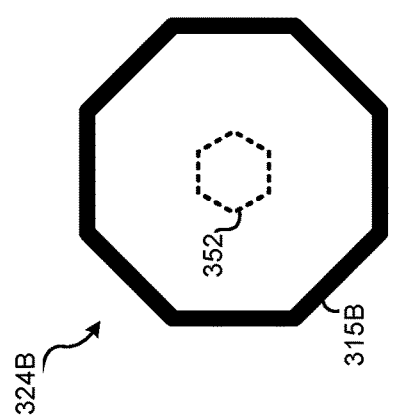

According to another embodiment, the anchor fixation head 315 may have a non-circular cross-section, e.g., as shown in FIGS. 30-32, configured to be received in a corresponding non-circular cross-sectional cavity/recess 334. One benefit to this configuration is that the anchor portion 324 cannot rotate relative to the implant portion 326 when the implant portion 326 is coupled to the anchor portion 324.

As noted herein, the anchor 318 refers to the part of the anchor portion 324 that is configured to be surrounded by the bone 314 beneath the excision site 320 when the anchor portion 324 is coupled/secured to the bone 314. At least a portion of the anchor 318 is also configured to engage with and/or secure the anchor portion 324 to the bone 314. According to one embodiment, the anchor 318 includes an elongated shaft/body 311, e.g., that may extend along the longitudinal axis 305 of the anchor portion 324.

According to one embodiment, the anchor 318 may include one or more threads 321 (which may be either continuous or discontinuous threads), ribs, rings, protrusions, barbs, bone-ingrowth materials (e.g., a bone-ingrowth matrix material, e.g., as generally illustrated in FIG. 26), or the like, which may extend along all and/or a portion of the shaft 311 of the anchor 318. The use of threads 321 as generally illustrated may advantageously allow the height of the anchor portion 324 (e.g., the anchor fixation head 315) to be adjusted relative to the excision site 320/articular surface by rotating the anchor 318 within the bone 314. For example, the anchor 318 may be rotated such that the anchor fixation head 324 (e.g., the bone facing surface 330) is flush with and/or abuts against the surface of the bone 314 within the excision site 320 (i.e., such that the anchor fixation head 315 is external to/above the bone 314 and the anchor 318 is surrounded by the bone 314).

As noted above, however, the anchor 318 does not have to include threads, and may be secured to the bone 314 in any manner know to those skilled in the art. For example, the anchor 318 may form a non-circular cross-sectional peg that may be pressed into (e.g., driven and/or pounded into) the bone 314 within the excision site 320 and/or may include one or more ribs, rings, protrusions, barbs, bone-ingrowth materials (e.g., bone-ingrowth matrix material, e.g., as generally illustrated in FIG. 26), or the like. Optionally, the anchor 318 may be secured to the bone 314/excision site 320 using bone cement.

The implant portion 326 includes an implant body 316 defining one or more fixation cavities/recesses 334, a load bearing surface 312 having a contour for articulating against an articulating surface (e.g., a load bearing surface and/or articular surface of the cooperating/corresponding bone of the joint), and optionally an implant bone-facing surface 375 disposed opposite the load bearing surface 312.

According to one embodiment, the implant portion 326 may form a generally hemispherical ball shaped load bearing surface 312 configured to articulate, at least in part, in a socket (such as, but not limited to, a glenoid fossa or other joint); however, the shape of the load bearing surface 312 may depend on the intended application. For instance, the articular surface 312 may include one or more concave regions.

The load bearing surface 312 may have a contour that substantially matches and/or is based on the contours of the patient's original articular surface that is removed when forming the excision site 320. The contour of the load bearing surface 312 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates. The load bearing surface 312 may be based on two or more curvatures, for example, the anterior-posterior curvature and the superior-inferior curvature. One or more of the anterior-posterior and/or superior-inferior curvatures may themselves be based on multiple curves, (for example, as generally described in U.S. patent application Ser. No. 12/027,121, filed Feb. 6, 2008 and entitled System and Method for Joint Resurface Repair, which is fully incorporated herein by reference).

Alternatively, in the case of a total joint replacement in a ball and socket type joint (e.g., shoulder), the load bearing surfaces may be reversed (i.e., the load bearing surface 312 of the implant portion 326 which is secured in the humeral head may form a socket shaped load bearing surface 312 and the glenoid implant (not shown) may form a ball shaped load bearing surface), for example, as generally described in FIGS. 18 and 19. As such, the load bearing surface 312 may not substantially match and/or be based on the contours of the patient's original articular surface that is removed when forming the excision site 320.

The implant portion 326 may be formed from a single piece of material or formed via multiple pieces (which may be the same or different materials). The implant portion 326 may be formed from a second material that has a higher wear-resistance and/or higher density compared to the material of the anchor portion 324. For example, the implant portion 326 may be formed of a material having an absolute density of greater than 5 g/cm$^3$, for example, greater than 8 g/cm$^3$. In at least one embodiment, the implant portion 326 may be formed from cobalt-chromium (CoCr) and/or CoCr alloys, although the present disclosure is not limited to CoCr and other materials are within the scope of this disclosure. In some cases, the implant portion 326 may include a material (e.g., but not limited to, CoCr/CoCr alloy) having a hardness ranging from a greater than 500 MPa (e.g., 550-800 MPa) and/or a tensile strength greater than 145 MPA (e.g., 145-270 MPa). The CoCr alloy may optionally include nickel, carbon, and/or nitrogen to stabilize the γ phase in order to further increase ductility and reduce occurrences of component fracture. Additionally, the second material may be non-metal and formed from a ceramic, plastic and/or polymer. In at least one embodiment, the implant portion 326 may include an outer layer of a second material that at least partially covers/surrounds a core material (e.g., forming a body that defines the implant fixation cavity 334), wherein the second material has a higher wear-resistance and/or higher density compared to the core material.

Figure 22:
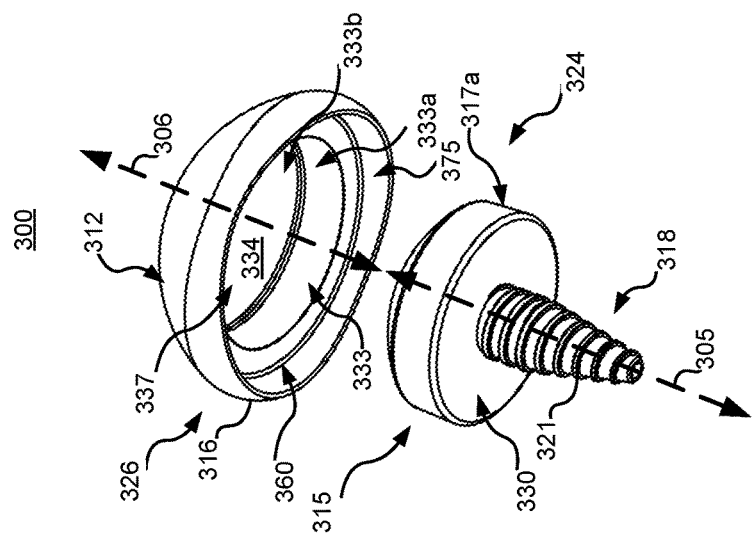
FIGS. 21 and 22 are perspective views that collectively illustrate the implant system of FIG. 20 in accordance with an embodiment of the present disclosure.
Figure 21:
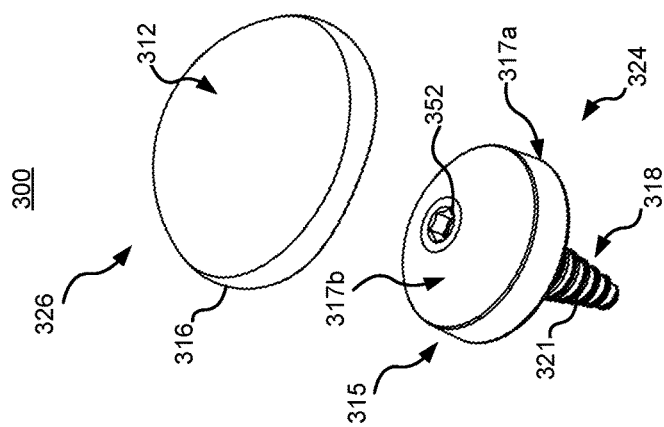

The implant body 316 further provides a fixation recess 334 (also be referred to as a fixation receptacle or cavity), which is more clearly shown in FIGS. 22 and 23. The fixation recess 334 includes an anchor facing surface 337 that is disposed within an opening 360. At least a portion of the anchor facing surface 337 of the fixation recess 334 includes one or more mating surface 333 for coupling to the corresponding mating surface 317 of the anchor portion 324. For example, the mating surface 333 may include a tapered outer profile (e.g., a Morse taper or the like) configured to form a friction connection with a corresponding mating surface 317 (e.g., tapered mating surface) of the anchor fixation head 315 of the anchor portion 324. In at least one embodiment, the fixation recess 334 may include, but is not limited to, a tapered semi-spherical or hemispherical recess shape such as shown. It should be appreciated, however, that the fixation recess 334 of the implant portion 326 may be coupled to the anchor fixation head 315 of the anchor portion 324 in any other manner such as, but not limited to, a snap fit connection, threaded connection, or the like.

According to one embodiment, the mating surface 333 of the implant portion 326 may extend from the periphery of the opening 360 of the implant portion 326. In addition (or alternatively), the mating surface 333 of the implant portion 326 may extend from the periphery of a bone facing surface 375 of the implant portion 326. In either case, the mating surface 333 may extend around all or a portion of the inner surface of the fixation recess 334. For example, the mating surface 333 may include a first portion 333a that extends substantially parallel with a longitudinal axis 306 of the implant portion 326. The first portion of the mating surface 333a may frictional engage with the first portion 317a of the anchor fixation head 315. Alternatively (or in addition), a second portion 333b of the mating surface 333 may extend along substantially transverse relative to the longitudinal axis 306 of the implant portion 326, and may optionally frictionally engage with the second portion 317b of the anchor fixation head 315 (though it should be appreciated that a gap (e.g., an air gap) may be formed between the mating surface 317 of the anchor fixation head 315 and the mating surface 333 of the fixation cavity/recess 334, e.g., such as shown in FIG. 20). While the mating surface 333 is shown extending from the periphery of the bone facing surface 375 (i.e., from the opening 60), it should be appreciated that the present disclosure is not limited to this configuration, and the mating surface 333 may not extend from the periphery of the anchor bone facing surface 375 and may form only a portion of the anchor facing surface 337.

The implant bone-facing surface 375 may overlap a portion of the bone 314 to fully cover/surround the anchor fixation head 315 of the anchor portion 324 and a portion of the bone 314. The implant bone facing surface 375 may optionally include a contour that substantially matches the resulting contour of the bone 314 within the excision site 320. For example, the implant bone facing surface 375 may have a surface contour generally corresponding to the surface contour of the excision device revolved around the working axis used when forming the excision site 320. To this end, the implant bone facing surface 375 may include a contour that is revolved around the longitudinal axis 306 of the implant portion 326, and the implant bone facing surface 375 may directly contact the bone 314 within the excision site 320. In one embodiment, the implant bone facing surface 375 extends from the opening 360 of the fixation cavity 334, though this is a not a limitation of the present disclosure unless specifically claimed as such. All or a portion of the implant bone facing surface 375 may directly contact the bone 314. Alternatively, all or a portion of the implant bone facing surface 375 may be separated from the bone 314, for example, by way of a gap. The gap may be optionally at least partially filled with bone cement or the like.

As may be appreciated, the load bearing surface 312 of the implant portion 326 may be constructed from a material having a high wear resistance such that the implant system 300 does not prematurely wear out during use. One disadvantage to many high wear resistant materials (e.g., but not limited to, CoCr) is that they are typically very dense, and as a result, the weight of the implant system 300 may become a factor as the surface area of the load bearing surface 312 increases.

As noted herein, the size and shape of the anchor fixation head 315 and the implant fixation cavity 334, as well as the material selection of the anchor portion 324 and implant portion 326, may reduce the overall weight of the implant system 300 while still allowing the implant system 300 to have excellent wear resistance and structural strength. In particular, the anchor portion 324 includes an anchor fixation head 315 that is constructed from a material that is less dense than the material of the implant portion 326 while also providing support for the implant portion 326 (thereby ensuring that the implant portion 324 does not distort when exposed to stress/forces during use). As a result, the amount of high wear resistant material used to form the implant portion 326 may be significantly reduced because the anchor portion 324 (e.g., the anchor fixation head 315) may occupy a greater volume of the implant system 300.

For example, as best shown in FIG. 23, the fixation recess 334 may define a volume Vr that is greater than or equal to 50% of the total volume Vi of the implant portion 326. As used herein, the volume Vr of the fixation recess 334 is defined as the volume of the fixation recess 334 between the opening 360 of the fixation recess 334 and the anchor facing surface 337 of the fixation recess 334. Additionally, as used herein, the total volume Vi of the implant portion 326 is defined as displacement volume of the implant portion 326. For example, the volume Vr of the fixation recess 334 may be greater than or equal to 60% of the total volume Vi of the implant portion 326, the volume Vr of the fixation recess 334 may be greater than or equal to 70% of the total volume Vi of the implant portion 326, and/or the volume Vr of the fixation recess 334 may be greater than or equal to 80% of the total volume Vi of the implant portion 326, including all values and ranges therein.

Similarly, the anchor fixation head 315 may define a volume Vh that is greater than or equal to 50% of the total volume Vi of the implant portion 326. As used herein, the volume Vh of the anchor fixation head 315 is defined as the volume of the anchor portion 324 that is configured to be disposed external to (e.g., above) the bone 314 when the anchor portion 324 is coupled/secured to the bone 314 beneath the excision site 320. For example, the volume Vh of the anchor fixation head 315 may be greater than or equal to 60% of the total volume Vi of the implant portion 326, the volume Vh of the anchor fixation head 315 may be greater than or equal to 70% of the total volume Vi of the implant portion 326, and/or the volume Vh of the anchor fixation head 315 may be greater than or equal to 80% of the total volume Vi of the implant portion 326, including all values and ranges therein.

The opening 360 of the fixation recess 334 may have a cross-section that is greater than the cross-section of the anchor 318. According to one embodiment, the opening 360 may extend radially outward a maximum radial distance Do from a longitudinal axis 306 of the anchor portion 326 that is larger than the maximum radial distance Da of the anchor 318. For example, the opening 326 and the anchor 318 may have circular cross-sections, and maximum radial distance Do (e.g., diameter) may be larger than maximum radial distance Do (e.g., diameter Da), though it should be appreciated that the opening 360 and/or anchor 318 may have non-circular cross-sections. The maximum radial dimension Do of the opening 360 may also be approximately equal to the maximum radial dimension Dh of the implant fixation head 315 (e.g., such that a frictional connection may be formed therebetween).

The maximum radial dimension Do of the opening 360 may be greater than 50% and less than 95% of the maximum radial dimension Di of the implant portion 326. For example, the maximum radial dimension Do of the opening 360 may be greater than 60% and less than 95% of the maximum radial dimension Di, the maximum radial dimension Do of the opening 360 may be greater than 70% and less than 95% of the maximum radial dimension Di, and/or the maximum radial dimension Do of the opening 360 may be greater than 80% and less than 95% of the maximum radial dimension Di, including all values and ranges therein.

Figure 29:
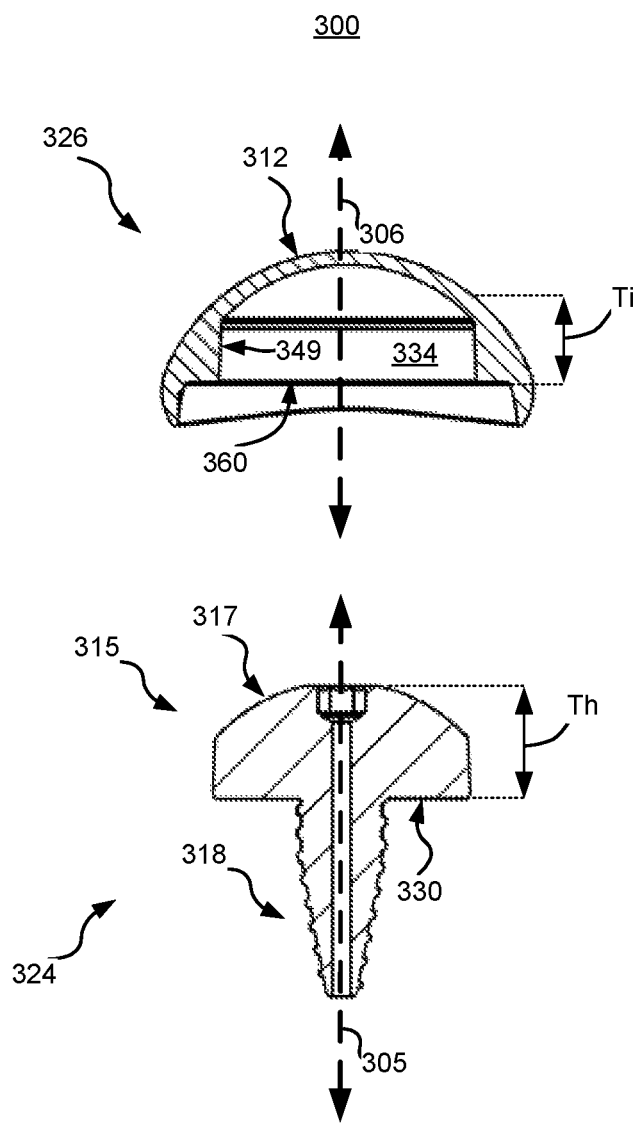
FIG. 29 shows another cross-sectional view of another embodiment of the implant system of FIG. 20.

In at least one embodiment, the maximum thickness Ti of the implant portion 326 is less than the maximum thickness Th of the anchor fixation head 15, such as shown in FIG. 29. As used herein, the maximum thickness Ti of the implant portion 326 is defined as the maximum thickness (e.g., distance) of the implant portion 326 between opposing sides of load bearing surface 312 and the inner surface 349 of the fixation cavity 334 taken parallel to the longitudinal axis 306 of the implant portion 326. Additionally, as used herein, the maximum thickness Th of the anchor fixation head 315 is defined as the maximum thickness (e.g., distance) of the anchor fixation head 315 between opposing sides of bone facing surface 312 and the mating surface 317 of the anchor fixation head 315 taken parallel to the longitudinal axis 305 of the anchor portion 324. For example, the maximum thickness Ti of the implant portion 326 may be less than or equal to 50% of the maximum thickness Th of the anchor fixation head 315, the maximum thickness Ti of the implant portion 326 may be less than or equal to 40% of the maximum thickness Th of the anchor fixation head 315, the maximum thickness Ti of the implant portion 326 may be less than or equal to 30% of the maximum thickness Th of the anchor fixation head 315, the maximum thickness Ti of the implant portion 326 may be less than or equal to 20% of the maximum thickness Th of the anchor fixation head 315, and/or the maximum thickness Ti of the implant portion 326 may be less than or equal to 10% of the maximum thickness Th of the anchor fixation head 315, including all values and ranges therein.

The anchor portion 324 may include a driving feature, e.g., driving receptacle 352, configured to engage with a driver (e.g., a drill or other suitable apparatus) to rotate and drive the anchor 318 into the bone 314 (e.g., a pre-drilled opening 329 of FIG. 20) to bring the bone-facing surface 330 into proximity and/or contact with excision site 320. Alternatively, or in addition to the driving receptacle 352, the anchor portion 324 (e.g., the outer periphery of the anchor bone facing surface 330) may include contours that allow for driving the anchor portion 324 by providing surfaces that may be engaged with a tool/apparatus having a corresponding shape. For example, FIGS. 30-32 illustrate top-down plan views showing example configurations for the anchor portion 324. FIG. 30 shows the outer periphery of the anchor bone facing surface 330 having a hexagonal shape to provide sidewalls for engaging a corresponding tool. Likewise, FIG. 31 shows the outer periphery of the anchor bone facing surface 330 having a triangular shape. FIG. 32 shows the outer periphery of the anchor bone facing surface 330 having a generally rectangular or square shape. Other regular and irregular shapes are also within the scope of this disclosure.

The excision site 320 may be formed using any method and system known to those skilled in the art, such as, but not limited to, as the systems and methods as described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. As noted herein, the anchor 318 may optionally include a passageway 340, for example, a longitudinal passageway, configured to be advanced over a guide wire (not shown) as generally described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. For example, the anchor 318 may be inserted into bone 314 or may be inserted into a shaft drilled in the bone 314 to reduce risks or complications arising from the insertion of the anchor 318. Without limitation, a pilot hole may be formed in the bone 314 for receiving the anchor 318 prior to installing the anchor 318. A diameter of the pilot hole may be smaller than the anchor 318, although example embodiments may vary and are not limited thereto.

Once the anchor portion 324 has been secured to the bone 314, the implant portion 326 may then be coupled to the anchor portion 324. A region of the implant body 316 of the implant portion 326 (e.g., bone-facing surface 375) may overlap the bone 314 to fully cover/surround the anchor fixation head 315 of the anchor portion 324 and a portion of the bone 314. The implant portion 326 may be attached to the anchor portion 324 via a friction fit, adhesive, and/or any other suitable fixation approach.

Figure 35:
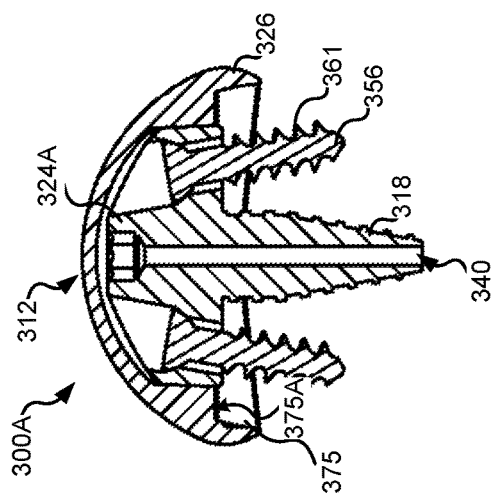
FIGS. 34 and 35 show an assembled and unassembled view of the implant system of FIG. 33, respectively, in accordance with an embodiment of the present disclosure.
Figure 34:
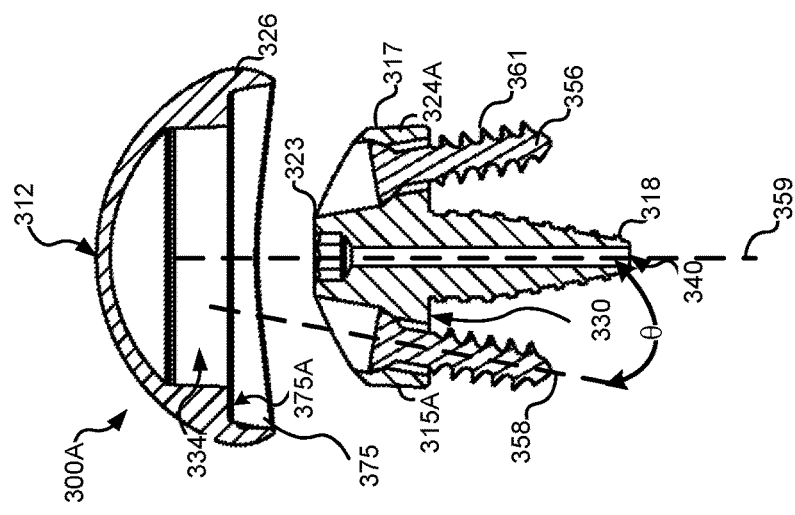
Figure 33:
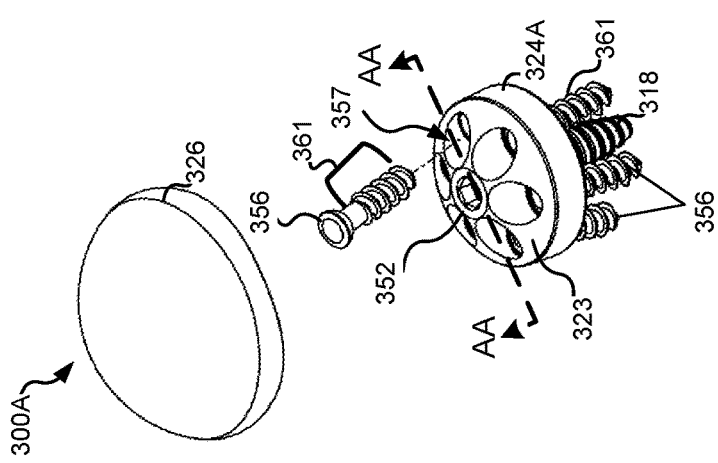
FIG. 33 generally illustrates a further example of an implant system consistent with at least one embodiment of the present disclosure.

Turning now to FIGS. 33-35, yet another embodiment of an implant system 300A consistent with the present disclosure is generally illustrated. As shown, the implant system 300A is substantially similar to the implant system 300 of any one of FIGS. 20-29 and may include an anchor portion 324A and an implant portion 326. Accordingly, the permutations and variations discussed in the proceeding description are equally applicable to the implant system 300A and will not be repeated for the sake of brevity. However, as further shown, the embodiment of the implant system 300A illustrated in FIGS. 33-35 further includes the anchor portion 324A having a plurality of fixation members 356 configured to extend at least partially through and/or around the anchor portion 324A to further secure the implant system 300A to a bone, e.g., the bone 314, which will now be discussed in greater detail.

The anchor portion 324A includes a plurality of fixation member openings 357, which may be disposed adjacent the driving receptacle 352 and the anchor 318. The plurality of fixation member openings 357 may extend through anchor fixation head 315. For example, the fixation member openings 357 may extend from the implant facing surface 323 of the anchor fixation head 315, through a portion of the anchor fixation head 315, to the bone facing surface 330. The fixation member openings 357 may be spaced evenly apart from each other and, for instance, the driving receptacle 352 and the anchor 318.

As shown more clearly in FIG. 34, each of the plurality of fixation member openings 357 may include an opening having a longitudinal axis 358 that is offset by an angle θ relative to a longitudinal axis 359 of the anchor portion 324A, or more specifically anchor 318, with angle θ being about 45 degrees±10 degrees. In some cases, angle θ may measure between 0 degrees to 50 degrees depending on a desired configuration. Other spacing configurations and angles may be utilized and the particular configuration shown is not intended to be limiting. Moreover, although six (6) fixation members 356 and associated fixation member openings 357 are shown, this should not be construed as limiting. For example, the anchor portion 324A may include less fixation members, e.g., a single fixation member 356 and associated opening 357, or may include a greater number of fixation members (e.g., more than six).

Each of the fixation members 356, which may also be referred to as secondary anchors, may comprise a screw, peg, nail, or other suitable type of fastening device. Each of the fixation members 356 may include threads 361, although this disclosure is not limited in this regard. Each fixation member may be secured to the bone 314, for example, using one or more external threads, ribs, protrusions, bone cement, barbs, grooves or any other suitable structure that enables the same to be secured to the bone 314. Note that in some cases each of the fixation members 356 may not necessarily include threads 361 and may form peg-like structures, similar to that of the anchor 318A shown in FIG. 26.

Each fixation member 356 may include a tapered shape whereby a head portion includes a width larger than the shaft portion in order to allow a driving device, e.g., a driving bit, to be inserted into a receptacle of the head portion to allow each fixation member 356 to be driven into a bone, e.g., a bone 314, to form a frictional connection therebetween. In some cases, the shaft of each fixation member 356 includes a tapered shape as well, similar to that of the anchor 318. In some cases, each of the fixation openings 357 may include a width that is slightly larger than each head portion to allow each fixation member 356 to be counter-sunk into the anchor fixation head 315A of the anchor portion 324A, such as shown.

However, other embodiments are within the scope of this disclosure and each fixation member 356 may not necessarily be countersunk into the anchor fixation head 315A. As generally referred to herein, countersunk generally refers to the head/driving portion of a fixation member 356 being disposed beneath the implant facing surface 323. To this end, each of the fixation member openings 357 may comprise a tapered recess which, in a general sense, acts as a stop to prevent an associated fixation member 356 from traveling beyond a certain point within the anchor fixation head 315A. Thus, each fixation member 356 may securely couple to the anchor fixation head 315 at a first end and within an associated fixation recess of the bone 314 (not shown) at the other end. Stated differently, the tapered shape of each fixation member opening 357 may result in each fixation member 356 forming a tapered connection with an associated fixation member opening 357 when inserted into the same.

FIG. 34 generally illustrates a cross-sectional view of one embodiment of an exploded, unassembled implant system 300A taken along the line A-A of FIG. 33, and FIG. 35 generally illustrates a cross-sectional view of the assembled implant system 300A also taken along the line A-A of FIG. 33. As shown, the anchor portion 324A includes a mating surface 317 and the implant portion 326 includes a fixation recess 334 for receiving at least a portion of the anchor portion 324A and coupling to the mating surface 317, via a frictional connection for example.

The implant system 300A may be attached to an excision site (not shown) in a manner similar to that of excision site 320 as described above with regard to any of the implant systems 300 of FIGS. 21-26.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A joint replacement system for repairing at least a first articular surface of a first bone of a joint, said system comprising:
   a first implant system comprising:
      an anchor portion formed from at least a first material, said anchor portion comprising:
         a first anchor configured to be secured to said bone; and
         an anchor fixation head including a bone-facing surface and an implant facing surface, wherein said bone-facing surface extends radially outward from said anchor, and wherein said implant facing surface extends from a periphery of said bone facing surface and includes a first mating surface; and
      an implant portion formed from at least a second material more dense than said first material, said implant portion comprising:
         a fixation cavity configured to receive at least a portion of said anchor fixation head, said fixation cavity including an anchor facing surface extending from an opening thereof, said anchor facing surface including a second mating surface configured to form a frictional connection with said first mating surface; and
         a first load bearing surface having a contour for articulating against a cooperating, second articulating surface associated with a second bone of said joint;
      wherein:
         said fixation cavity defines a volume Vr that is greater than or equal to 50% of a total volume Vi of said implant portion; and/or
         said anchor fixation head defines a volume Vh that is greater than or equal to 50% of said total volume Vi of said implant portion.

2. The joint replacement system of claim 1, further comprising:
   a second implant system comprising:
      a second implant having a second load bearing surface configured to articulate against said first load bearing surface; and
      a second anchor configured to be secured into said second bone, wherein said second anchor is configured to be secured to said second implant.

3. The joint replacement system of claim 2, wherein said second implant and said second anchor include a first and a second fixation element, respectively.

4. The joint replacement system of claim 3, wherein said first and said second fixation elements are configured to form tapered connection therebetween.

5. The joint replacement system of claim 4, wherein said first and said second fixation elements comprise a tapered cavity and a tapered protrusion configured to form tapered connection therebetween.

6. The joint replacement system of claim 3, wherein said first and said second fixation elements are configured to form a snap-fit connection therebetween.

7. The joint replacement system of claim 1, wherein said first load bearing surface is configured to replace substantially the entire first articular surface of said first bone.

8. The joint replacement system of claim 7, wherein said second load bearing surface is configured to replace substantially an entire second articular surface of said second bone.

9. The joint replacement system of claim 1, wherein said first load bearing surface is configured to replace a portion of said first articular surface.

10. The joint replacement system of claim 1, wherein said first load bearing surface has a contour based on a plurality of overlapping excision sites.

11. The joint replacement system of claim 1, wherein said first load bearing surface has a contour defining a socket.

12. The joint replacement system of claim 11, and wherein said second load bearing surface has a contour defining a generally hemispherical ball configured to articulate, at least in part, in said socket.

13. The joint replacement system of claim 1, and wherein said first load bearing surface has a contour defining a generally hemispherical ball.

14. The joint replacement system of claim 1, wherein said first material comprises steel, titanium, or an alloy thereof.

15. The joint replacement system of claim 1, wherein said second material comprises cobalt-chromium (CoCr).

16. The joint replacement system of claim 1, wherein said volume Vr is greater than or equal to 50% of said total volume Vi of said implant portion.

17. The joint replacement system of claim 1, wherein said volume Vh is greater than or equal to 50% of said total volume Vi of said implant portion.

18. The joint replacement system of claim 1, wherein said opening of said fixation cavity has a cross-section that is greater than a cross-section of said anchor.

19. The joint replacement system of claim 18, wherein said opening includes a maximum radial distance Do from a longitudinal axis of said anchor portion that is larger than a maximum radial distance Da of said anchor.

20. The joint replacement system of claim 1, wherein a maximum thickness Ti of said implant portion is less than a maximum thickness Th of said anchor fixation head.

21. The joint replacement system of claim 1, wherein said anchor fixation head has a cross-section that is greater than a cross-section of said anchor.

22. The joint replacement system of claim 21, wherein said implant portion includes at least one bone-facing surface extending radially outward from at least a portion of said opening of said fixation cavity.

23. The joint replacement system of claim 21, wherein said anchor facing surface has a generally hemispherical shape.

24. The joint replacement system of claim 1, wherein said anchor fixation head and said anchor are a unitary structure.

25. The joint replacement system of claim 1, wherein said implant facing surface of said fixation cavity has a shape that generally corresponds to the shape of implant facing surface of said anchor fixation head.

26. The joint replacement system of claim 1, wherein said first and said second mating surfaces have a tapered shape.

27. The joint replacement system of claim 1, wherein said anchor fixation head comprises at least one fixation member opening extending therethrough, said fixation member opening configured to receive a fixation member.

28. The joint replacement system of claim 27, further comprising said fixation member, and wherein said fixation member comprises a screw.

29. The joint replacement system of claim 1, wherein said first material comprises steel, titanium, or an alloy thereof, and wherein said second material comprises cobalt-chromium (CoCr).

30. A joint replacement system for repairing at least a first articular surface of a first bone of a joint, said system comprising:
a first implant system comprising:
an anchor portion formed from at least a first material, said anchor portion comprising:
a first anchor configured to be secured to said bone; and
an anchor fixation head including a bone-facing surface and an implant facing surface, wherein said bone-facing surface extends radially outward from said anchor, and wherein said implant facing surface extends from a periphery of said bone facing surface and includes a first mating surface; and
an implant portion formed from at least a second material more dense than said first material, said implant portion comprising:
a fixation cavity configured to receive at least a portion of said anchor fixation head, said fixation cavity including an anchor facing surface extending from an opening thereof, said anchor facing surface including a second mating surface configured to form a frictional connection with said first mating surface and said opening having a cross-section that is greater than a cross-section of said anchor fixation head; and
a first load bearing surface having a contour for articulating against a cooperating, second articulating surface associated with a second bone of said joint.

31. The joint replacement system of claim 30, wherein said implant portion includes at least one bone-facing surface extending radially outward from at least a portion of said opening of said fixation cavity.

32. The joint replacement system of claim 30, wherein said anchor facing surface has a generally hemispherical shape.

33. The joint replacement system of claim 30, further comprising:
a second implant system comprising:
a second implant having a second load bearing surface configured to articulate against said first load bearing surface; and
a second anchor configured to be secured into said second bone, wherein said second anchor is configured to be secured to said second implant.

34. The joint replacement system of claim 33, wherein said second anchor includes a threaded region configured to secure said second anchor to said second bone.

35. The joint replacement system of claim 33, wherein said second implant system includes a single anchor, wherein said second anchor is centrally located with respect to the second implant.

36. The joint replacement system of claim 33, wherein said second implant system includes a single anchor, wherein a longitudinal axis of said second anchor is collinear with a longitudinal axis of said assembled second implant system.

37. The joint replacement system of claim 33, wherein said first implant system includes a single anchor, wherein said first anchor is centrally located with respect to the first implant portion.

38. The joint replacement system of claim 33, wherein said first implant system includes a single anchor, wherein a longitudinal axis of said first anchor is collinear with a longitudinal axis of assembled first implant system.

39. The joint replacement system of claim 30, wherein said opening includes a maximum radial distance Do from a longitudinal axis of said anchor portion that is larger than a maximum radial distance Da of said anchor.

40. A joint replacement system for repairing at least a first articular surface of a first bone of a joint, said system comprising:

a first implant system comprising:
- an anchor portion formed from at least a first material, said anchor portion comprising:
  - a first anchor configured to be secured to said bone; and
  - an anchor fixation head including a bone-facing surface and an implant facing surface, wherein said bone-facing surface extends radially outward from said anchor, and wherein said implant facing surface extends from a periphery of said bone facing surface and includes a first mating surface; and
- an implant portion formed from at least a second material more dense than said first material, said implant portion comprising:
  - a fixation cavity configured to receive at least a portion of said anchor fixation head, said fixation cavity including an anchor facing surface extending from an opening thereof, said anchor facing surface including a second mating surface configured to form a frictional connection with said first mating surface; and
  - a first load bearing surface having a contour for articulating against a cooperating, second articulating surface associated with a second bone of said joint;
- wherein a maximum thickness Ti of said implant portion is less than a maximum thickness Th of said anchor fixation head.

41. A joint replacement system for repairing at least a first articular surface of a first bone of a joint, said system comprising:
a first implant system comprising:
- an anchor portion formed from at least a first material, said anchor portion comprising:
  - an anchor configured to be secured to said bone; and
  - an anchor fixation head including a bone-facing surface and an implant facing surface, wherein said bone-facing surface extends radially outward from said anchor, and wherein said implant facing surface extends from a periphery of said bone facing surface and includes a first mating surface; and
- an implant portion formed from at least a second material more dense than said first material, said implant portion comprising:
  - a fixation cavity configured to receive at least a portion of said anchor fixation head, said fixation cavity including an anchor facing surface extending from an opening thereof, said anchor facing surface including a second mating surface configured to form a frictional connection with said first mating surface; and
  - a first load bearing surface having a contour for articulating against a cooperating, second articulating surface associated with a second bone of said joint;
- wherein said anchor fixation head has a cross-section that is greater than a cross-section of said anchor; and
- wherein said anchor facing surface has a generally hemispherical shape.

* * * * *